US010435480B2

(12) United States Patent
Shah et al.

(10) Patent No.: US 10,435,480 B2
(45) Date of Patent: Oct. 8, 2019

(54) PROTEIN COATED POLYMERIC SUBSTRATE

(71) Applicant: Porvair Sciences Limited, King's Lynn (GB)

(72) Inventors: Deepan Shah, Newcastle upon Tyne (GB); Sion Phillips, Newcastle upon Tyne (GB)

(73) Assignee: Porvair Sciences Limited, King's Lynn (GB)

( * ) Notice: Subject to any disclaimer, the term of this patent is extended or adjusted under 35 U.S.C. 154(b) by 199 days.

(21) Appl. No.: 15/111,666

(22) PCT Filed: Jan. 14, 2015

(86) PCT No.: PCT/GB2015/050058
§ 371 (c)(1),
(2) Date: Jul. 14, 2016

(87) PCT Pub. No.: WO2015/107335
PCT Pub. Date: Jul. 23, 2015

(65) Prior Publication Data
US 2016/0347865 A1 Dec. 1, 2016

(30) Foreign Application Priority Data

Jan. 14, 2014 (GB) .................................... 1400562.3

(51) Int. Cl.
| | | |
|---|---|---|
| *C07K 17/06* | (2006.01) | |
| *C07K 17/08* | (2006.01) | |
| *C07K 14/245* | (2006.01) | |
| *G01N 33/543* | (2006.01) | |
| *C07K 14/205* | (2006.01) | |

(52) U.S. Cl.
CPC ............ *C07K 17/08* (2013.01); *C07K 14/205* (2013.01); *C07K 14/245* (2013.01); *G01N 33/5436* (2013.01); *C07K 2319/03* (2013.01)

(58) Field of Classification Search
CPC .................................................... C07K 17/06
See application file for complete search history.

(56) References Cited

U.S. PATENT DOCUMENTS

| | | | | |
|---|---|---|---|---|
| 8,207,263 B2 * | 6/2012 | Popot | ...................... | C07K 17/06 435/4 |
| 2004/0157268 A1 * | 8/2004 | Kobilka | ............ | C07K 14/70571 435/7.2 |
| 2009/0275066 A1 * | 11/2009 | Popot | .................... | C07K 1/1077 435/18 |

FOREIGN PATENT DOCUMENTS

| | | | |
|---|---|---|---|
| WO | WO057780 | * | 7/2002 |
| WO | WO-2006069403 A2 | | 6/2006 |

OTHER PUBLICATIONS

Tanaka et al. 2010; Generation of single-chain Fvs against detergent solubilized recombinant antigens with a simple coating procedure. J. Biosci. Bioeng. 110(3): 374-376.*
Altschul, et al., "Basic Local Alignment Search Tool", J. Mol. Biol., 215:403, 1990 (8 pages).
Barton, "Protein secondary structure prediction", Current Opinion in Structural Biology, 5:372-376, 1995 (5 pages).
Basic Cell Culture Protocols, Third Edition, Methods in Molecular Biology vol. 290, Helgason and Miller, Eds., Humana Press, Totowa, New Jersey, 2004 (365 pages).
Butler, et al., "The physical and functional behavior of capture antibodies adsorbed on polystyrene", J. Immunol Methods, 150:77-90, 1992 (14 pages).
Cooke, et al., "Neural Differentiation Regulated by Biomimetic Surfaces Presenting Motifs of Extracellular Matrix Proteins", Journal of Biomedical Materials Research Part A, published online Aug. 3, 2009 (9 pages).
Esser, "Activity of Adsorbed Antibodies", Thermo Scientific Application Note 11b, 2010 (5 pages).
Fairman, et al., "The structural biology of β-barrel membrane proteins: a summary of recent reports", Current Opin. Struct. Biol., 21(4):523-531, Aug. 2011 (9 pages).
Gardas, et al., "Coating of Proteins to Polystyrene ELISA Plates in the Presence of Detergents", Journal of Immunological Methods, 106(2):251-255. Feb. 10, 1988 (5 pages).
Higgins, et al., "CLUSTAL: a package for performing multiple sequence alignment on a microcomputer", Gene, 73:237-244, 1988 (8 pages).
Huang, X., "On Global Sequence Alignment", Computer Applications in the Biosciences, 10(3):227-235, 1994 (9 pages).
International Search Report and Written Opinion issued by the European Patent Office as Searching Authority in International Application PCT/GB2015/050058, dated Jul. 6, 2015 (22 pages).
Johnsson, et al., "Comparison of Methods for Immobilization to Carboxymethyl Dextran Sensor Surfaces by Analysis of the Specific Activity of Monoclonal Antibodies", J. Molecular Recognition, 8:125-131, 1995 (7 pages).
Jones, "Protein Secondary Structure Prediction Based on Position-specific Scoring Matrices", Journal of Molecular Biology, 292:195-202, 1999 (8 pages).
Kim, et al., "Nontoxigenic Protein a Vaccine for Methicillin-Resistant *Staphylococcus aureus* Infections in Mice", Journal of Experimental Medicine, 207(9):1863-1870, 2010 (8 pages).
Koebnik, et al., "Structure and function of bacterial outer membrane proteins: barrels in a nutshell", Molecular Microbiology, 37(2):239-253, 2000 (15 pages).
Kyte, et al., "A Simple Method for Displaying the Hydropathic Character of a Protein", Jol. Mol. Bio., 157:105-132, 1982 (28 pages).
Le Brun, et al., "Monitoring the Assembly of Antibody-Binding Membrane Protein Arrays Using Polarised Neutron Reflection", European Biophysics Journal: Biophysics Letters, 37(5):639-645, Mar. 4, 2008 (7 pages).

(Continued)

*Primary Examiner* — Karen Cochrane Carlson
(74) *Attorney, Agent, or Firm* — Reichel Stohry Dean LLP; Natalie J. Dean

(57) ABSTRACT

The present invention provides a method for the functionalization of a polymeric surface with a protein by physical adsorption. The method enables a membrane spanning protein to be used as an anchor for proteins and/or peptides for display. Also provided are polymeric substrates for protein or peptide display, and related kits and methods of use.

29 Claims, 34 Drawing Sheets

Specification includes a Sequence Listing.

(56) References Cited

OTHER PUBLICATIONS

Le Brun, et al., "Self-Assembly of Protein Monolayers Engineered for Improved Monoclonal Immunoglobulin G Binding", International Journal of Molecular Sciences, 12(12):5157-5167, published online Aug. 15, 2011 (11 pages).
Leckband, et al., "An Approach for the Stable Immobilization of Proteins", Biotechnol. Bioeng., 37:227-237, 1991 (11 pages).
Nakanishi, et al., "Recent Advances in Controlled Immobilization of Proteins onto the Surface of the Solid Substrate and Its Possible Application to Proteomics", Current Proteomics, 5(3):161-175, 2008 (15 pages).
Pirovano, et al., "Chapter 19: Protein Secondary Structure Prediction", Methods in Molecular Biology—Data Mining Techniques for Life Sciences, Carugo and Eisenhaber, Eds., Humana Press, pp. 327-348, 2010 (22 pages).
Poon, et al., "Direct Demonstration of the Flexibility of the Glycosylated Proline-Threonine Linker in the Cellulomonas fimi Xylanase Cex through NMR Spectroscopic Analysis", J. Biol. Chem. 282(3):2091-2100, Jan. 19, 2007 (11 pages).
Shah, et al., "Self-Assembling Layers Created by Membrane Proteins on Gold", Biochemical Society Transactions, 35(3):522-526, Jun. 1, 2007 (5 pages).
Thompson, et al.,"CLUSTAL W: Improving the sensitivity of progressive multiple sequence alignment through sequence weighting, position-specific gap penalties and weight matrix choice", Nucleic Acids Res, 22(22):4673-4680, 1994 (8 pages).
Verhoeven, et al., "Differential Bacterial Surface Display of Peptides by the Transmembrane Domain of OmpA", PLOS ONE, 4(8):e6739, Aug. 25, 2009 (12 pages).
Yang, et al., "Cell Surface Display of Functional Macromolecule Fusions on *Escherichia coli* for Development of an Autofluorescent Whole-Cell Biocatalyst", Environmental Science & Technology, 42(16):6105-6110, published online Jul. 15, 2008 (6 pages).

\* cited by examiner

Fig. 11

SEQ ID NO: 2  OMPO    MHHHHHHSSGAPKDNTWYTGAKLGWSQYHDTGFINN                          NQPTHENQL
SEQ ID NO: 12 OMP154  MHHHHHHSSGAPKDNTWYTGAKLGWSQYHDTGFINN*TPTPTPTPTPQQSTNQPGTNQQPTPTPTPTP*NQPTHENQL

OMPO    QASAFSGYQVNPYVGFEMGYDWLGRMPYKGSVENGAYKAQGVQLTAKLGYPITDDLDIYTRLGGMVWRADTKSNVY
              OMP154  QASAFSGYQVNPYVGFEMGYDWLGRMPYK---------------AQGVQLTAKLGYPITDDLDIYTRLGGMVWRAGT

OMPO    GKNHDTGVSPVFAGGVEYAITPEIATRLEYQWTNNIGDAHTIGTRPDNGMLSLGVSYRFGQGEAAPVVAPAPAPAP
              OMP154  ---------GVSPVFAGGVEYAITPEIATRLEYQWTNN----------NGMLSLGVSYRFGQ---------------

Fig. 13

```
SEQ ID NO. 1   1 ATGCATCACCATCACCATCACTCGAGCTGTGCTCCGAAGATAACACCTGGTACACTGGT  60
SEQ ID NO. 2   1 M  H  H  H  H  H  S  S  C  A  P  K  D  N  T  W  Y  T  G    20

61 GCTAAACTGGGCTGGTCCCAGTACCATGACACTGGTTTCATCAACAACAATGGCCCGACC 120
              21 A  K  L  G  W  S  Q  Y  H  D  T  G  F  I  N  N  N  G  P  T   40

121 CATGAAAACCAACTGGGCGCTGGTGCTTTTGGTGGTTACCAGGTTAACCCGTATGTTGGC 180
              41 H  E  N  Q  L  G  A  G  A  F  G  G  Y  Q  V  N  P  Y  V  G   60

181 TTCGAATGGTACGACTGGTTAGGCGATATGCCGTACAAGCAGGTTGAAAACGGT 240
              61 F  E  W  Y  D  W  L  G  D  M  P  Y  K  Q  V  E  N  G   80

241 GCATACAAAGCTCAGGGCGTTCAACTGACCCGTAAACTGGGTTACCCAATCACTGACGAC 300
              81 A  Y  K  A  Q  G  V  Q  L  T  R  K  L  G  Y  P  I  T  D  D  100

301 CTGGACATCTACACTCGTCTGGGTGGCATGGTATGGCGTGCAGACACTAAATCCAACGTT 360
             101 L  D  I  Y  T  R  L  G  G  M  V  W  R  A  D  T  K  S  N  V  120

361 TATGGTAAAAACGACACCGGCGTTTCTCCGGTCTTCGCTGGCGGTGTTGAGTACGCG 420
             121 Y  G  K  N  D  T  G  V  S  P  V  F  A  G  G  V  E  Y  A  140

421 ATCACTCCTGAAATCGCTACCCGTCTGGAATACCAGTGGACCAACAACATCGGTGACGCA 480
             141 I  T  P  E  I  A  T  R  L  E  Y  Q  W  T  N  N  I  G  D  A  160

481 CACACCATCGGTACTCGTCCGGACAACGGCATGCTGAGCCTGGGTGTTCCTACCGTTTC 540
             161 H  T  I  G  T  R  P  D  N  G  M  L  S  L  G  V  P  T  V  F  180

541 GGTCAGGGCGAAGCAGCTCCAGTAGTTCGTCCGGCTCCAGCTCCGGCACCGTAA
             181 G  Q  G  E  A  A  P  V  V  R  P  A  P  A  P  A  P  *
```

Fig. 14

```
SEQ ID NO: 3   1 ATGCATCACCATCACCATCACTCGAGTGAAAACCAACTGGGCGCTGGTGCTTTTGGTGGT  60
                 ----;----|----(----|----;----|----;----|----(----|----;----|
SEQ ID NO: 4   1 M  H  H  H  H  H  S  S  E  N  Q  L  G  A  G  A  F  G  G    20

61 TACCAGGTTAACCCGTATGTTGGCTTTGAAATGGGTTACGACTGGTTAGGTCGTATGCCG 120
                 ----;----|----(----|----;----|----;----|----(----|----;----|
              21 Y  Q  V  N  P  Y  V  G  F  E  M  G  Y  D  W  L  G  R  M  P    40

121 TACAAGGCAGCGTTGAAAACGGTGCATACAAAGCTCAGGGCGTTCAACTGACCGCTAAA 180
                 ----;----|----(----|----;----|----;----|----(----|----;----|
              41 Y  K  G  S  V  E  N  G  A  Y  K  A  Q  G  V  Q  L  T  A  K    60

181 CTGGGTTACCCAATCACTGACGACCTGGACATCTACACTCGTTTGGGTGGCATGGTATGG 240
                 ----;----|----(----|----;----|----;----|----(----|----;----|
              61 L  G  Y  P  I  T  D  D  L  D  I  Y  T  R  L  G  G  M  V  W    80

241 CGTGCAGACACTAAATCCAACGTTTATGGTAAAACCAGGACATCGGGCGTTTCTCCGGTC 300
                 ----;----|----(----|----;----|----;----|----(----|----;----|
              81 R  A  D  T  K  S  N  V  Y  G  K  R  D  T  G  V  S  P  V   100

301 TTCGCTGGCGGTGTTGAGTACGCGATCACTCCTGAAATCGCTACCCGTCTGGAATACCAG 360
                 ----;----|----(----|----;----|----;----|----(----|----;----|
             101 F  A  G  G  V  E  Y  A  I  T  P  E  I  A  T  R  L  E  Y  Q   120

361 TGGACCAACAACATCGGTGACGCACACACCATCGGCACTCGTCCGGACAACGGCATGCTG 420
                 ----;----|----(----|----;----|----;----|----(----|----;----|
             121 W  T  N  N  I  G  D  A  H  T  I  G  T  R  P  D  N  G  M  L   140

421 AGCCTGGGTGTTTCCTACCGTTTCGGTCCGTGTACAGGTGATACCTGGTACACTGGTGCT 480
                 ----;----|----(----|----;----|----;----|----(----|----;----|
             141 S  L  G  V  S  Y  R  F  G  P  C  T  G  D  T  W  Y  T  G  A   160

481 AAACTGGGCTGGTCCCAGTACCATGACACTGGTTTCATCAACAACGGCCCAACCCAT 540
                 ----;----|----(----|----;----|----;----|----(----|----;----|
             161 K  L  G  W  S  Q  Y  H  D  T  G  F  I  N  N  G  P  T  H   180

541 ACGCGTGAGGAATTTTGA
                 ----;----|----;----
             181 T  R  E  E  F  *
```

Fig. 15

```
SEQ ID NO: 5    1  ATGCATCACCATCACCATCACTCGGAGTTCTCCGGTCTTCGCTGGCGGTGTTGAGTACGCG  60
                   ----|----|----|----|----|----|----|----|----|----|----|----|
SEQ ID NO: 6    1  M  H  H  H  H  H  H  S  S  P  V  F  A  G  G  V  E  Y  A    20

61  ATCACTCCTGAAATCGCTACCCGTCTGGAATACCAGTGGACCAACAACATCGGTGACGCA  120
                  ----|----|----|----|----|----|----|----|----|----|----|----|
              21  I  T  P  E  I  A  T  R  L  E  Y  Q  W  T  N  N  I  G  D  A    40

121  CACACCATCGGCACTCGTCCGGACAACGGCATGCTGAGCCTGGGTGTTTCCTACCGTTTC  180
                  ----|----|----|----|----|----|----|----|----|----|----|----|
              41  H  T  I  G  T  R  P  D  N  G  M  L  S  L  G  V  S  Y  R  F    60

181  GGTCCGTGTACAGGTGATACCTGGTACACTGGTGCTAAACTGGGCTGGTCCCAGTACCGT  240
                  ----|----|----|----|----|----|----|----|----|----|----|----|
              61  G  P  C  T  G  D  T  W  Y  T  G  A  K  L  G  W  S  Q  Y  R    80

241  GACACTGGTTTCATCAACAACAATGGCCCGACCCATGAAAAGCAACTGGGCGCTGGTGCT  300
                  ----|----|----|----|----|----|----|----|----|----|----|----|
              81  D  T  G  F  I  N  N  N  G  P  T  H  E  R  Q  L  G  A  G  A   100

301  TTTGGTGGTTACCAGGTTAACCCGTATGTTGGCTTTGAAATGGGTTACGACTGGTTAGGT  360
                  ----|----|----|----|----|----|----|----|----|----|----|----|
             101  F  G  G  Y  Q  V  N  P  Y  V  G  F  E  M  G  Y  D  W  L  G   120

361  CGTATGCCGTACAAAGGCAGCGTTGAAAACGGTGCATACAAAGCTCAGGGCTTCAACTG  420
                  ----|----|----|----|----|----|----|----|----|----|----|----|
             121  R  M  P  Y  K  G  S  V  E  N  G  A  Y  K  A  Q  G  V  Q  L   140

421  ACCGCTAAACTGGGTTACCCAATCACTGACGACCTGGACATCTACACTCGTCTGGGTGGC  480
                  ----|----|----|----|----|----|----|----|----|----|----|----|
             141  T  A  K  L  G  Y  P  I  T  D  D  L  D  I  Y  T  R  L  G  G   160

481  ATGGTATGGCGTGCAGACACTAAATCCAACGTTTATGGTAAAAACCACGACACCGGCACG  540
                  ----|----|----|----|----|----|----|----|----|----|----|----|
             161  M  V  W  R  A  D  T  K  S  N  V  Y  G  K  N  H  D  T  G  T   180

541  CGTGAGGAATTTTGA
                  ----|----|----|
             181  R  E  E  F  *
```

Fig. 16

```
SEQ ID NO: 7    1  ATGCATCACCATCACCATCACTCGAGCGGCATGCTGAGCCTGGGTGTTCCTACCGTTTC   60
                   ----|----|----|----|----|----|----|----|----|----|----|----|
SEQ ID NO: 8    1  M  H  H  H  H  H  S  S  G  M  L  S  L  G  V  S  Y  R  F   20

61  GGTCCGTGTACAGGTGATACCTGGTACACTGGTGCTAAACTGGGCTGGTCCCAGTACCAT  120
                   ----|----|----|----|----|----|----|----|----|----|----|----|
               21  G  P  C  T  G  D  T  W  Y  T  G  A  K  L  G  W  S  Q  Y  R   40

121  GACACTGGTTTCATCAACAACAATGGCCCGACCATGAAAACCAACTGGGCGCTGGTGCT   180
                   ----|----|----|----|----|----|----|----|----|----|----|----|
               41  D  T  G  F  I  N  N  G  P  T  M  K  T  N  W  A  L  V  L   60

181  TTCGGTGGTTACCAGGTTAACCCGTATGTGGGCTTTGAAATGGGTTACGACTGGTTAGGT  240
                   ----|----|----|----|----|----|----|----|----|----|----|----|
               61  F  G  G  Y  Q  V  N  P  Y  V  G  F  E  M  G  Y  D  W  L  G   80

241  CGTATGCCGTACAAAGGCAGCGTTGAAAACGGTGCATACAAAGCTCAGGGCGTTCAACTG  300
                   ----|----|----|----|----|----|----|----|----|----|----|----|
               81  R  M  P  Y  K  G  S  V  E  N  G  A  Y  K  A  Q  G  V  Q  L  100

301  ACCGCTAAACTGGGTTACCCAATCACTGACGACCTGGACATCTACACTCGTCTGGGTGGC  360
                   ----|----|----|----|----|----|----|----|----|----|----|----|
              101  T  A  K  L  G  Y  P  I  T  D  D  L  D  I  Y  T  R  L  G  G  120

361  ATGGTATGGCGTGCAGACACTAAATCCAACGTTTATGGTAAAAACCACGACACCGGCGTT  420
                   ----|----|----|----|----|----|----|----|----|----|----|----|
              121  M  V  W  R  A  D  T  K  S  N  V  Y  G  K  N  H  D  T  G  V  140

421  TCTCCGGTCTTCGCTGGCGGTGTTGAGTACGCGATCACTCCTGAAATCGCTACCCGTCTG  480
                   ----|----|----|----|----|----|----|----|----|----|----|----|
              141  S  P  V  F  A  G  G  V  E  Y  A  I  T  P  E  I  A  T  R  L  160

481  GAATACCAGTGGACCAACAACATCGGTGACGCACACACCATCGGCACTCGTCCGGACACC  540
                   ----|----|----|----|----|----|----|----|----|----|----|----|
              161  E  Y  Q  W  T  N  N  I  G  D  A  H  T  I  G  T  R  P  D  T  180

541  CGTGAGGAATTTTGA
                   ----|----|----|
              181  R  E  E  F  *
```

Fig. 17

SEQ ID NO: 9    1 ATGTCCTCGAGCGTAGACAACAAATTCAACAAAGAAaAAaAAAACGCaTTCTATGAGATC 60
SEQ ID NO: 10   1 M  S  S  S  V  D  N  K  F  N  K  E  R  N  A  F  Y  E  I  20

61 TTACATTTACCTAACTTAAACGAAGAACAACGAAACGCTTCATCCAAAGTTTAAAAGcg 120
              21 L  H  L  P  N  L  N  E  E  Q  R  N  A  F  I  Q  S  L  K  A  40

121 GcCCAAGCCAAAGCGCTAACCTTTTAGCAGAAGCTAAAAAGCTAAATGATGCTCAGGCG 180
              41 A  F  S  Q  S  A  N  L  L  A  E  A  K  K  L  N  D  A  Q  A  60

181 CCGAAAGTAGACGCGAATTCGAGCGAAAACCAACTGGGCGCTGGTGCTTTTGGTGGTTAC 240
              61 P  K  V  D  A  N  S  S  E  Q  L  G  A  G  A  F  G  G  Y  80

241 CAGGTTAACCCGTATGTTGGCTTTGAAATGGGTTACGACTGGTTAGGTCGTATGCCGTAC 300
              81 Q  V  N  P  Y  V  G  F  E  M  G  Y  D  W  L  G  R  M  P  Y  100

301 AAAGCTCAGGGCGTTCAACTGACCGCTAAACTGGGTTACCCAATCACTGACGACCTGGAC 360
             101 K  A  Q  G  V  Q  L  T  A  K  L  G  Y  P  I  T  D  D  L  D  120

361 ATCTACACTCGTTTGGGTGGCATGGTATGCGTGCAGACACTGGCCGTTCTCCGGTCTTC 420
             121 I  Y  T  R  L  G  G  M  V  N  R  A  D  T  G  V  S  P  V  F  140

421 GCTGGCGGTGTTGAGTACGCGATCACTCCTGAAATCGCTACCCGTCTGGAATACCAGTGG 480
             141 A  G  G  V  E  Y  A  I  T  P  E  I  A  T  R  L  E  Y  Q  W  160

481 ACCAACAACATCGGTGACAACGGCATGCTGAGCCTGGGTGTTTCCTACCGTTTCGGTCCG 540
             161 T  N  N  I  G  D  N  G  M  L  S  L  G  V  S  Y  R  F  G  P  180

541 ATCACAGGTGATACCTGGTACACTGGCGCTAAACTGGGCTGGTCCAGTACCATCACCAT 600
             181 I  T  G  D  T  W  Y  T  G  A  K  L  G  W  S  Q  Y  H  H  200

601 CACCATCACTGA
             201 H  H  H  *

Fig. 18

SEQ ID NO: 11    1 ATGCATCACCATCACCATCACTGGAGCGGTGCTCCGAAAGATAACACCTGGTACACTGGT   60
SEQ ID NO: 12    1  M  H  H  H  H  H  H  S  G  A  P  K  D  N  T  W  Y  T  G    20

61 GCTAAACTGGGCTGGTCCCAGTACCATGACACTGGTTTCATCAACAACACCCCTACCCCA  120
                21  A  K  L  G  W  S  Q  Y  H  D  T  G  F  I  N  N  T  P  T  P    40

121 ACGCCGACGCCTACTCCGCAACAGTCGACCAACCAACCCGGCACGAATCAACAGCCGACG  180
                41  T  P  T  P  T  P  Q  Q  S  T  N  Q  P  G  T  N  Q  Q  P  T    60

181 CCGACGCCAACGCCAACGCCAAATGGCCCGACCCATGAAAACCAACTGGGCGCTGGTGCT  240
                61  P  T  P  T  P  T  P  N  G  P  T  H  E  N  Q  L  G  A  G  A    80

241 TTTGGTGGTTACCAGGTTAACCCGTATGTTGGCTTTGAAATGGGTTACGACTGGTTAGGT  300
                81  F  G  G  Y  Q  V  N  P  Y  V  G  F  E  M  G  Y  D  W  L  G   100

301 CGTATGCCGTACAAAGCTCAGGGCGTTCAACTGACCGCTAAACTGGGTTACCCAATCACT  360
               101  R  M  P  Y  K  A  Q  G  V  Q  L  T  A  K  L  G  Y  P  I  T   120

361 GACGACCTGGACATCTACACTCGTCTGGGTGGCATGGTACGCGCAGACACTGGCGTT    420
               121  D  D  L  D  I  Y  T  R  L  G  G  M  V  R  A  D  T  G  V     140

421 TCTCCGGTCTTCGCTGGCGGTGTTGAGTACGCGATCACTCCTGAAATCGCTACCCGTCTG  480
               141  S  P  V  F  A  G  G  V  E  Y  A  I  T  P  E  I  A  T  R  L   160

481 GAATACCAGTGGACCAACAACATCAACGGCATGCTGAGCCTGGGTGTTTCCTACCGTTTC  540
               161  E  Y  Q  W  T  N  N  I  N  G  M  L  S  L  G  V  S  Y  R  F   180

541 GGTCAGTAAACGCGTGAGGAATTTGAAGATCCGCTGCTAACAAAGCCGAAGGAAGC      600
               181  G  Q  *

Fig. 19

```
SEQ ID NO: 13   1  ATGCATCACCATCACCATCACTCGAGTGAAAACCAACTGGCGGTGGTGCTTTTGGTGGT  60
                   ----:----|----:----|----:----|----:----|----:----|----:----|
SEQ ID NO: 14   1  M  H  H  H  H  H  H  S  S  E  N  Q  L  G  A  G  A  F  G  G   20

61  TACCAGGTTAACCCGTATGTTGGCTTTGAAATGGGTTACGACTGGTTAGGTCGTATGCCG 120
                   ----:----|----:----|----:----|----:----|----:----|----:----|
               21   Y  Q  V  N  P  Y  V  G  F  E  M  G  Y  D  W  L  G  R  M  P   40

121  TACAAAGCTCAGGGCGTTCAACTGACCGCTAAACTGGGTTACCCAATCACTGACGACCTG 180
                   ----:----|----:----|----:----|----:----|----:----|----:----|
               41   Y  K  A  Q  G  V  Q  L  T  A  K  L  G  Y  P  I  T  D  D  L   60

181  GACATCTACACTCGTTTGGGTGGCAATGTATGGCGTGACACTGGCGTTTCTCCGGTC 240
                   ----:----|----:----|----:----|----:----|----:----|----:----|
               61   D  I  Y  T  R  L  G  G  N  V  W  R  D  T  G  V  S  P  V   80

241  TTCGGTGGCGTTGAGTACGCGATCACTCCTGAAATCGCTACCCGTCTGGAATACCAG 300
                   ----:----|----:----|----:----|----:----|----:----|----:----|
               81   F  G  G  V  E  Y  A  I  T  P  E  I  A  T  R  L  E  Y  Q  100

301  TGGACCAACAACATCGGTGACAACGGCATGCTGAGCCTGGTGTTCCTACCGTTCGGT 360
                   ----:----|----:----|----:----|----:----|----:----|----:----|
              101   W  T  N  N  I  G  D  N  G  M  L  S  L  V  S  Y  R  F  G  120

361  CCGTTCTACAGCTGCATACCTGGTAACTGGTTCTAAACTGGCTGGTCCAGTACAACCAG 420
                   ----:----|----:----|----:----|----:----|----:----|----:----|
              121   P  C  T  G  D  T  N  Y  T  G  A  K  L  G  W  S  Q  Y  N  Q  140

421  TGATAA
                   ----:-
              141   *  *
```

Fig. 20

```
SEQ ID NO: 15   1 ATGCATCACCATCACCATCACTCGAGCGTAGACAACAAATTCAACAAAGAAAAAAAAAAC  60
                  ----|----|----|----|----|----|----|----|----|----|----|----|
SEQ ID NO: 16   1 M  H  H  H  H  H  S  S  V  D  N  K  F  N  K  E  E  E  N   20

61 GCATTCTATGAGATCTTRCATTRCCTAACTTAAACGAAGAACAACGAAACGCCTTCATC  120
                  ----|----|----|----|----|----|----|----|----|----|----|----|
               21 A  F  Y  E  I  L  H  L  P  N  L  N  E  E  Q  R  N  A  F  I   40

121 CAAAGTTAAAAGCGGCCCCAAGCCAAAGCGCTAACCTTTTAGCAGAAGCTAAAAAGCTA  180
                  ----|----|----|----|----|----|----|----|----|----|----|----|
               41 Q  S  L  K  A  A  P  S  Q  S  A  N  L  L  A  E  A  K  K  L   60

181 AATGATGCTCAGGCGCCGAAAGTAGACGCGAATTCGAGCACGTCGAGTGAAAACTAACTG  240
                  ----|----|----|----|----|----|----|----|----|----|----|----|
               61 N  D  A  Q  A  P  K  V  D  A  N  S  S  T  S  S  E  N  Q  L   80

241 GGCGCTGGTGCTTTTGGTGGTTACCAGGTTAACCCGTATGTTGGCTTTGAAATGGGTTAC  300
                  ----|----|----|----|----|----|----|----|----|----|----|----|
               81 G  A  G  A  F  G  G  Y  Q  V  N  P  Y  V  G  F  E  M  G  Y   100

301 GACTGGTTAGGTCGTATGCCGTACAAAGCTCAGGGCGTTCAACTGACCGCTAAACTGGGT  360
                  ----|----|----|----|----|----|----|----|----|----|----|----|
              101 D  W  L  G  R  M  P  Y  K  A  Q  G  V  Q  L  T  A  K  L  G   120

361 TACCCAATCACTGACGACCTGGACATCTACACTCGTTTGGGTGGCATGGTATGGCGTGCA  420
                  ----|----|----|----|----|----|----|----|----|----|----|----|
              121 Y  P  I  T  D  D  L  D  I  Y  T  R  L  G  G  M  V  W  R  A   140

421 GACACTGGCGTTTCTCCGGTCTTCGCTGGCGGTGTTGAGTACGCGATCACTCCTGAAATC  480
                  ----|----|----|----|----|----|----|----|----|----|----|----|
              141 D  T  G  V  S  P  V  F  A  G  G  V  E  Y  A  I  T  P  E  I   160

481 GCTACCCGTCTGGAATACCAGTGGACCAACAACATCGGTGACAACGGCATGCTGAGCCTG  540
                  ----|----|----|----|----|----|----|----|----|----|----|----|
              161 A  T  R  L  E  Y  Q  W  T  N  N  I  G  D  N  G  M  L  S  L   180

541 GGTGTTTCCTACCGTTTCGGTCCGTGTACAGGTGATACCTGGTACACTGGTGCTAAACTG  600
                  ----|----|----|----|----|----|----|----|----|----|----|----|
              181 G  V  S  Y  R  F  G  P  C  T  G  D  T  W  Y  T  G  A  K  L   200

601 GGCTGGTCCAGTACAACCAGTGATAA                                    
                  ----|----|----|----|----|                                     
              201 G  W  S  Q  Y  N  Q  *  *                                     
```

Fig. 21

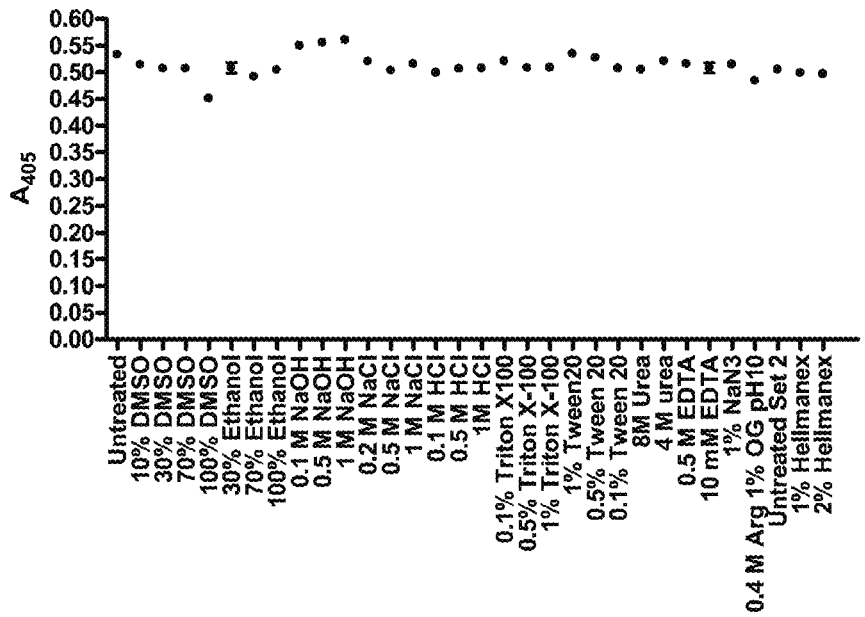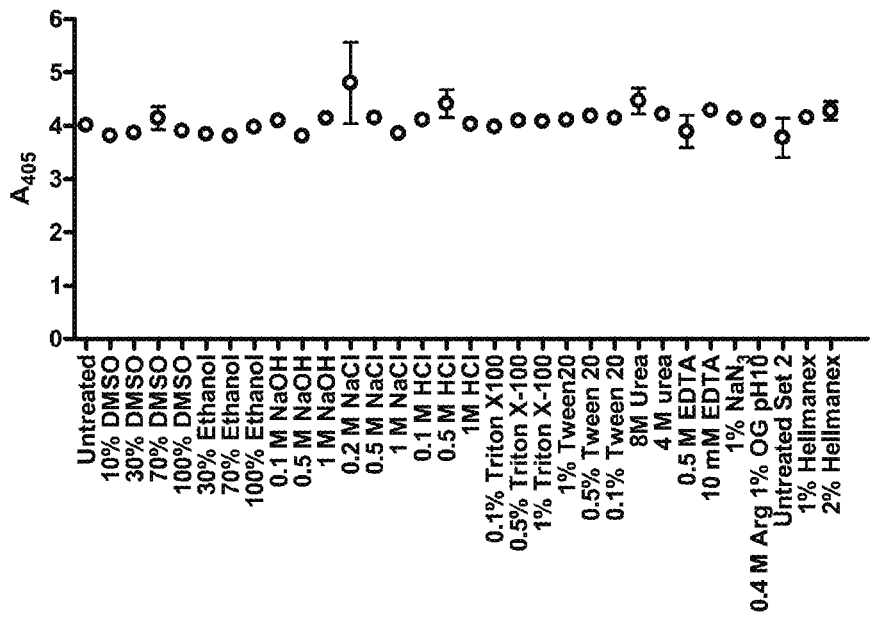
Fig. 30

PROTEIN COATED POLYMERIC SUBSTRATE

RELATED APPLICATIONS

This application is a National Stage Entry of PCT Application No. PCT/GB2015/050058 filed Jan. 14, 2015, which claims priority to GB Application No. 1400562.3, filed Jan. 14, 2014, the contents of which are incorporated herein by reference in their entirety.

The present invention relates to a method of immobilising a membrane spanning protein upon a polymeric substrate. The invention also relates to a polymeric substrate comprising a membrane spanning protein immobilised thereon, wherein the membrane spanning protein serves as an anchor for heterologous peptides and/or proteins. The invention also relates to uses of a coated polymeric substrate as described herein; and kits for making a coated polymeric substrate as described herein. Also provided are novel modified membrane spanning proteins as described herein, and the nucleic acid sequences encoding the same.

SEQUENCE LISTING

The instant application contains a sequence listing which has been submitted electronically in ASCII format and is hereby incorporated by reference in its entirety. Said ASCII copy, created on May 2, 2019, is named 2019_05_02_USSN15_111666_SequenceListing updated.txt, and is 39,992 bytes.

BACKGROUND

There is a need for simple, scalable methods for immobilization of proteins on a variety of materials for many applications e.g. diagnostic biosensors, immunodiagnostics, surgical implants, and bioprocessing media for affinity purification. In all applications it is critical to preserve the protein structure and function, and to orientate it correctly on the substrate for maximum efficiency of performance. There are numerous strategies for the immobilization of proteins on surfaces, as reviewed in Nakanishi, K. et al. ((2008) Current Proteomics 5: 161-175).

Physisorption is a commonly used method based on hydrophobic or ionic interactions of the protein with the surface. It is methodologically simple, but allows little quantitative or orientational control; it may alter the functional properties of the protein through unfolding, and reproducibility and efficiency are variable. This means that when bound, the proteins may not be oriented correctly for analyte binding or may be rendered wholly or partially denatured and non-functional. Many of these methods are complicated with many process steps and difficult to scale for mass manufacture. The methods also result in a large percentage loss of function of the protein concerned; for example less than 10% of antibody adsorbed to plastic ELISA plates is active whilst chemical coupling e.g. amine coupling results in 75-100% loss of activity (Butler J. E. et al. (1992) J Immunol Methods 150: 77-90; Butler J. E. et al. (1992) J Immunol Methods 150: 77-90; Esser, P. (2010) Thermo Scientific Application Note 11b; Johnsson, B. et al. (1995) J Molecular Recognition 8: 125-131).

Other methods of binding proteins to a surface include functionalization of the surface, for example via amination or carboxylation to allow covalent coupling of the proteins to the surface, or coating of the surface to mediate binding (e.g. streptavidin or biotin coating, polyLys coating, protein A coating, or nickel coated surfaces). Other methods include modification of the protein by addition of a binding tag (for example PhaF) which binds to bioplastic PHA derived from bacteria. Such methods based on covalent coupling provide a stable linkage, can be applied to a range of proteins and have good reproducibility. However, orientation may be variable, and chemical derivatisation may alter the function of the protein and requires a stable, interactive surface. Biological capture methods utilising a tag (such as hexahistidine/Ni-NTA or biotin/avidin) on the protein provide a stable linkage and bind the protein specifically and in reproducible orientation, but the partner reagent must first be immobilised adequately on the surface.

WO2002057780 describes the binding of protein to gold surfaces in self-assembled monolayers where the biologically functional moiety of the protein is correctly oriented and retains close to 100% of its activity. The technology involves the use of a modified variant of a β-barrel structured bacterial outer membrane protein (OMP) as a scaffold upon which other proteins and peptides of interest may be fused. The scaffold has intrinsic self-assembling properties on gold and is used as the anchor point for a fusion partner. The fusion partner is correctly oriented and retains function. The binding of the OMP to the gold surface relies upon modification of the protein to include a cysteine residue at an appropriate position in the OMP such that when the cysteine forms a covalent bond with the gold surface the protein is correctly orientated and directly coupled to the surface.

These methods have the disadvantage of requiring specific amino acids in the protein to mediate the reaction with the surface, modifications of the surface to accept covalent bonding from the cysteine, and the presence of amphiphilic molecules such as thiolipids or thioalkanes to stabilise the protein monolayer.

The applications requiring protein attachment to a surface are widespread, often requiring high protein density across a small area in order to maximise assay sensitivity. Plastic has many advantages for use as a substrate in protein based assays. However, the hydrophobic nature of plastic surfaces results in non-specific binding and denaturation of the proteins.

The present invention aims to overcome or ameliorate some of the problems associated with the prior art.

BRIEF SUMMARY OF THE DISCLOSURE

In a first aspect of the present invention, there is provided a method for immobilising a membrane spanning protein onto a polymeric substrate, the method comprising:
  i) providing a sample of a membrane spanning protein in detergent;
  ii) providing a polymeric substrate;
  iii) incubating the protein sample of i) with the polymeric substrate of ii); and
  iv) reducing the detergent concentration of the protein sample to 1× Critical Micelle Concentration (CMC) of the detergent or below;

wherein the protein becomes immobilised upon the substrate by physisorption.

The membrane spanning protein may anchor, or may be modified to anchor, a heterologous protein or peptide for display. Thus, when bound to the polymeric substrate, the membrane spanning protein is capable of displaying a protein or peptide anchored thereto, preferably in an oriented and functional manner. Thus, an anchored peptide and/or protein may be spatially removed from the surface of the polymeric substrate, to aid display. An anchored protein or peptide may be functional.

The membrane spanning protein comprises a head and a foot, the head and foot being spaced apart from one another by a body comprising one or more membrane spanning strands. By "anchors" means that the membrane spanning protein may comprise a heterologous peptide and/or protein in a loop at the head of the protein and/or at an N and/or C terminus at the head of the protein. By "modified to anchor" means that the membrane spanning protein is engineered to comprise an N and/or C terminus at the head of the protein, and/or one or more loops at the head of the protein. A heterologous peptide and/or protein may be provided at an engineered N and/or C terminus at the head of the protein, or in an engineered loop at the head of the protein, for display.

Thus, a the membrane spanning protein of the invention:
i) comprises a heterologous peptide and/or protein in a loop at the head of the protein;
ii) comprises a heterologous peptide and/or protein at an N and/or C terminus at the head of the protein;
iii) is engineered to comprise an N and/or C terminus at the head of the protein; and/or
iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

A spacer may be provided to create a spatial distance between the membrane spanning protein and the peptide and/or protein for display.

In an embodiment, a protein sample may comprise a detergent concentration of greater than 1×CMC, for example 1.5×CMC, 2×CMC, 2.5×CMC or higher. The detergent concentration of the protein sample is that which enables the protein to remain in solution. When protein is at high concentration e.g. 1.5 µM, it precipitates more easily in low detergent concentration; therefore the protein sample may have a detergent concentration of about 2×CMC solution in order to keep the protein soluble. Binding of the protein to the polymeric substrate is achieved by reducing the detergent concentration to 1×CMC or below. The detergent concentration is preferably maintained above 0×CMC in order to allow a period of time when the protein remains in solution and can bind to the substrate. The reduction may be achieved either by dilution or by dialysis, or any other suitable method.

The detergent concentration may be reduced prior to incubation of the protein sample with the polymeric substrate (step iii). Alternatively, the detergent concentration may be reduced on or after incubation with the polymeric substrate. Reduction of the detergent concentration of the protein enables binding of the membrane spanning protein to the polymeric substrate, wherein a peptide or protein anchored by the membrane spanning protein is preferably functional and orientated for display. Reduction of the detergent concentration enables binding of the membrane spanning protein to the polymeric substrate without requiring modification of the primary or secondary structure of the protein, or modification or functionalization of the substrate.

Dilution may comprise the addition of water, a buffer, or any other suitable diluent. A diluent may comprise a detergent, provided that the effect of mixing with the diluent is reduction in the concentration of the detergent of the protein sample to 1×CMC or below, preferably from 0.05×CMC to 1×CMC.

The step of reducing the detergent concentration of the protein sample may also effectively reduce the protein concentration, for example by increasing the volume of solution in which the protein is present. The dilution is sufficient to allow the protein to remain in solution for a sufficient period of time to bind the substrate, but the detergent concentration is low enough to allow physisorption of the protein to the polymeric substrate.

The method may further comprise washing the substrate.

The method may further comprise sterilising the substrate.

The detergent in which the protein is provided may be any ionic, non-ionic or zwitterionic detergent.

In a second aspect of the present invention, there is provided a polymeric substrate comprising a membrane spanning protein immobilised thereon, wherein the membrane spanning protein is immobilised upon the substrate by physisorption, and wherein the membrane spanning protein anchors, or is modified to anchor, a heterologous protein or peptide for display.

When bound (i.e. immobilised) to the polymeric substrate, the membrane spanning protein is capable of displaying a protein or peptide anchored thereto in an oriented and functional manner. Thus, a peptide and/or protein anchored by an immobilised membrane spanning protein may be spatially removed from the surface of the polymeric substrate, to aid display. An anchored protein or peptide may be functional.

The use of the membrane spanning protein overcomes problems in binding small peptides or proteins in a functional and oriented manner to a polymeric substrate, by serving as an anchor for such peptides or proteins. Thus, by displaying the peptide and/or protein on a membrane spanning protein which is immobilised on the polymeric substrate, the peptide and/or protein retains function, structure, and/or may be oriented in a manner which enables interaction with other components.

The membrane spanning protein may be defined as in relation to the first aspect. Thus, there may be provided a polymeric substrate comprising a membrane spanning protein immobilised thereon, wherein the membrane spanning protein is immobilised upon the substrate by physisorption, and wherein the membrane spanning protein:
i) comprises a heterologous peptide and/or protein in a loop at the head of the protein;
ii) comprises a heterologous peptide and/or protein at an N and/or C terminus at the head of the protein;
iii) is engineered to comprise an N and/or C terminus at the head of the protein; and/or
iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

A spacer may be provided to create a spatial distance between the membrane spanning protein and the peptide and/or protein for display.

The heterologous peptide and/protein may be functional.

Preferably, the membrane spanning protein is immobilised without a cross linking agent. Thus, the protein is immobilised upon the polymeric substrate without functionalization or modification of the surface to enable protein binding thereto. Cross linking agents include for example tags, binding partners for example biotin and streptavidin, protein A, etc.

Preferably, the membrane spanning protein does not comprise modification to a substrate binding domain, which may be provided in the foot of the protein. For example, the protein comprises its native primary and/or secondary sequence in a substrate binding domain. Preferably, the membrane spanning protein may not comprise modifications which enable covalent binding to the polymeric substrate.

Preferably, the membrane spanning protein is immobilised in the absence of a stabilizing agent such as a lipid, for example a lipid monolayer. Herein, a stabilising agent does not include a detergent.

Preferably, the membrane spanning protein is a β-barrel protein. Preferably, the membrane spanning protein is a porin, preferably an Outer Membrane Protein (OMP) of gram negative bacteria, more preferably OmpA or OmpF.

In a third aspect of the present invention, there is a provided a product comprising a polymeric substrate comprising a membrane spanning protein immobilised thereon, wherein the membrane spanning protein is immobilised upon the substrate by physisorption, and wherein the membrane spanning protein anchors, or is modified to anchor, a heterologous protein or peptide for display.

The polymeric substrate may be defined as in relation to the second aspect of the invention. Thus, there may be provided a product comprising a polymeric substrate comprising a membrane spanning protein immobilised thereon, wherein the membrane spanning protein is immobilised upon the substrate by physisorption, and wherein the membrane spanning protein:
  i) comprises a heterologous peptide and/or protein in a loop at the head of the protein;
  ii) comprises a heterologous peptide and/or protein at an N and/or C terminus at the head of the protein;
  iii) is engineered to comprise an N and/or C terminus at the head of the protein; and/or
  iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

In a fourth aspect of the present invention, there is provided a method of binding a component in a sample, the method comprising:
  i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
  ii) adding sample to the substrate;
  iii) maintaining the substrate with sample under conditions to allow binding of any component to the substrate.

The method may optionally comprise washing the substrate to remove any unbound material; detecting the presence or absence of bound component; and/or elution of any bound component. The method may be useful in screening of a sample for a component of interest, or purifying a component of interest from a sample, or immobilising a component of interest from a sample, for example for further reaction.

The method may comprise immobilising a membrane spanning protein on a polymeric substrate, as described herein.

The membrane spanning protein may be defined as in relation to the first and further aspects of the invention. The polymeric substrate may be defined as in the second and further aspects of the invention. Thus, the method may comprise:
  i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
  ii) adding sample to the substrate;
  iii) maintaining the substrate with sample under conditions to allow binding of any component to the substrate, wherein the polymeric substrate polymeric substrate comprises a membrane spanning protein immobilised thereon, wherein the membrane spanning protein is immobilised upon the substrate by physisorption, and wherein the membrane spanning protein:
  i) comprises a heterologous peptide and/or protein in a loop at the head of the protein;
  ii) comprises a heterologous peptide and/or protein at an N and/or C terminus at the head of the protein;
  iii) is engineered to comprise an N and/or C terminus at the head of the protein; and/or
  iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

In a fifth aspect, there is provided a method of mediating an interaction of an anchored peptide and/or protein with a component in a sample, the method comprising:
  i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
  ii) adding sample comprising a component to the substrate;
  iii) maintaining the substrate with sample under conditions to allow interaction of the component with anchored peptide and/or protein.

The membrane spanning protein may be defined as in relation to the first and further aspects of the invention. The polymeric substrate may be defined as in the second and further aspects of the invention. Thus, the method may comprise:
  i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
  ii) adding sample comprising a component to the substrate;
  iii) maintaining the substrate with sample under conditions to allow interaction of the component with anchored peptide and/or protein wherein the polymeric substrate polymeric substrate comprises a membrane spanning protein immobilised thereon, wherein the membrane spanning protein is immobilised upon the substrate by physisorption, and wherein the membrane spanning protein:
  i) comprises a heterologous peptide and/or protein in a loop at the head of the protein;
  ii) comprises a heterologous peptide and/or protein at an N and/or C terminus at the head of the protein;
  iii) is engineered to comprise an N and/or C terminus at the head of the protein; and/or
  iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

The component may be a cell, such that the peptide and/or protein may act as an effector for cell growth, development and differentiation. The peptide and/or protein may mediate an enzymatic reaction, or may act as a catalyst. For example, the peptide and/or protein may be a growth factor or signalling protein, or may induce cellular processes such as signalling pathways etc.

It is envisaged that a polymeric substrate of the present invention may anchor two or more different peptides and/or proteins via one or more membrane spanning proteins, for example to provide different functions simultaneously. Thus, for example, a combination of cell-attachment and growth factors may be provided on a substrate.

In a sixth aspect of the present invention, there is provided a surgical implant comprising a polymeric substrate comprising a membrane spanning protein immobilised thereon, wherein the membrane spanning protein is immobilised upon the substrate by physisorption, and wherein the membrane spanning protein anchors, or is modified to anchor, a heterologous protein or peptide for display.

The membrane spanning protein may be defined as in relation to the first and further aspects of the invention. The polymeric substrate may be defined as in the second and further aspects of the invention.

In a seventh aspect of the present invention, there is provided an incubation comprising a polymeric substrate, a membrane spanning protein, and detergent at a concentration of 1×CMC or below. This aspect of the invention relates to an intermediate in the production of a polymeric substrate of the invention. Any suitable method may be used for reduction of the detergent concentration, as described herein. It is envisaged that some of the membrane spanning protein may be immobilised on the substrate in the incubation. Preferably, the membrane spanning protein anchors, or is modified to anchor, a heterologous protein or peptide for display. Preferably, the membrane spanning protein becomes immobilised upon the substrate by physisorption. The membrane spanning protein may be defined as in relation to the first and further aspects of the invention. The polymeric substrate may be defined as in the second and further aspects of the invention.

In an eighth aspect of the present invention, there is provided a kit comprising a polymeric substrate, and a membrane spanning protein which anchors, or is modified to anchor, a heterologous protein or peptide for display. The membrane spanning protein may be defined as in relation to the first and further aspects of the invention. The polymeric substrate may be defined as in the second and further aspects of the invention.

In a ninth aspect of the present invention, there is provided a membrane spanning protein, which anchors, or is modified to anchor, a heterologous protein or peptide for display. The membrane spanning protein comprises a head and a foot, the head and foot being spaced apart from one another by one or more membrane spanning strands. By "anchors" means that the membrane spanning protein may comprise a heterologous peptide and/or protein in a loop at the head of the protein and/or a heterologous peptide and/or protein at an N and/or C terminus at the head of the protein. By "modified to anchor" means that the membrane spanning protein is engineered to comprise an N and/or C terminus at the head of the protein, and/or one or more loops at the head of the protein.

Preferably, the membrane spanning protein:
  i) comprises a heterologous peptide and/or protein in a loop at the head of the protein;
  ii) comprises a heterologous peptide and/or protein at an N and/or C terminus at the head of the protein;
  iii) is engineered to comprise an N and/or C terminus at the head of the protein; and/or
  iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein. A membrane spanning protein may be a protein as defined herein, for example an OMP protein as defined Table 7.

In a tenth aspect of the invention, there is provided a nucleic acid sequence encoding a membrane spanning protein, wherein the membrane spanning protein anchors, or is modified to anchor, a heterologous protein or peptide for display. The membrane spanning protein may be defined as in relation to the first and further aspects of the invention.

BRIEF DESCRIPTION OF THE DRAWINGS

Embodiments of the invention are further described hereinafter with reference to the accompanying drawings, in which:

FIG. 11 Alignment of OMP59 (SEQ ID NO: 17) and OMP171 (SEQ ID NO: 18). The extracellular loops and long C-terminus present on OMP59 but deleted from OMP171 are shown as dotted lines on the OMP171 sequence. The alpha helical spacer sequence is shown in italics with the mutated residues in OMP171 underlined. Two extra hydrophilic residues unique to the C-terminus of OMP171 are shown in bold and the cysteine residue is indicated by a *.

FIG. 13 Alignment of the amino acid sequences of OMP0 (SEQ ID NO: 2) and OMP154 (SEQ ID NO: 12). The elongated Loop 1 is shown in italics on the OMP154 sequence. The loops that were deleted in OMP154 and the truncated C-terminal tail are shown as a dotted line on the OMP154 sequence. The insertion site for small motifs is shown by the black triangle. The cysteine present in OMP0 has been mutated to a Glycine in OMP154 (underlined).

FIG. 14 shows the nucleic acid and amino acid sequence of OMP0 "wild-type" (SEQ ID NOS: 1 and 2) modified by removal of signal and C-terminal domain and addition of N-terminal his tag and cysteine at position 10. TM1 is residues 49-84; OL1 is residues 85-126; TM2 is residues 127-165; TM3 is residues 175-213; OL2 is residues 214-249; TM4 is residues 250-285; TM5 is residues 301-345; OL3 is residues 346-387; TM6 is residues 388-427; TM7 is residues 436-465; OL4 is residues 466-507; TM8 is residues 508-540; Cysteine is residues 28-30. TM—transmembrane strand (one pass through the membrane), OL—outer loop (extracellular loop).

FIG. 15 shows the nucleic acid (SEQ ID NO: 3) and amino acid (SEQ ID NO: 4) sequence of OMP 9 Loop 1 circular permutation.

FIG. 16 shows the nucleic acid (SEQ ID NO: 5) and amino acid sequence (SEQ ID NO: 6) of OMP 13 Loop 3 circular permutation.

FIG. 17 shows the nucleic acid (SEQ ID NO: 7) and amino acid sequence (SEQ ID NO: 8) of OMP 14 Loop 4 circular permutation.

FIG. 18 shows the nucleic acid (SEQ ID NO: 9) and amino acid (SEQ ID NO: 10) sequence of OMP 140 short loops, alpha helical spacer, c-terminal his tag, no cysteine.

FIG. 19 shows the nucleic acid (SEQ ID NO: 11) and amino acid sequence (SEQ ID NO: 12) of OMP 154 OMP0 with short loops and truncated C-term, but loop 1 elongated.

FIG. 20 shows the nucleic acid (SEQ ID NO: 13) and amino acid sequence (SEQ ID NO: 14) of OMP170 short loops, n-terminal his tag, cysteine at aa 122.

FIG. 21 shows the nucleic acid (SEQ ID NO: 15) and amino acid (SEQ ID NO: 16) sequence of OMP171, as 170 but with alpha helical spacer after his tag.

FIG. 30 shows data from immunoassay after washing with various agents as shown under the x-axis.

DETAILED DESCRIPTION

The present invention is based upon a different approach to the functionalization of a polymeric surface with a protein by physical adsorption. The method of the present invention enables the immobilisation of a membrane spanning protein onto a polymeric substrate without requiring covalent binding, and yet retaining the advantages of physisorption i.e. not requiring chemical modification of either the protein or the substrate, and not requiring the presence of stabilising compounds such as thiolipids and thioalkanes. The method of the present invention enables a membrane spanning protein to be used as an anchor for proteins and/or peptides for display. The anchored peptides and/or proteins, because they are not immobilised directly to the polymeric surface, retain function and/or structure, and are oriented for display. Thus, the membrane spanning proteins are bound to the substrate in a manner which enables their use as an anchor for display.

The present invention enables a membrane spanning protein to be immobilised upon a polymer substrate i) non-covalently (for example by Van der Waals interactions or ionic bonding); ii) without modification to a substrate binding domain (e.g. the foot) of the membrane spanning protein (e.g. modification to the primary or secondary structure) to include a substrate binding residue; iii) without functionalization or modification of the substrate to enable membrane spanning protein binding thereto; and/or iv) in the absence of a stabilizing agent such as a lipid. Further, the method of the present invention enables iv) the membrane spanning protein to anchor a peptide and/or protein for display, preferably such that the peptide and/or protein is functional and oriented for display. Preferably an anchored peptide and/or protein is directed away from the surface of the polymeric substrate, such that it is available for display.

Figure 2:
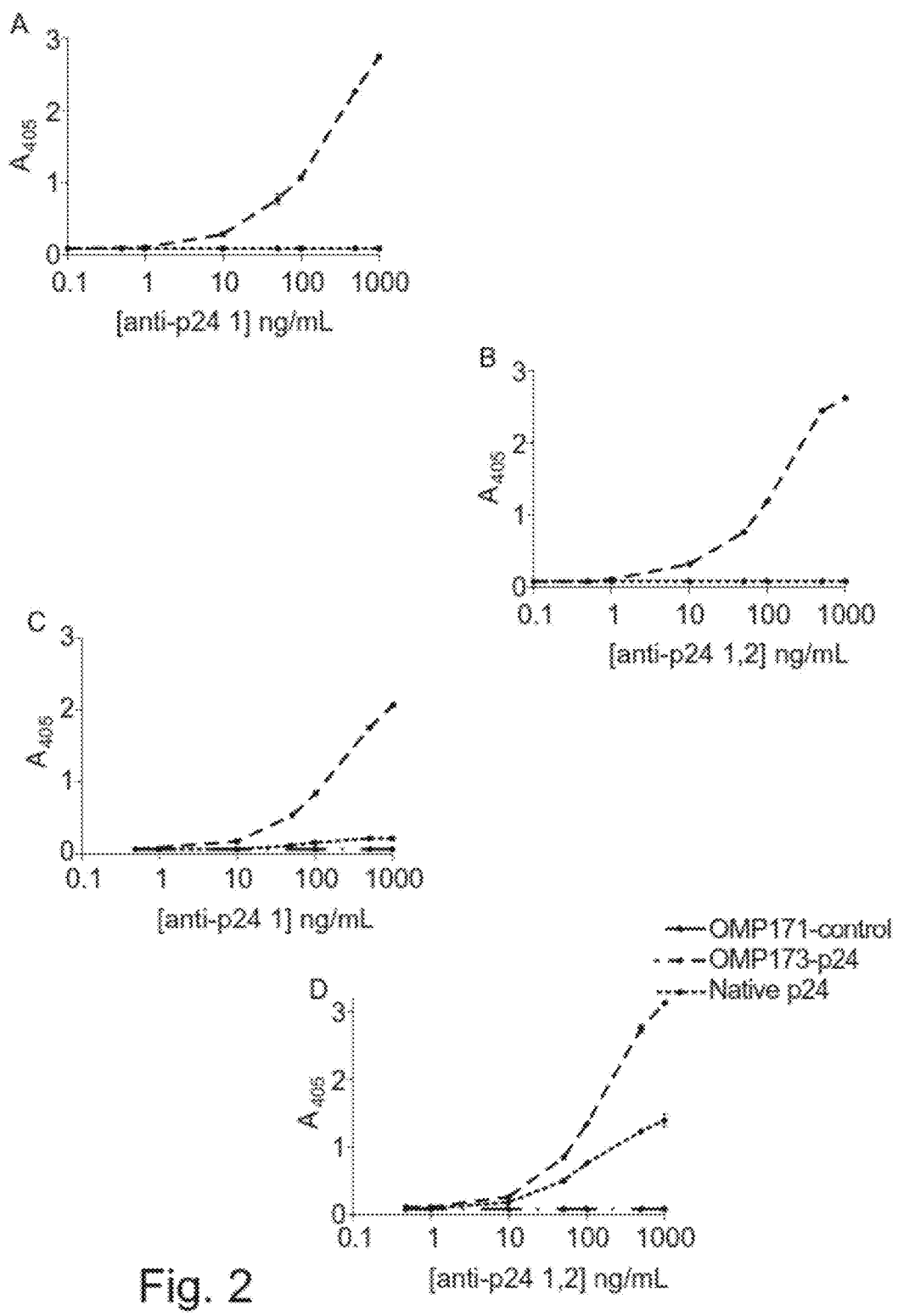
FIG. 2 shows the detection of immobilized P24 antigen and P24-fusion proteins on polystyrene plates (A, B) and Polysorp plates (C, D) with anti-HIV1-P24 (A, C) and Anti-HIV1/2 P24 (B, D) monoclonal antibodies.
Figure 3:
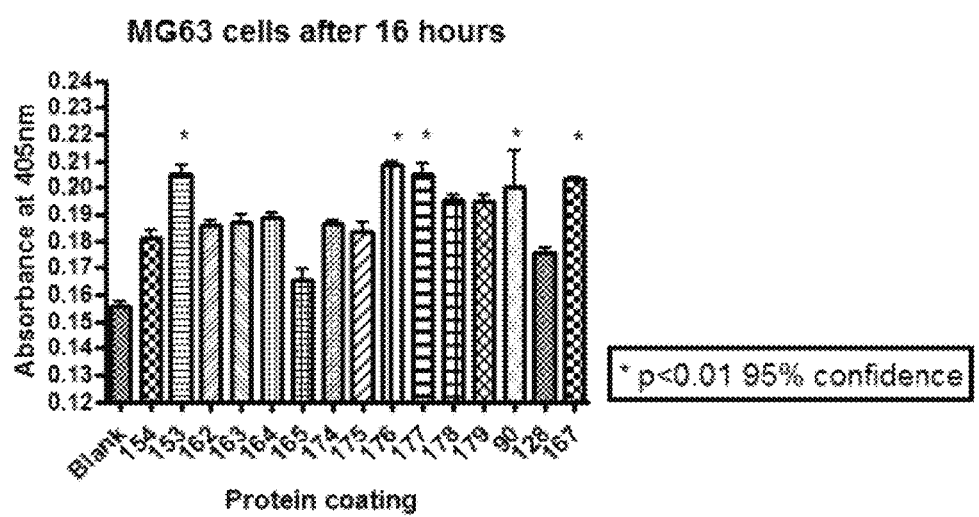
FIG. 3 shows the culture of MG63 bone cells on 96 well polystyrene plates coated with a range of OMP proteins displaying different biological properties. Blank represents an unmodified polystyrene well and OMP154 is the umodified scaffold protein, the addition of the 4 amino acids RGDS to OMP154 creates OMP153 a protein able to significantly enhance cell attachment.

The highly hydrophobic nature of membrane spanning proteins means that they precipitate in solution unless stabilized by high concentration of detergent (above 1×CMC, preferably 2×CMC). This also prevents such proteins from binding to surfaces. It was expected that the presence of detergent would prevent binding of the protein by hydrophobic interactions to a surface, and immobilization would be inefficient at best. Unexpectedly, however, it was found that dilution of the protein in low detergent concentration enabled immobilisation of the membrane spanning protein to a polymeric surface, in a manner which enabled functional and orientated display of an anchored peptide and/or protein. The immobilisation of membrane spanning proteins to a polymeric substrate according to the invention is distinct from immobilisation methods of the prior art. Surprisingly, the inventors have shown that the method of the invention results in a large increase in functionality when the protein is anchored to the surface by the membrane spanning protein. The great advantage of the present invention is exemplified by the fusion of an HIV antigen (the P24 protein) to a membrane spanning protein (the OMP170-type scaffold) as shown in FIG. 2.

Herein, a substrate comprises a surface to which a protein can be immobilised. The substrate may take any suitable form which can receive protein for immobilisation thereon. A substrate is preferably solid (i.e. not a gel or a liquid). A substrate may comprise a smooth surface or may be textured. The substrate, or a surface thereof, may be a mesh, a fibre, a bead, knitted or woven fabric, a well or micro-well plate, a tissue culture flask, or any other surface. The substrate comprises a polymer material, at least on a binding surface thereof. A substrate may comprise one or more different polymers. The substrate preferably comprises a bare polymer surface, meaning that it has not been coated with other material (e.g. proteins such as biotin or streptavidin) to aid binding of protein to the substrate or has not been functionalised, for example by amidation or carboxylation to mediate binding.

Polymers (polymeric substrates) may include plastic, silk and other proteinaceous fibres (for example hair, fur (keratin filaments), actin filaments, collagen filaments etc.), and graphene. A polymer may be a plastic. Plastics will be known to persons skilled in the art, and may include polyvinyl, polyethylene (PE) including for example polyethylene terephthalate (PET) and high-density polyethylene (HDPE) and low-density polyethylene (LDPE), polyacrylate (acrylic), polystyrene (PS) including high impact polystyrene (HIPS), silicone, polyester (for example polylactic acid (PLA) or polylactic coglycolic acid (PGLA)), polyurethane, polypropylene (PP), polyamide (nylon), Acrylonitrile butadiene styrene (ABS), Polyethylene/Acrylonitrile Butadiene Styrene (PE/ABS), bakelite, rubber, latex, polycarbonate (PC), Polycarbonate/Acrylonitrile Butadiene Styrene (PC/ABS) and polyvinyl chloride including for example polyvinylidene chloride (PVDC). The polymer may be natural or synthetic. In addition to the organic polymers of which the substrate is made, it may comprise non-organic or organic additives, from 10-50% by weight. A polymer may be biodegradeable.

A polymeric substrate may be hydrophobic, hydrophilic, or amphiphilic, or a combination of two or more thereof. In an embodiment, at least part of a polymeric substrate is hydrophobic.

Herein, a membrane refers to a cell membrane (also known as a plasma or cytoplasmic membrane) which surrounds a cell to separate the inside of the cell from the surrounding environment. The term membrane herein includes both inner and outer membranes. The term "extramembranous" refers to beyond the membrane, for example the extracellular, periplasmic or cytoplasmic space, as appropriate. Reference herein to periplasmic, cytoplasmic or extracellular is made with respect to the native positioning of the protein in the membrane. A cell membrane comprises a phospholipid bilayer, in which are embedded proteins to assist in communication and transport across the cell membrane. Thus, a protein which spans the membrane as defined herein is one which spans the phospholipid bilayer.

By a heterologous peptide or protein is meant that the peptide or protein moiety is not naturally associated with the product referred to, in nature. It may also be referred to as being foreign. Thus, an anchored peptide or protein sequence or a spacer may be heterologous to a membrane spanning protein, meaning that these peptides and/or proteins are not found in the membrane spanning protein in nature.

An engineered protein or nucleic acid sequence is one which has been modified by the hand of man, for example using recombinant protein or DNA technology to provide a nucleic acid sequence or protein which is different in primary, secondary or tertiary sequence to the native nucleic acid or protein sequence. A protein may be engineered to be spatially different to the native protein, which may also be described as an engineered secondary or tertiary structure.

In the present invention, a peptide or protein is a string of amino acids which are connected by peptide bonds. A protein may also be referred to as a polypeptide. Amino acids can be natural, non-natural, or a combination thereof. They may be L-amino acids or D-amino acids. Peptides and proteins may be chemically synthesised or purified from natural or recombinant sources. Proteins may have a secondary structure, and optionally a tertiary structure. Peptides on the other hand describe short, linear amino acid chains which generally lack secondary or tertiary structure. A peptide may comprise 2 or more amino acid residues. A protein may comprise 20 or more amino acid residues.

The term "nucleic acid sequence(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

Herein, a membrane spanning protein refers to a protein which in its native form resides in a cell membrane, and spans the membrane. A membrane spanning protein may also be referred to herein as an integral membrane protein or a transmembrane protein. A membrane spanning protein comprises a head and a foot which are spatially separated by a body comprising one or more membrane spanning strands. By "spanning" is meant that it extends across at least most of a lipid bilayer of a cell membrane. Thus, "membrane spanning" for the purposes of the present invention may include proteins which extend beyond the membrane boundaries or do not extend fully across the membrane boundaries. They may be distinguished from proteins which are able to travel across the membrane, but do not span a membrane as defined herein. A membrane spanning protein may be a single pass protein, meaning that it spans the membrane once, or may be a multi-pass protein, meaning that it spans the membrane one or more times. A membrane spanning protein may comprise one or more polypeptides. Typically, in its native form a membrane spanning protein may have role in transport across a cell membrane, ion exchange, cell signalling or communication, as a linker or enzyme and in membrane biogenesis.

By "pass" is meant a span of the membrane by the protein, or a substantial span of the membrane. Therefore, a single pass protein will span the membrane once, having an N terminus at either the head or foot, and a C terminus at the other. Therefore, a single pass protein will not have an extramembranous loop. A 2-pass protein will span the membrane twice, such that both N and C termini protrude from the head or foot. A 2 pass protein will comprise a single turn or loop. Alternatively, membrane spanning proteins may be referred to as X-stranded proteins, meaning that they have a defined number of strands which span the lipid bilayer. Herein, when referring to spans across the lipid bilayer, the terms "pass" and "strand" may be used interchangeably.

A membrane spanning protein will by its nature comprise a secondary structure, such that it is of a size and shape that it would reside in, and span the membrane as defined herein. The term therefore would not include short peptide sequences or linear sequences substantially lacking in secondary structure. Further, it is expected that a protein which is anchored to a membrane and which predominantly reside outside of the membrane would not be suitable for use in the present invention. Those skilled in the art will appreciate that the term "membrane-spanning" should not be interpreted strictly so as to exclude from this invention proteins extending partially beyond the membrane boundaries or extending only across the majority of the region between the membrane boundaries.

Membrane spanning proteins may comprise an alpha-helical structure. Such membrane spanning proteins may be found in the inner membranes of bacterial cells or the plasma membrane of eukaryotes, and sometimes in the outer membranes. The majority of membrane spanning proteins are alpha-helical. Membrane spanning proteins may alternatively comprise a beta-barrel configuration. Such proteins are found in the outer membranes of Gram-negative bacteria, the cell wall of Gram-positive bacteria, and outer membranes of mitochondria and chloroplasts. A multi-pass membrane spanning protein may comprise joins (for example turns) which link units of secondary structure (for example beta-strands). Such joins may be exposed to an aqueous phase, such as the cytosol periplasm or extracellular fluid.

A membrane spanning protein as described herein will aggregate in water.

A membrane spanning protein of the present invention may be naturally occurring or may be recombinant. A membrane spanning protein of the present invention may be engineered.

Preferred membrane spanning proteins for use in the present invention are those comprising a beta barrel structure. A beta barrel protein comprises a large beta-sheet, which adopts hollow, cylindrical structure or barrel shape. In the beta barrel, beta strands of the beta sheet are arranged in an anti-parallel manner, although some beta-barrel proteins have been identified comprising parallel strands. Hydrophobic residues may be oriented toward the exterior of the barrel, and hydrophilic residues facing the interior. Adjacent beta strands in a beta barrel may be adjacent in sequence (referred to as an "up and down beta barrel) or non-adjacent in sequence (referred to as a Greek key or a Greek-key barrel). A beta barrel protein may comprise any number of strands, for example from 8 to 22 beta strands. A beta barrel protein may comprise an even number of beta strands or an odd number of beta strands.

The adjacent strands or helices of a membrane spanning protein such as a beta barrel are each linked by a turn or a loop. A turn is an element of a secondary structure in a protein, where the amino acid chain changes direction. Turns include tight turns (including a, p, y, b and Trr-turns), multiple turns, hairpin turns. A turn is typically defined by the nature of the hydrogen bonding between residues of the turn. Turns, in particular β-turns, are typically found at the periplasmic end of a membrane spanning protein. A β-turn may also be referred to as a β-bend or a tight turn. A β-turn is a region of a protein where the polypeptide chain folds back on itself by about 180°. A turn may comprise 2 to 6 amino acid residues, more preferably 4 amino acids of a β-turn. A β-turn may comprise proline and glycine residues. Each turn in a beta-barrel protein may be numbered, for example T1, T2 and so on. Typically, turns are not extramembranous. A loop of a membrane spanning protein is typically longer than a turn, and may extend out of the membrane into the extramembranous space. Loops show high sequence variability, and generally lack secondary structure. A loop may be hydrophilic in nature, compared to a membrane spanning portion of a membrane spanning protein (e.g. a beta-strand or barrel structure) which may typically be hydrophobic in nature. Loops may be denoted L1, L2 etc.

A membrane spanning protein will typically comprise turns on one side of a membrane, and loops on the other. The end of the protein comprising mostly loops is referred to herein as the head of the protein. The end of the protein comprising mostly turns is referred to herein as the foot of the protein. In outer membrane proteins (i.e. of gram negative bacteria, chloroplasts and mitochondria), the loops are generally all found on one side of the protein which faces the extracellular space. Herein, this is the head of an outer membrane protein. The end comprising the turns and termini generally faces the periplasmic space, and is referred to herein as the foot of the protein. One or more alpha helical strands span the membrane, forming the body of the protein. In inner membrane protein or eukaryotic membrane proteins, loops may be found on the periplasmic or cytoplasmic facing end of the protein. The head is therefore defined herein as that end comprising extramembranous domains, for example the majority of loops. The foot is that which predominantly comprises turns, with less extramembranous domains than the other end of the protein.

The N and C termini are the ends of the protein, the C terminus comprising a free carboxyl (COOH) and the N terminus comprising a free amino (NH2) group. Herein, reference to the terminus includes reference to the end N or C residue, or the N or C terminal tail, or a part thereof. For a membrane spanning protein, a tail is that portion adjacent the N or C terminus which protrudes from the membrane i.e. it is the portion between a membrane spanning strand and an N or C terminal residue. The tail may comprise 2 or more amino acid residues, for example 2, 5, 10, 15, 20, 30, 40, 50 or more amino acid residues. The tails of the OmpA protein are shown in FIG. 14 as residues 17 to 48 (N terminal) and 180 to 207 (C terminal). In a preferred embodiment, engineering of the protein comprises permuating a loop of the protein to comprise the N and/or C terminal tail, preferably wherein the tail comprises the sequence of amino acids 17 to 48 (N terminal) and/or 180 to 207, or a part thereof.

The membrane spanning protein may be an integral membrane protein, preferably a beta-barrel protein, preferably a porin. The membrane spanning protein may be an ion-channel, a receptor for a ligand, an enzyme, or other.

Beta barrel proteins include porins, which natively function as transporters for ions and other small molecules which are unable to diffuse across a cell membrane. Loops are provided between beta strands. Porins include Outer Membrane Proteins (OMP) of Gram-negative bacteria, which are porins of the outer membrane. These include OmpA also known as Ompll, an eight-stranded-barrel, and OmpF which is a homotrimer of 16 stranded β-barrels (also referred to as Porin ompF Outer membrane protein 1 A). Other beta-barrel proteins include preprotein translocases present in mitochondria and chloroplasts; and lipocalins.

A membrane spanning protein for use in the present invention may be eukaryotic or prokaryotic. It may be bacterial. It may be plant-derived, or mammalian.

Membrane spanning proteins for use in the present invention will be available to persons skilled in the art. Examples of known beta barrel proteins for use in the present invention include: (Curr Opin Struct. Biol 2011 Aug. 21(4) 523-531):

8 stranded proteins: Ail of *Yersinia pestis* (PDB ID: 3QRA, 3QRC); NspA of *Neisseria meningitides* (1P4T); OmpA of *E. coli* (1QJP, lBXW, 1G90, 2GE4, 2JMM); OmpA of *Klebsiella pneumonia* (2KOL); OmpA of *Legionella pneumophila* (3LDT); OmpW of *Escherichia coli* (2F1V, 2F1T); OmpX of *Escherichia coli* (1QJ8, 1OORM, 1Q9F, 1Q9G, 1QJ9); OprG of *Pseudomonas aeruginosa* (2X27); PagP of *Escherichia coli* (1MM4, 1MM5, 3GP6, 1THQ); PagL of *Pseudomonas aeruginosa* (2ERV); TtoA of *Thermus* thermophiles (3DZM);

10 stranded proteins: OmpT of *Escherichia coli* (1178); OpcA of *Neisseria meningitides* (1K24, 2VDF); Pla of *Yersinia pestis* (2X55, 2X56);

12 stranded proteins: EspP of *Escherichia coli* (2QOM); EstA of *Pseudomonas aeruginosa* (3KVN); Hbp of *Escherichia coli* (3AEH); Hia of *Haemophilus* influenza (2GR8); LpxR of *Salmonella typhimurium* (3FID); IcsA of *Shigella flexneri* (3ML3); NalP of *Neisseria meningitidis*(1UYN, 1UYO); NanC of *Escherichia coli* (2WJQ, 2WJR); OMPLA of *Escherichia coli* (1QD5, 1QD6, 1FW2, 1FW3, 11ILD, 1ILZ, 11IMO); OprM of *Pseudomonas aeruginosa* (1WP1); TolC of *Escherichia coli* (1 EK9); Tsx of *Escherichia coli* (1TLW, 1TLY, 1TLZ); VceC of *Vibrio cholera* (1YC9);

14 stranded proteins: α-HL of *Staphylococcus aureus*, (7AHL, 3M2L, 3M3R, 3M4D, 3M4E); FadL of *Escherichia coli* (1T16, 3DWN, 2R4L, 2R4N, 2R40, 2R4P, 2R88, 2R89, 2R8A, 1T1L); FadL of *Pseudomonas aeruginosa* (3DWO); OmpG of *Escherichia coli* (2F1C, 21WV, 21WW, 2JQY, 2WVP, 2X9K); TbuX of *Ralstonia pickettii* (3BRY); TodX of *Pseudomonas putida* (3BSO, 3BRZ);

16 stranded proteins: FhaC of *Bordetella pertussis* (2QDZ, 2NJT); MspA (1UUN); Omp32 of Comamonas acidovorans (1 E54); Omp32 of *Delftia acidovorans* (2FGQ, 2FGR); OmpK36 of *Klebsiella pneumonia* (1OSM); OmpC of *Escherichia coli* (2J1N, 2J4U, 2XE1, 2XE2, 2XE3, 2XE5, 2XG6); OmpF of *Escherichia coli* (2ZFG, 1 BT9, 3FYX, 1GFM, 1GFN, 1GFO, 1GFP, 1GFQ, 3HW9, 3HWB, 1HXT, 1HXU, 1HXX, 3K19, 3K1 B, 1MPF, 3OOE, 2OMF, 2OPF); OprP of *Pseudomonas aeruginosa* (2O4V); PhoE of *Escherichia coli* (1 PHO); Gdp$^a$, *Rhodobacter capsulatus*, (2POR); Gdp$^a$, *Rhodopseudomonas* blastica, (1H6S, 1PRN, 2PRN, 3PRN, 5PRN, 6PRN, 7PRN, 8PRN); PorB, *Neisseria meningitidis*, (3A2R, 3A2S, 3A2T, 3A2U);

18 stranded pritein: BenF of *Pseudomonas fluorescens* pf-5, (3JTY); LamB, *Escherichia coli*, (1MPM, 1MPN, 1MPO, 1MPQ, 1AF6, 1MAL); LamB, of *Salmonella typhimurium*, (2MPR); OpdK of *Pseudomonas aeruginosa*, (2QTK); OprD, of *Pseudomonas aeruginosa* (2ODJ); or ScrY of *Salmonella typhimurium*, (1A0T, 1A0S, 1OH2);

19 stranded proteins: VDAC1 of *Mus musculus* (3EMN); VDAC1 of *Homo sapiens* (2K4T, 2JK4)

22 stranded proteins: BtuB of *Escherichia coli* (1NQE, 1NQF, 2GUF, 2GSK, 1NQG, 1NQH, 1UJW, 2YSU, 3M8B, 3M8D); Cir of *Escherichia coli* (2HDI, 2HDF); FauA of ordetella pertussis (3EFM); FecA, *Escherichia coli* (1KMO, 1PNZ, 1KMP, 1PO0, 1 PO3); FepA, *Escherichia coli* (1FEP); FhuA, *Escherichia coli* (1BY3, 1BY5, 1FCP, 2FCP, 1FI1, 2GRX, 1QFF, 1QFG, 1QJQ, 1QKC); FptA, *Pseudomonas aeruginosa* (1XKW); FpvA, *Pseudomonas aeruginosa* (2W75, 2O5P, 2W16, 2W6T, 2W6U, 21AH, 2W76, 2W77, 2W78, 1XKH); HasR, *Serratia marcescens* (3CSL, 3CSN, 3DDR); ShuA, *Shigella dysenteriae*, transporter (3FHH); and 24 stranded proteins: PapC of *Escherichia coli* (3FIP)

*Gdp—general diffusion porin. PDB IDs are provided in parenthesis. Further information for the PDB IDs listed can be found at the Protein Data Bank (www.rcsb.org).

Herein, the term "OMPXX" or "ORLAXX" where X is a numerical value have been used in relation to preferred scaffolds for use in the present invention. The terminology "OMP" is not limiting, and any suitable membrane spanning protein as defined herein may be modified as described in relation to any of the specific "OMPXX" or "ORLAXX" scaffolds to achieve the present invention. A preferred membrane spanning protein for use in the present invention is OMP0 of FIG. 14. Further preferred membrane spanning proteins are any one of the OMPXXs defined in Table 7.

Suitable membrane spanning proteins may be identified by analysis of the secondary structure. Protein secondary structure is defined by inter-residue hydrogen bonds, which result in the formation of a three-dimensional structure. Secondary structure includes α-helices, β-sheets, and various turns, depending upon the number and type of residues and the resulting bonding. Amino acids vary in their ability to form secondary structure, enabling the secondary structure of a peptide or protein to be predicted from the amino acid sequence. Any suitable prediction method may be used in the present invention to identify membrane spanning proteins, in particular beta-barrel proteins, from the primary structure (For example see: Barton (1995) Current opinion in structural biology Vol 5 p 372-376; Jones (1999) Journal of Molecular Biology Vol 292 p 195-202; Pirovano and Herringa (2010) Chapter 19: Protein Secondary structure prediction. In: Methods in Molecular Biology—Data Mining Techniques for the life sciences Eds. O Carugo and F Eisenhaber, Humana Press DOI 10.1007/978-1-60327-241-4). Such methods may also be used in the present invention during modification of a membrane spanning protein to predict folding, and therefore secondary structure, of a modified or synthetic protein sequence.

The Critical Micelle Concentration (CMC) is defined as the concentration of detergents above which micelles are spontaneously formed. At concentrations above the CMC, the detergents form complexes with lipophilic proteins. Below the CMC, detergents merely partition into membranes without solubilizing membrane proteins. The highly hydrophobic nature of the β-barrel core of membrane spanning proteins means that they precipitate in solution unless stabilized by high concentration of detergent (greater than 1×CMC). This also prevents such proteins from binding to surfaces.

The CMC will vary depending upon the detergent, for example SDS has a CMC of 7-10 mM; dodecylmaltoside has a CMC of 0.15 mM; octylglucoside has a CMC of 20-25 mM. Therefore, a detergent concentration for SDS of 7-10 mM is expressed as 1×CMC. A detergent concentration of 0.3 mM of dodecylmaltoside is expressed as 2×CMC, and so on.

The dilution factor will depend on the starting concentration of the protein and the detergent in the sample, and the required working concentration after dilution, and can be calculated by a person skilled in the art based using known dilution techniques to provide a CMC of 1×CMC or below, and a protein concentration where it retains solubility in that concentration of detergent for sufficient time to bind to the substrate. Whether or not a protein is soluble can readily be determined by a person skilled in the art, using available solubility assays. If a protein is insoluble it will precipitate and form a cloudy solution. The turbidity can be measured, for example by measuring the absorbance at 400 nm. Alternatively, a simple visual assessment can be used to detect a cloudy solution, indicating a protein which is no longer soluble.

The method of the present invention comprises reducing the detergent concentration of the protein sample of i) to 1×CMC or below. Preferably, the CMC is maintained above 0. Thus, the CMC may be reduced to from 0.05×CMC to 1×CMC, 0.075×CMC to 1×CMC, preferably 0.1×CMC to 1×CMC, or from 0.05×CMC to 0.9×CMC, 0.075×CMC to 0.9×CMC, preferably 0.1×CMC to 0.9×CMC, or from 0.05×CMC to 0.8×CMC, 0.075×CMC to 0.8×CMC, preferably 0.1×CMC to 0.8×CMC, or from 0.05×CMC to 0.7×CMC, 0.075×CMC to 0.7×CMC, preferably 0.1×CMC to 0.7×CMC, or from 0.05×CMC to 0.6×CMC, 0.075×CMC to 0.6×CMC, preferably 0.1×CMC to 0.6×CMC, or from 0.05×CMC to 0.5×CMC, 0.075×CMC to 0.5×CMC, preferably 0.1×CMC to 0.5×CMC, or from 0.05×CMC to 0.4×CMC, 0.075×CMC to 0.4×CMC, preferably 0.1×CMC to 0.4×CMC, or from 0.05×CMC to 0.3×CMC, 0.075×CMC to 0.3×CMC, preferably 0.1×CMC to 0.3×CMC, or from 0.05×CMC to 0.2×CMC, 0.075×CMC to 0.2×CMC, preferably 0.1×CMC to 0.2×CMC.

Preferably, these values are the detergent concentration of incubation mixture after the protein sample has been incubated with the polymeric substrate, although it is envisaged that the reduction in detergent concentration may be performed prior to incubation. Within these parameters, protein is prevented from precipitating into particulates in solution but instead is encouraged to attach to the polymeric substrate.

The appropriate dilution factor for any particular detergent may be determined readily by the skilled person, by testing the degree of saturation of a substrate with a membrane spanning protein anchored to a peptide and/or protein for display, and the solubility of the protein when incubated with the substrate. A suitable dilution factor provides at least 60%, 65%, 70%, 75%, 80%, 85%, 90% or at least 95% saturation of the substrate, and the protein remains in solution for at least 6 hours, preferably at least 8 hours, preferably at least 10 hours, and most preferably overnight (i.e. 12-24 hours). Saturation can be determined using a binding assay as described below.

Any suitable detergent may be used. Preferred detergents are those which stabilise the protein and prevent it from precipitating out of solution but allow the protein to interact with and bind to the substrate. Most preferably, the detergent may be selected from the group consisting of n-octylglucoside, dodecylmaltoside or Thesit. A detergent may be used alone, or in combination with one or more other detergents, preferably selected from those defined above. Preferably, the same detergent is used for both adding to the protein to provide a protein sample, and where detergent is used in the dilution in combination with a diluent.

Suitable buffers include phosphate buffers, Tris buffers, HEPES buffers, MES buffers, TES buffers, glycine buffers, acetate buffers, and any other buffers recognised as such by thoseskilled in the art.

The protein may be provided in solution, or as a dried product. Preferably, the protein is provided in a buffer, to which detergent is added. Where the protein is provided as a dried product, the method may comprise the additional step of dissolving the protein in a suitable buffer for example ROG-8 (50 mM Tris HCl, 0.1 mM EDTA, 1% OG).

In the method of the present invention, the detergent concentration of the protein sample may be reduced prior to incubation with the substrate. Additionally or alternatively, the detergent concentration may be reduced after incubation of the sample and substrate. In an embodiment, a diluent may be added to the substrate prior to incubation with the sample, which effectively reduces the detergent concentration of the sample upon incubation. Thus, step ii) may comprise adding a diluent to the polymeric substrate prior to incubating the substrate with the protein.

Thus, the method may comprise:
i) providing a sample of a membrane spanning protein in detergent;
ii) providing a polymeric substrate;
iii) adding a diluent to the polymeric substrate such that upon addition of protein sample there is provided a CMC of 1× or below;
iv) incubating the protein sample of i) with the polymeric substrate of iii);

wherein the protein becomes immobilised upon the substrate by physisorption.

The method may comprise:
i) providing a sample of a membrane spanning protein in detergent;
ii) providing a polymeric substrate;
iii) reducing the detergent concentration of the protein sample such that when incubated with the substrate the CMC is 1× or below;
iv) incubating the protein sample of iii) with the polymeric substrate of ii);

wherein the protein becomes immobilised upon the substrate by physisorption.

The protein may be added to the substrate in any suitable manner, for example it may be patterned (e.g. spotted).

The incubation is preferably carried out at room temperature or below (but above 0° C.). Preferably, the incubation is maintained for at least 6, preferably at least 8 hours, preferably at least 10 hours, and most preferably 12-24 hours. 24 hours is the optimum incubation period. In an embodiment, the method further comprises washing the substrate. The substrate may be washed with any suitable buffer, water, or solutions containing detergent or ethanol for example TBS, PBS, HEPES, TE, 70% ethanol, Tween, or deionised water, preferably sterile. Washing has the purpose of removing from the substrate any unbound material and any residual detergent. The substrate may be dried. It may further be sterilised. It may be packaged for sale.

Binding of the membrane spanning protein to the substrate can be determined using any suitable method in the art, including for example a binding assay. In a typical binding assay, the substrate may be incubated with a ligand (for example, IgG) which is able to bind a binding site of the membrane spanning protein, or to a peptide or protein anchored thereby. Any unbound ligand is removed by washing. Bound ligand may then be detected, either directly for example if it comprises a signal which can be measured, or indirectly, for example by using a second binding member specific for the ligand. The second binding member may be an antibody conjugated to enzyme or catalyst or other marker such as a fluorescent tag, and detection may be performed by incubation with a substrate and measuring the amount of signal produced. Any suitable signal may be used, many examples of which will be known and available to persons skilled in the art. Preferred signals are those that can be detected in the electromagnetic spectrum, such as chromophores and fluorophores, and enzyme substrate systems such as Horseradish peroxidase/TMB. Others will be known to persons skilled in the art. In the latter case, a binding member specific for the ligand may be bound to an enzyme, which catalyses the signal substrate to produce a colorimetric output. Preferred signals are those which employ an amplification system. Enzyme labels which can act on a substrate to produce chromophores are most preferred, e.g. Horseradish Peroxidase, alkaline phosphatase, beta galactosidase. Suitable substrates include TMB ABTS, OPD (for HRP), pNPP (for AP) and ONPG (for beta galactosidase).

The signal generated provides an indication of the degree of binding of the membrane bound protein to the substrate (i.e. the degree of saturation of the substrate) and whether any peptide or protein anchored thereto is not denatured, and is available for ligand binding. By saturated is meant that the maximum amount of protein is bound to the substrate, i.e. the substrate is fully occupied.

Thus, the method of the present invention provides a polymeric substrate comprising a membrane spanning protein immobilised thereon, wherein the membrane spanning protein is immobilised upon the substrate by physisorption, and wherein the membrane spanning protein anchors, or is modified to anchor, a heterologous protein or peptide for display.

By "immobilised" is meant that the protein is bound to the substrate, and remains bound after washing with water and/or a buffer containing detergent (for example Tween 20 at 0.05% (w/v)).

The membrane spanning protein may be provided on the substrate uniformly, or in a predetermined pattern, for example spotting. The present invention may also comprise a method of patterning a surface, comprising application of a membrane spanning protein of the invention to a substrate in a pattern. Preferably the pattern is pre-determined. Suitable methods of patterning a surface include lithography, inkjet, droplet injections and other methods known to persons skilled in the art.

Physisorption is physical adsorption of a compound to a surface, by non-covalent binding, for example van der waals interactions, hydrophobic interactions, charge interactions. Physisorption is not a chemical reaction between the protein and the substrate and is a non-covalent binding.

The present inventors have shown that, unexpectedly, a membrane spanning protein can be bound to a polymeric substrate by physisorption, and be capable of displaying an anchored peptide or protein. Thus, method of the invention enables a membrane spanning protein to be immobilised on a polymeric substrate, and to serve as an anchor to display a peptide and/or protein which may be functional and oriented for display. This binding of the membrane spanning protein to the substrate and its effectiveness as an anchor for peptides and/or proteins which are displayed in a functional and oriented manner means that the polymeric substrate has utility in a binding assay, as well as in other methodologies. The present invention therefore provides for the first time a polymeric substrate having a membrane spanning protein immobilised thereon, wherein the membrane spanning protein anchors, or is modified to anchor, a heterologous protein or peptide for display.

By anchor is meant that the membrane spanning protein may comprise a heterologous peptide and/or protein in a loop at the head of the protein and/or a heterologous peptide and/or protein at an N and/or C terminus at the head of the protein. Thus, the membrane spanning protein binds or is fused to a peptide or protein, which is displayed at the head of the membrane spanning protein. Thus, the membrane spanning protein and peptide and/or protein may be expressed as a single polypeptide chain.

By modified to anchor means that the membrane spanning protein is engineered to comprise an N and/or C terminus at the head of the protein, and/or one or more loops at the head of the protein, to enable it to display a peptide or protein when immobilised on the substrate. Thus, a peptide or protein may be displayed at the head of the protein. The modification enables an anchored protein or peptide to be is spatially removed from the surface of the substrate, and preferably is not sterically hindered by the membrane spanning protein or the surface. Thus, the anchored peptide or protein may be functional, and available for binding or other interaction. The engineering to provide an N and/or C terminus at the head of the protein may be achieved by circular permutation. This circular permutation means that the order of features of the protein is altered, without substantial impact on the overall tertiary structure of the protein. This may be achieved by engineering of the primary structure of the membrane spanning protein, using techniques available in the art. Thus, a membrane spanning protein may be engineered for an N and/or C terminus to extend from the head of the protein rather than the foot. A terminus, may be engineered to be provided in place of a loop, or adjacent to a loop, from within a loop. In an embodiment, an N or C terminal is engineered to extend from a loop. This may be achieved by engineering a loop to include an N and/or C terminus. Preferably, where both N and C termini are permutated, they may be engineered to be provided in the same loop. Thus, part of a loop may form an N terminus and part of a loop may for a C terminus. In such a situation, the loop is split, forming two domains rather than a loop structure. Thus, all or part of a loop may be replaced by an N and/or C terminus. Where the protein is OMP, the loop may be loop 1, 3 or 4. When immobilised on the substrate, the engineered terminus extends away from the surface of the substrate, providing an effective display site for a protein or peptide. A spacer may also be provided on the end of one or both termini, to further aid in display of an anchored peptide or protein thereto.

In an embodiment, a loop or N or C terminus may comprise a spacer sequence which serves to spatially distance a peptide or protein linked thereto from the substrate.

The heterologous peptide and/or protein is anchored for display by the membrane spanning protein. This means that is provided in the membrane spanning protein at a position such that when immobilised on the substrate, the peptide and/or protein is spatially distanced from the binding surface of the substrate, and as such is available for access by a component of interest (for example, in a binding reaction). Preferably, by anchored for display means that it is spatially distanced from steric hindrance with a membrane spanning protein which may prevent its interaction with a component of interest. Display of a heterologous peptide or protein can be ascertained using detection assays as described herein.

An anchored protein preferably retains any secondary structure, thus enabling it to retain function. By "retains its secondary structure" means that substantially all anchored protein (i.e. at least 70%, 75%, 80%, 85%, 90%, 95%, 96%, 97%, 98% or 99% of the bound protein) has its native, secondary structure. The native secondary structure of the protein is the folded structure under non-denaturing conditions. Whilst it is envisaged that some denaturation of the protein may occur upon binding, the overall secondary structure of the protein is substantially the same as the native secondary structure, and any denaturation does not have a significant effect on the overall folding of the protein, or its ability to bind a ligand. Secondary structure may also be referred to herein as conformation.

Where a heterologous peptide is inserted into a loop of the membrane spanning protein, it is preferably provided in a long loop, between membrane spanning strands. It is preferably provided toward the middle of the loop. The loop may be truncated prior to insertion of the peptide sequence. The loop may be lengthened in addition to insertion of the peptide sequence, for example by a spacer. Alternatively, the peptide sequence may be introduced into a native loop, so that it is lengthened compared to its native form. The modified loop may be longer or shorter than the native loop. When inserted into a loop, a heterologous peptide may be any suitable length, but preferably is too short to adopt a secondary structure which may interfere with the secondary structure of the membrane spanning protein. For example, suitable lengths may be from 3 to 70 amino acids. A heterologous peptide sequence may be provided in the N terminus, the C terminus, or both. A heterologous sequence (peptide or protein) may be independently provided at the end of a terminus, or within the sequence forming the terminus.

Preferably, it is provided at the N terminus, preferably at the end of the N terminus. A terminus may be engineered as described herein to provide an anchor (display) site for a peptide or protein.

By functional means that the peptide and/or protein retains one or more of its native functions, for example a binding function, a receptor function, a signalling function, or an enzymatic function.

The membrane spanning protein comprises a head and a foot, the head and foot being spaced apart from one another by a body comprising one or more membrane spanning strands. By "anchors" means that the membrane spanning protein may comprise a heterologous peptide and/or protein in a loop at the head of the protein and/or a heterologous peptide and/or protein at an N and/or C terminus at the head of the protein. By "modified to anchor" means that the membrane spanning protein is engineered to comprise an N and/or C terminus at the head of the protein, and/or one or more loops at the head of the protein. A heterologous peptide and/or protein may be provided at an engineered N and/or C terminus at the head of the protein, or in an engineered loop at the head of the protein, for display.

Thus, the membrane spanning protein may:
 i) comprises a heterologous peptide and/or protein in a loop at the head of the protein;
 ii) comprises a heterologous peptide and/or protein at an N and/or C terminus at the head of the protein;
 iii) be engineered to comprise an N and/or C terminus at the head of the protein; and/or
 iv) be engineered to comprise one or more loops at the head of the protein.

A heterologous peptide and/or protein may be provided at an engineered N and/or C terminus at the head of the protein, or in an engineered loop at the head of the protein, for display.

A heterologous peptide may be any peptide sequence, preferably a functional peptide sequence. A peptide sequence may consist of, be derived from or function as: a growth factors, a protein or peptide involved in protein-protein interaction or binding, an antibody binding motif, an epitope, an antigen, an allergen, an enzyme, a catalyst, a protein or a peptide involved in interactions or binding with DNA and/or carbohydrate; a protein or peptide involved in interaction or binding with small molecules, (drugs etc), cell binding, or cell signaling; an extracellular matrix protein; and indeed any other protein or peptide which may be desirable to display on a polymeric surface, for any purpose.

Specific examples of peptides and proteins for use in the invention include binding sites for a protein, for example a FLAG epitope (DYKDDDDK (SEQ ID NO: 19)); a growth factor such as FGF1 or FGF2, interleukin, thrombopoietin (TPO), stem cell factor (SCF), granular macrophage colony stimulating factor (GMCSF), Leukocyte inhibitory factor (LIF), sonic hedgehog (Shh); cell binding motifs for example of extramembranous matrix proteins such as integrin, collagen, laminin or fibronectin (e.g. as described in Table 3); extracellular matrix (ECM) protein motifs, for example RGDS, antigens (e.g HIV (e.g.) p24 antigen, BMP-2, vitronectin, osteopontin, Tenascin-C), and indeed any others known to persons skilled in the art. The peptide sequence may comprise any combination of two or more such peptide sequences.

Preferably, the peptide or protein may be a growth factor. The peptide or protein may be of any growth factor. A preferred growth factor is FGF1 or FGF2. In an embodiment, a growth factor may be anchored to the fusion protein, preferably directly to an N or C terminus of the membrane spanning protein. Preferably, a spacer may be provided between the membrane spanning protein and the growth factor. The provision of a spacer enables the growth factor and membrane spanning protein to refold independently upon expression. In addition, the spatial separation of the growth factor from the membrane spanning protein enables the growth factor to extend above the polymeric surface and to be functional as a growth factor without steric hindrance by the membrane spanning protein. The provision of a growth factor on a polymeric surface has particular application in cell culture techniques, for example to promote cell growth and/or differentiation.

The use of a spacer sequence in combination with a heterologous peptide and/or protein improves display of a peptide or protein, by orientating it away from the polymeric substrate. The provision of a spacer may also enable a heterologous protein and membrane spanning protein to refold independently upon expression, thus increasing the possibility of obtaining a functional heterologous peptide or protein anchored to the membrane spanning protein. The spatial separation provided by a spacer enables a heterologous peptide or protein to extend above the polymeric surface and to be functional without steric hindrance by the substrate or membrane spanning protein. A spacer may be provided in a loop, and/or at the end of an N and/or C terminus. A spacer may be in turn fused to a peptide or protein, for example for binding. Thus, the N and/or C terminus may be used for display of larger sequences, as the same restrictions regarding the effect of secondary structure are less likely to apply. A spacer may be heterologous to the membrane spanning protein and/or to the peptide and/or protein. A spacer may be an alpha helical sequence, anchored at one end to the free end of an N or C terminus, preferably an N terminus. A spacer may be provided in a loop, preferably adjacent to a heterologous peptide or protein. A spacer may be hydrophilic, rigid or semi rigid. A spacer may comprise any suitable primary or secondary sequence, but preferably lacks function such as signally, binding or other function. A preferred spacer may comprise an alpha helix, or a PT linker, for example as described in Poon et al, J Biol Chem 282: 2091-2011 2006, or a glycine-serine spacer linker for example PLrigid, 2aa GS linker, 6aa [GS]x linker, 10aa [GS]x linker, 10 aa flexible protein domain linker, 8 aa protein domain linker, Split fluorophore linker; Freiburg standard, 15 aa flexible glycine-serine protein domain linker; Freiburg standard, Short Linker (Gly-Gly-Ser-Gly) (SEQ ID NO: 20), Middle Linker (Gly-Gly-Ser-Gly)×2 (SEQ ID NO: 21), Long Linker (Gly-Gly-Ser-Gly)×3 (SEQ ID NO: 22), GSAT Linker, SEG, SEG-Linker, GSAT-Linker, Z-EGFR-1907Short-Linker, Z-EGFR-1907Middle-Linker, Z-EGFR-1907Long-Linker, Z-EGFR-1907_SEG-Linker, (Gly4Ser)3 Flexible Peptide Linker (SEQ ID NO: 23), Short Fusion Protein Linker: GGSG (SEQ ID NO: 20) with standard 25 prefix/suffix, Long 1 OAA Fusion Protein Linker with Standard 25 Prefix/Suffix, Medium 6AA Fusion Protein Linker: GGSGGS (SEQ ID NO: 24) with Standard 25 Prefix/Suffix. (www.parts.igem.org/Protein_domains/Linker). An alpha helical sequence may be provided for fusion to a heterologous peptide or protein, for example as shown in OMP173 of FIG. 12.

The present invention has the advantage that the membrane spanning protein is bound to the substrate in a manner which enables binding of a binding partner to a heterologous peptide or protein provided in an N and/or C terminus or a loop. This is in contrast to methods of the prior art in which the protein is typically bound to the substrate in a disorganised manner or requires additional agents to hold the proteins in place (for example, lipid monolayers), such that binding is possible. In the present invention, surprisingly, substantially all the anchored peptide and/or protein is orientated in a manner which enables it to be displayed for binding or interaction. Thus, in the present invention at least 70%, 75%, 80%, 85%, 90%, 95%, 96%, 97%, 98% or 99% of the anchored peptide and/or protein is oriented away from the polymeric substrate surface, and is displayed for binding or interaction. This can be ascertained using a binding assay or other techniques available in the art, as described herein, for example as described herein with regard to verification of binding to the substrate.

The N and/or C terminus of the membrane spanning protein may be modified. For example, one or both of the N or C terminus may be truncated, for example to increase hydrophobicity, or to introduce a heterologous sequence as described above.

Other modifications to the membrane spanning protein basic structure to improve binding properties may be made. These include: the deletion of large internal or external domains that are not integral to the membrane; the truncation of one or more loops to reduce the hydrophilicity of the barrel; elongation of one or more loops, for example with hydrophilic spacers to allow the insertion and display of proteins on the loops; circular permutation to alter the spatial positioning of the N- and/or C-termini; introduction of purification tags (e.g. his tags, FLAG-tags and others). One or both of the N or C terminuses may be modified to include one or more amino acid deletions, substitutions or insertions, to alter the structural and/or functional properties thereof. One or more loops of the membrane spanning protein may be engineered, as described herein.

It may be desirable to increase the hydrophobicity of a protein, for example by truncating one or more loops of the protein, which are typically hydrophilic. This may serve to improve binding of the protein to a hydrophobic substrate, without the requirement for functionalization of the plastic surface, or modification of the protein to introduce binding moieties such as specific amino acids for covalent binding to the substrate. The shortening of one or more of the long, hydrophilic loops of a membrane spanning protein further has the advantage of reducing non-specific binding from serum or other matrix proteins, in an assay.

The hydrophobicity of a protein is a measure of the tendency of a protein to aggregate and repel water. The hydrophobicity of a protein is a factor of the amino acids present in the primary structure, but also a factor of the secondary structure. Therefore, different parts of a protein may be hydrophobic or hydrophilic. Various methods exist for categorising the hydrophobicity of amino acid residues, including chromatographic methods, accessible surface area methods, partitioning methods. The value may be referred to as the hydropathy index. A hydropathy plot or X ray structure analysis may be used to predict the hydrophobicity over the length of an amino acid sequence. The scale is based upon the hydrophobic and hydrophilic properties of the 20 amino acids. A moving "window" of from 5 to 20 amino acids determines the summed hydropathy at each point in the sequence (Y coordinate). These sums are then plotted against their respective positions (X coordinate) (Kyte and Doolittle Jol Mol. Bio. (1982) 157 105-132). In embodiments where it desired to alter the hydrophobicity of a membrane spanning protein, for example in order to aid binding of the protein to a polymeric substrate, a hydropathy plot may be useful in predicting the hydrophobicity of a loop before and after any modification, to determine whether a proposed modification results in the desired change in hydrophobicity. In embodiments for example it may be desirable to increase the hydrophobicity of a protein, for example by truncating one or more loops of the protein, which are typically hydrophilic.

Membrane spanning proteins for use in the present invention are those which comprise at least one loop, and therefore span the membrane at least twice. A membrane spanning protein for use in the present invention may comprise two or more loops. Each loop of a membrane spanning protein may differ in length and structure from one or more other loops of the protein. Where it is desired to modify a protein, any one more loops may be truncated as described herein for example to increase the hydrophobicity of the protein, and enable directed immobilisation to a hydrophobic substrate. The number of loops which are truncated will depend upon the protein and the extent to which hydrophilicity resulting from the loops is desired to be reduced. This may be a factor of the specific sequence and length of any particular loop. Using primary sequence analysis, and optionally methods such as X ray crystallography and hydropathy plotting, a skilled person can assess the predicted hydrophilic/hydrophobic nature of an loop and of a modified membrane spanning protein to determine the appropriate loop(s) to be truncated, and by how many amino acids. Methods are available in the art for determining hydrophobicity including solvent phase partitioning, RPLC, TLC. A preferred method includes analysis of the X-ray structures and predictive hydropathy plots (Kyte and Doolittle) to make decisions when engineering the protein.

The number of loops to be truncated may be defined by number, based on the native configuration of the protein with the C terminus residing on the periplasmic side. In a 2 or 3 or more pass protein, 1 or more loops may be truncated. In a preferred embodiment, all but one of the loops may be truncated. The numbering of the loops herein is based upon the native C terminus being on the cytosolic side.

By "truncated" is meant that the loop is reduced in length compared to its native form. A reduction in length is achieved by deletion of one or more amino acid residues from the loop. The extent to which a loop is truncated will depend upon factors such as the degree of hydrophobicity to be achieved by modification of the protein, and the impact of the deletion on the tertiary structure of the protein. Thus, by "truncated" means that all or part of a loop may be removed. Preferably, a modified membrane spanning protein according to the invention retains its native tertiary structure. Thus, where the membrane spanning protein is a beta-barrel protein, the modified protein preferably retains a beta-barrel tertiary confirmation. Thus, preferably the shortening or removal of one or more loops does not significantly impact the final tertiary structure of the protein compared to its native form. Each loop in a protein may be modified differently to one or more other loops in the protein, or in the same way as one or more other loops in the protein. Preferably, a loop is truncated to a length which enables it to connect transmembrane strands without constriction and preferably without altering of the tertiary structure of the protein. Preferably, a loop is truncated such that it does not extend into the aqueous phase outside of the membrane.

The truncation of one or more loops of a membrane spanning protein as described herein serves to increase the hydrophobicity of the protein, and also to reduce non-specific binding to the protein. In the presence of detergent, the protein is able to bind to a hydrophobic substrate. Thus, the protein is immobilised directly to the polymeric substrate, without requirement for tags, functionalization or linker sequences. Preferably, the head is directed away from the polymeric substrate, and as such is available for binding, for example in a screening assay. Preferably, when immobilised to a substrate the protein maintains its secondary and tertiary structure, and preferably is correctly orientated for display of a binding site. Preferably, the protein is functional. Preferably, the protein is orientated for, and capable of, binding to an analyte or ligand. Preferably, the protein is organised non-randomly on the surface of the substrate, such that a plurality of proteins are orientated in substantially the same manner. Preferably, the protein is positioned on the substrate such that any functional sites, such as binding sites, are exposed, preferably directed toward the solution/reaction surface.

A loop which is retained in the modified membrane spanning protein may be modified to include hydrophilic residues, either by insertion or substitution. The purpose of introducing hydrophilic residues into the loop is to create repulsion from a hydrophobic substrate and position the loop and its active content above the surface such that it is accessible. Such hydrophilic residues may be part of a spacer peptide or in addition thereto.

The protein may be modified to include a tag, for example a polyhistidine tag. A polyhistidine tag may comprise 6 or more histidine residues. The tag may be referred to herein as a His6 tag, a 6×his tag or a hexa-his tag. Other suitable tags include FLAG, c-myc or other small affinity tag. A tag may be provided on a C or N terminus. The terminus may be modified as described herein. The tag may be provided on a truncated C or N terminus.

The protein may be modified to remove one or more native cysteine residues, in particular in those parts of the protein which are to contact the polymeric substrate. Thus, one or more of the loops may be modified to remove (by deletion or substitution) one or more native cysteine residues. Such a modification may be appropriate for proteins which are to be bound to plastic substrates, and are not required to exhibit dual functionality of binding to plastic and other substrates such as gold.

In addition to the modifications described above, a membrane spanning protein may be modified to include one or more conservative substitutions of one or several amino acids without significantly altering the biological activity and/or tertiary structure of the protein. A person skilled in the art will be aware of methods for making such amino acid substitutions.

OmpA is an 8-pass protein, meaning that it comprises 8 beta strands which form a barrel shape and each span the membrane.

In an embodiment, OmpA may be modified to comprise 3 truncated extracellular loops. Preferably, each loop is truncated to the length of a turn, preferably a beta-turn of 4 amino acids. In an embodiment, 3 of the 4 extracellular loops are truncated. Loop 1 is retained and modified with a PT linker and hydrophilic amino acids (See FIG. 14, SEQ ID NO: 1 and 2). In an embodiment, the remaining loop is lengthened. Preferably, the extracellular loop is lengthened by the introduction of hydrophilic residues. Preferably, the loop is lengthened by the introduction of a peptide spacer sequence and/or hydrophilic residues. This protein is referred to herein as OMP154. Variants of OMP154 are described in Table 3.

A modified membrane spanning protein may comprise a FLAG epitope (DYKDDDDK; SEQ ID NO: 19) in extracellular loop 1. An OmpA modified in this manner referred to herein as OMP5.

A modified membrane spanning protein may comprise the YIGSR motif from laminin in extracellular loop 1 (SEQ ID NO: 27). This protein is referred to herein as OMP36.

A modified membrane spanning protein may comprise i) all extracellular loops truncated, preferably each truncated to the length of a beta-turn; ii) the N and C termini positioned on the extracellular end (head) of the protein; iii) the N terminus modified to include an alpha helical spacer sequence; iv) a cysteine residue to enable binding of the protein to a gold surface. This protein is able to bind gold and plastic substrates. Preferably, the protein backbone is circularly permuted beta barrel of OmpA (FIG. 14; SEQ ID NOs 1 and 2). Preferably, the alpha helical spacer is a mutated form of the *S. aureus* Protein A B domain which does not bind to IgG (the sequence of which is disclosed in Kim et al. (2010) Journal of experimental medicine Vol. 207 p 1863-1870). This protein is referred to herein as OMP171. A version lacking the alpha helical spacer is referred to herein as OMP170. A modified version of such a membrane spanning protein is provided wherein a protein is fused to the spacer. In an embodiment, the protein is HIV antigen p24, and the protein is referred to herein as OMP173.

Figure 11:
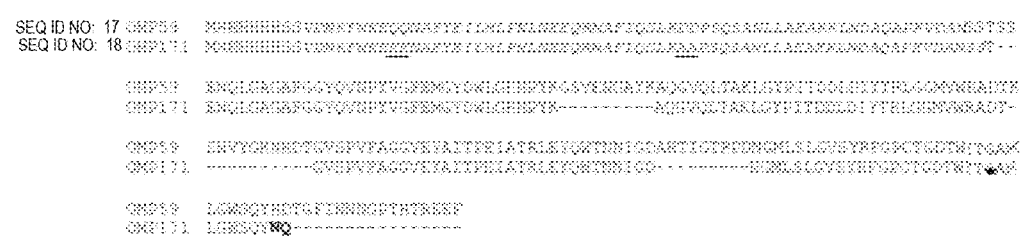

In an embodiment, a modified membrane spanning protein comprises i) all extracellular loops truncated, preferably each truncated to the length of a beta-turn; ii) the N and C termini positioned on the extracellular end (head) of the protein; iii) the N terminus modified to include an alpha helical spacer sequence; iv) a His tag provided on the C terminus, v) the protein is free of cysteine residues. These modifications allow the fusion of large growth factors that contain numerous cysteine residues and help ensure that only full length expressed proteins contain the His-tag. Preferably, the protein backbone is a circularly permuted beta barrel of OmpA. This protein is referred to herein as OMP140. Variants of OMP140 are described in Table 4. OMP90 and 128-comprise FGF1 and 2 in an OMP59 scaffold (OMP59 is OMP9 with an alpha-helical spacer, is shown in FIG. 11; SEQ ID Nos 17 and 18).

In an embodiment, a modified membrane spanning protein comprises i) the N and C termini positioned on the extracellular end of the protein; iii) the N terminus truncated and fused to the IgG binding domain of Protein A of *Staphylococcus aureus*. These modifications allow the fusion of the protein to the Fc region of an antibody to the protein. This protein is referred to herein as OMP18.

In an aspect of the present invention, there is provided a membrane spanning protein which anchors, or is modified to anchor, a heterologous protein or peptide for display. The membrane spanning protein comprises a head and a foot, the head and foot being spaced apart from one another by one or more membrane spanning strands. By "anchors" means that the membrane spanning protein may comprise a heterologous peptide and/or protein in a loop at the head of the protein and/or a heterologous peptide and/or protein at an N and/or C terminus at the head of the protein. By "modified to anchor" means that the membrane spanning protein is engineered to comprise an N and/or C terminus at the head of the protein, and/or one or more loops at the head of the protein.

Preferably, the membrane spanning protein:
  i) comprises a heterologous peptide and/or protein in a loop at the head of the protein;
  ii) comprises a heterologous peptide and/or protein at an N and/or C terminus at the head of the protein;
  iii) is engineered to comprise an N and/or C terminus at the head of the protein; and/or
  iv) is engineered to comprise one or more loops at the head of the protein.

A heterologous peptide and/or protein may be provided at an engineered N and/or C terminus at the head of the protein, or in an engineered loop at the head of the protein, for display. Preferably, the membrane spanning protein comprises a heterologous peptide and/or protein.

The present invention includes variant membrane spanning proteins to a membrane spanning protein of the invention. Preferably, variant proteins may differ in the primary sequence, but retain substantially identical secondary tertiary structure to the modified membrane spanning protein of the present invention. By substantially identical means that the protein shares at least 40%, preferably 50%, 60%, 70%, 80%, 90%, 95%, 96%, 97%, 98% or 99% sequence identity over a suitable window, for example of 10 to 500 amino acids. Peptide or protein sequence identity can be determined by methods available in the art, for example using BLASTP (from the BLAST suite of programs, version 2.2.5 [November 2002]) in bl2seq, which is publicly available from NCBI (ftp://ftp.ncbi.nih.qov/blast/); EMBOSS-needle (available at www.ebi.ac.uk/emboss/align/) and GAP (Huang, X. (1994) On Global Sequence Alignment. Computer Applications in the Biosciences 10, 227-235.); Clustal W (Thompson et al 1994, Nucleic Acid Res 11 (22)4673-4680.

In a preferred embodiment, a membrane spanning protein is as described herein. Preferably, it is OmpA.

The modifications to the membrane spanning proteins may be introduced by any suitable technique, many of which will be known to persons skilled in the art. For example, recombinant DNA technology may be used to introduce modifications to the nucleic acid sequence encoding the membrane spanning protein, which is expressed as a modified membrane spanning protein. Recombinant DNA techniques are provided in Sambrook (Sambrook, J. and Russell, D. W. (2001) Molecular cloning. A Laboratory Manual. CSHL Press).

In an aspect of the invention, there is provided a nucleic acid sequence encoding a modified membrane spanning protein as described herein. A nucleic acid sequence encoding a membrane spanning protein may be engineered to provide a modified membrane spanning protein as described herein.

OmpA is encoded by a gene which is known in the art as OmpA, con, tolG, and tut. The locus name is b0957 and JW0940. The nucleic acid sequence encoding OmpA is disclosed in the genome sequence of *E. coli* (www.b-mb.med.miami.edu/sources/1), and herein at FIG. 14. The sequence shown in FIG. 14 is an engineered form of the wild type gene. The sequence encoding the extracellular loops is underlined. Extracellular loop L1 is encoded by nucleic acids 85-126; L2 is encoded by nucleic acids 214-249; L3 is encoded by nucleic acids 346-387; L4 is encoded by nucleic acids 466-507. The C terminal proline is encoded by nucleic acids 589-591. The N terminal methionine is encoded by nucleic acids 1-3. The sequence intervening loops encodes the membrane spanning beta strands, as described in Table 1.

OmpF (also known as TOLF or CMLB or COA or CRY or B0929) may also be used in the present invention.

The present invention includes variant nucleic acid sequences encoding a membrane spanning protein of the present invention. The sequence identity of a variant or functionally equivalent sequence to a sequence encoding a membrane spanning protein of the invention is determined by comparing the two aligned sequences, or fragments thereof, over a pre-determined comparison window, and determining the number of positions at which identical residues occur. The comparison window may comprise all or part of the sequence, for example a window comprising 10, 20, 30, 40, 50, 100, 200, 500 or 1000 nucleotides or more. Typically, sequence identity is expressed as a percentage. The measurement of sequence identity of a nucleotide sequence is a method well known to those skilled in the art, using computer implemented mathematical algorithms such as ALIGN (Version 2.0), GAP, BESTFIT, BLAST (Altschul et al J. Mol. Biol. 215: 403 (1990)), FASTA and TFASTA (Wisconsin Genetic Software Package Version 8, available from Genetics Computer Group, Accelrys Inc. San Diego, Calif.), and CLUSTAL (Higgins et al, Gene 73: 237-244 (1998)), using default parameters.

Preferably, a nucleic acid molecule is provided in a genetic construct, which may be used for expression of a modified membrane spanning protein of the invention, for example in a host cell.

Preferably, the nucleic acid molecule is operably linked to a regulatory element, which is any nucleic acid sequence which regulates expression (i.e. transcription or translation) of a coding sequence to which it is operably linked. Regulatory sequences include promoters, enhancers, transcription terminators, initiation codons, splicing signals including acceptor and donor splice sites, stop codons, amber or ochre codons, transcription factor binding sites, ribosome binding sites, IRES, and targeting sequences such as cell compartmentalisation signals (e.g. to the cytosol, nucleus, plasma membrane, endoplasmic reticulum, mitochondria, chloroplast, lysosome, endosome or Golgi apparatus), and/or secretion signals. Other regulatory sequences may be known to persons skilled in the art. A genetic construct of the invention may comprise any one or more (two, three, four, five, six etc) regulatory sequences. One or more regulatory elements may be provided in a 5' UTR. Additionally, a 3' UTR may also be provided.

A promoter with reference to the present invention may be defined as a control sequence that directs transcription of a nucleic acid. A promoter includes necessary nucleic acid sequences near the start site of transcription, such as, in the case of a polymerase II type promoter, a TATA element. A promoter may optionally include distal enhancer or repressor elements that can be located as much as several thousand base pairs from the start site of transcription. Both constitutive and inducible promoters are included for use in the present invention.

Any constitutive or inducible promoter can be used. Common examples of promoters used for heterologous gene expression in E. coli are tac, trp, lac, T7, ara omp, lambda phage; but any promoter may be used to express these fusions proteins. In contrast to inducible promoters, constitutive promoters function under most environmental conditions. Many different constitutive promoters can be utilized with respect to the methods of this disclosure. Preferred promoters for use in the present invention include T7, ara, and tac.

A nucleic acid molecule of the invention may be operably linked to a selectable marker. Where a nucleic acid molecule is provided in a genetic construct, the construct may comprise a selectable marker. In embodiment, the selectable marker may be operably linked to the nucleic acid molecule. Alternatively, the selectable marker may be controlled independently to the nucleic acid molecule, for example under the control of a separate promoter and/or other regulatory elements.

Suitable selection markers will be well known to those skilled in the art, and may include any nucleic acid sequence which, upon expression, provides a detectable phenotype. Typically, the expressed polypeptide is detectable within the cell, preferably without adversely affecting the cell. For example, the selection marker may be green fluorescent protein or an enzyme, such as luciferase which generates a signal when contacted with a suitable agent. Other selective markers include those which confer upon the cell a selective ability to grow in certain conditions, for example in the absence of specified nutrients, or in the presence of an agent which would otherwise be adverse to the cell. Preferred selectable markers for use in the present invention include ampicillin, chloramphenicol, kanamycin and tetracycline resistance but others will be known and available to persons skilled in the art.

Suitable genetic constructs for use in the present invention include vectors including for example viral vectors, plasmids (circular or linear), phagemids, linear DNA. Preferred genetic constructs for use in the present invention include plasmids carrying an inducible promoter for the overexpression of the Omp fusion protein. A vector may include one or more selectable markers, as defined herein, one or more cloning sites, for example to allow homologous recombination with native nucleic acid, one or more regulatory elements as defined herein, and one or more origins of replication. Two or more nucleic acid molecules as defined herein may be provided in a single vector, where desired. These may be under separate regulatory control, or be operably linked to the same regulatory elements.

A nucleic acid sequence or genetic construct as described herein may be provided in a host cell for expression of a modified membrane spanning protein of the invention. Suitable host cells for recombinant protein expression include eukaryotic or prokaryotic cells, preferably the latter. Suitable host cells will be known and available to persons skilled in the art, and include for example E. coli, BL21, BL21 Al, BLR, and Rosetta-2. There may also be provided a host cell comprising a genetic construct as described herein. The host cell may be recombinant.

The present invention provides a method of binding a component in a sample, the method comprising:
i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
ii) adding sample to the substrate;

iii) maintaining the substrate with sample under conditions to allow binding of any component to the substrate.

Preferably, after addition of the sample to the substrate, the substrate may be incubated for a suitable period of time to allow any analyte to bind to the substrate. The incubation period may vary depending upon the assay and the sample type, but typically may be from 5 minutes to 24 hours, more preferably 10 min to 1 h depending on the assay being performed.

The method of the invention may be a screening assay, to detect the presence of absence of a component of interest in a sample. In such an assay, prior to detection to maximise accuracy of the assay, the method may comprise a step of washing the substrate to remove any unbound material. Washing may be performed with any suitable buffer, water, or solutions containing detergent or ethanol for example TBS, PBS, HEPES, TE, 70% ethanol, Tween, or deionised water, preferably sterile.

Detection of bound component may be performed using any suitable method in the art, for example using a binding assay with a binding partner specific for the analyte. In a typical binding assay, the substrate may be incubated with a binding partner specific for the analyte (for example, IgG). Bound analyte may then be detected, either directly for example if it comprises a signal which can be measured, or indirectly, for example by using a second binding member specific for the first binding partner. The second binding partner may be an antibody conjugated to enzyme or catalyst or other marker such as a fluorescent tag, and detection may be performed by incubation with a substrate and measuring the amount of signal produced. Any suitable signal may be used, many examples of which will be known and available to persons skilled in the art. Preferred signals are those that can be detected in the electromagnetic spectrum, such as chromophores and fluorophores, and enzyme substrate systems such as Horseradish peroxidase/TMB. Others will be known to persons skilled in the art. In the latter case, a binding member specific for the ligand may be bound to an enzyme, which catalyses the signal substrate to produce a colorimetric output. Preferred signals are those which employ an amplification system. Enzyme labels which can act on a substrate to produce chromophores are most preferred, e.g. Horseradish Peroxidase, alkaline phosphatase, beta galactosidase. Suitable substrates include TMB ABTS, OPD (for HRP), pNPP (for AP) and ONPG (for beta galactosidase). A colourimetric output may be measured visually, or quantitatively by measuring changes in absorbance of light. The method may further comprise comparing the signal generated to a standard chart, to obtain a quantitative value of amount of analyte based upon the signal.

The sample may be derived from a human or animal body (for example saliva, whole blood, plasma, urine, semen, faeces, etc) or may be cell lysate or crude extract from a production process.

A component may be any moiety, preferably one which is capable of being bound by a binding partner. A non-limiting selection of ligands include nucleic acid, antigen, antibody, oligonucleotide, hormone, hapten, hormone receptor, vitamin, steroid, metabolite, aptamer, sugar, peptide, polypeptide, protein, glycoprotein, a cell, organism (such as fungus, bacteria, viruses, protozoa and multicellular parasites), therapeutic or non-therapeutic drugs, or any combination or fragment thereof. Preferably, the component may be an immunologically active protein or polypeptide, such as an antigenic polypeptide or protein.

The method may also be used for purification of a component of interest from a sample. Such a method may be as described above in relation to a screening method, where instead of detecting component, any bound component may be eluted from the substrate. Any bound product may be eluted from the substrate using methods known in the art, for example salt elution, elution by pH change, elution by competitor binding.

The method may also be used for immobilising a component of interest from a sample, for example for further reaction, for example as described herein. For example, the peptide and/or protein may comprise an Fc binding domain (e.g. from protein A, G or L), which may serve to immobilise components exhibiting an Fc domain (e.g. Fc tagged recombinant protein). Such immobilisation may have a variety of uses, for example in binding assays, cell culture etc.

The method may comprise immobilising a membrane spanning protein on a polymeric substrate, as described herein. Preferably, the polymeric substrate comprises a membrane spanning protein immobilised thereon, wherein the membrane spanning protein is immobilised upon the substrate by physisorption, and wherein the membrane spanning protein comprises a heterologous peptide and/or protein. The membrane spanning protein comprises a head and a foot, the head and foot being spaced apart from one another by one or more membrane spanning strands. By anchors means that the membrane spanning protein may comprise a heterologous peptide and/or protein in a loop at the head of the protein and/or a heterologous peptide and/or protein at an N and/or C terminus at the head of the protein. By modified to anchor means that the membrane spanning protein is engineered to comprise an N and/or C terminus at the head of the protein, and/or one or more loops at the head of the protein.

Thus, the membrane spanning protein may:
 i) comprises a heterologous peptide and/or protein in a loop at the head of the protein;
 ii) comprises a heterologous peptide and/or protein at an N and/or C terminus at the head of the protein;
 iii) is engineered to comprise an N and/or C terminus at the head of the protein; and/or
 iv) is engineered to comprise one or more loops at the head of the protein.

A heterologous peptide and/or protein may be provided at an engineered N and/or C terminus at the head of the protein, or in an engineered loop at the head of the protein, for display.

The present invention also provides a method of mediating an interaction of an anchored peptide and/or protein with a component in a sample, the method comprising:
 i) providing a polymeric substrate comprising a membrane spanning protein immobilised thereon, wherein the membrane spanning protein is immobilised upon the substrate by physisorption, and wherein the membrane spanning protein anchors a heterologous protein or peptide for display;
 ii) adding sample comprising a component to the substrate;
 iii) maintaining the substrate with sample under conditions to allow interaction of the component with anchored peptide and/or protein.

Preferably, the method comprises providing a polymeric substrate comprising a membrane spanning protein immobilised thereon, as described herein.

The sample may be derived from a human or animal body (for example saliva, whole blood, plasma, urine, semen, faeces, etc) or may be cell lysate or crude extract from a production process, or may be a cell culture of reaction mixture.

A component may be one which is capable of interacting with an anchored peptide or protein. It may be any moiety, including for example nucleic acid, antigen, antibody, oligonucleotide, hormone, hapten, hormone receptor, vitamin, steroid, metabolite, aptamer, sugar, peptide, polypeptide, protein, glycoprotein, cell, organism (such as fungus, bacteria, viruses, protozoa and multicellular parasites), therapeutic or non-therapeutic drugs, or any combination or fragment thereof. The component may be an immunologically active protein or polypeptide, such as an antigenic polypeptide or protein. Preferably, the component is a cell. A cell may be a prokaryotic cell, for example a fungal or bacterial cell, or a eukaryotic cell, for example a mammalian cell, preferably a human cell.

Preferably, after addition of the sample to the substrate, the substrate may be incubated for a suitable period of time to allow any reaction of the peptide and/or protein with a component of the sample. The incubation period may vary depending upon the assay and the sample type, but typically may be from 5 minutes to 24 hours, more preferably 10 min to 1 h depending on the assay being performed.

Where the component is a cell, the assay may be useful in providing cellular interactions to a cell culture, for example for example providing peptide or proteins which signal the cell to grow, divide an/or differentiate, or to express a particular characteristic or function. For example, the protein may be a growth factor which interacts with receptors on the cell surface when the substrate is incubated with cell culture. Alternatively, the peptide may comprise an ECM motif, which again may interact with receptors on the cell surface, prompting particular cellular characteristics or differentiation. Examples of modified OMP proteins for use in cell binding assays include OMP153, 154, 162-165, 167, 174-179, and 180-192 (Tables 3 and 4).

Methods for promoting cell growth and/or differentiation using surface coated substrates and methods of cell culture are known in the art, and their teaching can readily be applied to using the substrates of the present invention in a method of cell culture of promoting cell growth and/or differentiation (see for example Helgason and Miller (Eds.) (2004) Basic cell culture protocols, Humana Press, ISBN 1588292843).

A cell for use in a method of the invention may be a eukaryotic or prokaryotic cell. The cell may be an insect cell, yeast, bacteria, plant cell, algae, and animal cell, preferably mammalian cells. It may be a cell line. Animal and mammalian cells fibroblasts, stem cells, induced pluripotent stem cells, neuronal cells, hepatocytes, myocytes, haematopoietic cells, epithelial cells, primary cells, transformed cell lines.

The method may also be useful in an enzymatic assay, for example where the peptide and/or protein encodes an enzyme or catalyst. Upon incubation with the sample, the anchored enzyme or catalyst reacts with component in the sample to provide a reaction product. The method may comprise removing the sample from the substrate and purifying any reaction product therefrom, or detecting the presence of reaction product.

The method may be used for immobilising peptides or proteins which are required in an assay, for example a cell culture assay. As described above, for example, the peptide and/or protein may comprise an Fc binding domain (e.g. from protein A, G or L), which may serve to immobilise components exhibiting an Fc domain (e.g. Fc tagged recombinant protein). Such immobilisation may have a variety of uses, for example in binding assays, cell culture etc.

The present invention also provides an incubation comprising a polymeric substrate, a membrane spanning protein, and detergent at a concentration of IxCMC or below. Preferably, the membrane spanning protein, substrate and detergent are as described herein. The incubation reflects an intermediate in the manufacture of a polymeric substrate or product of the invention, in which a polymeric substrate is incubated with a membrane spanning protein as defined herein, where the detergent concentration in the incubation is 1×CMC or below. The polymeric substrate may be unbound or partially bound with membrane spanning protein which becomes immobilised thereon.

In a ninth aspect of the present invention, there is provided a kit comprising a polymeric substrate, and a membrane spanning protein which anchors, or is modified to anchor, a heterologous protein or peptide for display. The membrane spanning protein comprises a head and a foot, the head and foot being spaced apart from one another by one or more membrane spanning strands. By anchors means that the membrane spanning protein may comprise a heterologous peptide and/or protein in a loop at the head of the protein and/or a heterologous peptide and/or protein at an N and/or C terminus at the head of the protein. By modified to anchor means that the membrane spanning protein is engineered to comprise an N and/or C terminus at the head of the protein, and/or one or more loops at the head of the protein. Thus, there may be provided a polymeric substrate comprising a membrane spanning protein immobilised thereon, wherein the membrane spanning protein is immobilised upon the substrate by physisorption, and wherein the membrane spanning protein:

i) comprises a heterologous peptide and/or protein in a loop at the head of the protein;

ii) comprises a heterologous peptide and/or protein at an N and/or C terminus at the head of the protein;

iii) is engineered to comprise an N and/or C terminus at the head of the protein; and/or iv) is engineered to comprise one or more loops at the head of the protein.

A heterologous peptide and/or protein may be provided at an engineered N and/or C terminus at the head of the protein, or in an engineered loop at the head of the protein, for display.

The kit may additionally comprise a chart providing dilution factors to enable physisorption of a membrane spanning protein to a polymeric substrate, diluents, buffers, substrate, immunoglobulin and binding reagents. The kit may be packaged, for supply and transport. The components of a kit may be individually packaged and supplied as a combination of reagents to practice a method of the invention.

The methods of the invention may further comprise the step of modifying a membrane spanning protein, as described herein, prior to immobilisation of a protein onto a polymeric substrate.

The methods of the invention may further comprise the step of modifying a nucleic acid sequence encoding a membrane spanning protein, to provide a modified membrane spanning protein as described herein, and expressing the protein from a host cell, prior to immobilisation of the modified membrane spanning protein onto a plastic substrate.

The present invention also provides a product comprising a polymeric substrate comprising a membrane spanning protein which anchors, or is modified to anchor, a heterologous protein or peptide for display. The membrane spanning protein comprises a head and a foot, the head and foot being spaced apart from one another by one or more membrane spanning strands. By anchors means that the membrane spanning protein may comprise a heterologous peptide and/ or protein in a loop at the head of the protein and/or a heterologous peptide and/or protein at an N and/or C terminus at the head of the protein. By modified to anchor means that the membrane spanning protein is engineered to comprise an N and/or C terminus at the head of the protein, and/or one or more loops at the head of the protein. Thus, there may be provided a polymeric substrate comprising a membrane spanning protein immobilised thereon, wherein the membrane spanning protein is immobilised upon the substrate by physisorption, and wherein the membrane spanning protein:

i) comprises a heterologous peptide and/or protein in a loop at the head of the protein;
ii) comprises a heterologous peptide and/or protein at an N and/or C terminus at the head of the protein;
iii) is engineered to comprise an N and/or C terminus at the head of the protein; and/or
iv) is engineered to comprise one or more loops at the head of the protein.

A heterologous peptide and/or protein may be provided at an engineered N and/or C terminus at the head of the protein, or in an engineered loop at the head of the protein, for display.

A product may include micro-well plates, tissue culture flasks or plates, plastic beads, fibres, mesh substrates, medical devices such as surgical implants, micro- or nanoparticles of polymers. There is provided a surgical implant comprising a polymeric substrate comprising a membrane spanning protein immobilised thereon, wherein the membrane spanning protein is immobilised upon the substrate by physisorption, and wherein the protein retains its native secondary structure.

EXAMPLES

Figure 1:
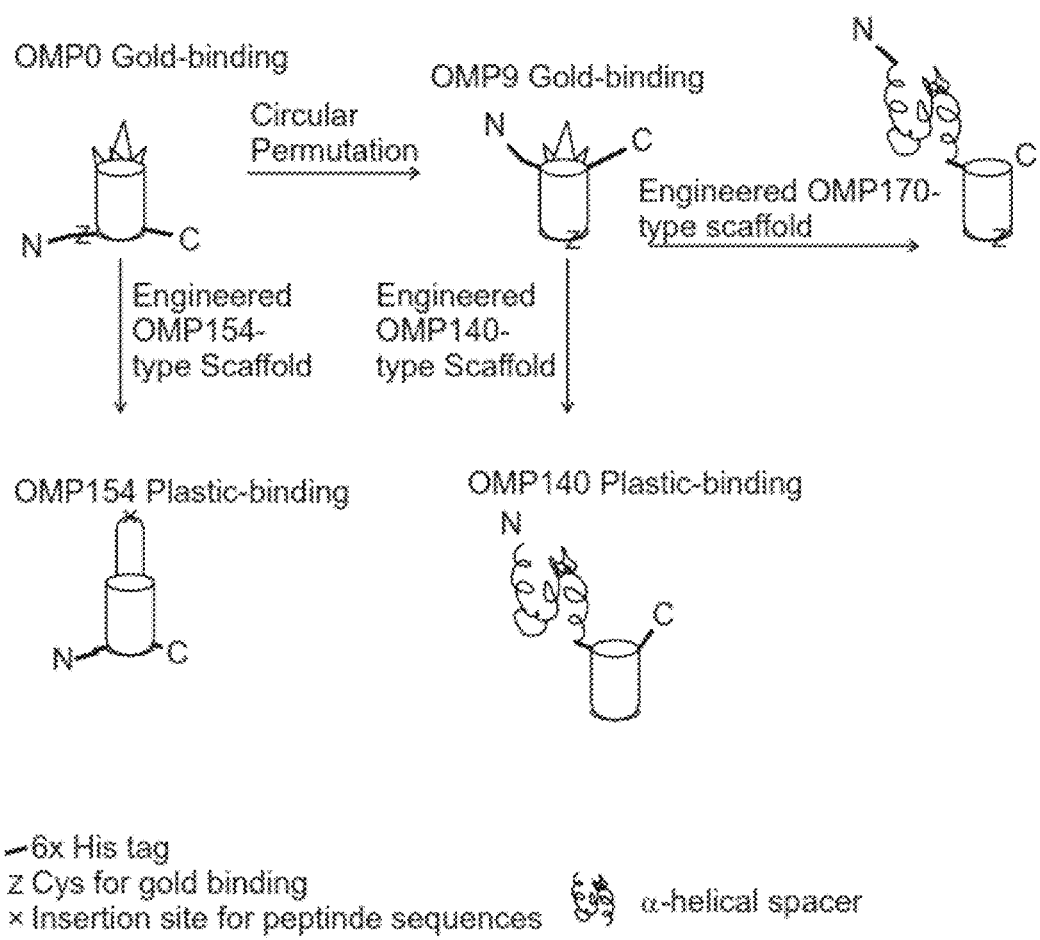
FIG. 1 shows the design of plastic binding β-barrel proteins based on the directed evolution of the β-barrel scaffold protein OmpA. OMP0 is the original gold-binding modified version of OmpA that has truncated N- and C-termini, a 6×His tag for affinity purification and a cysteine at the 'foot' of the protein for covalent bonding to gold.

In order to investigate the binding and function of our β-barrel based proteins to polymers we have adopted the following approaches:
1. Immunoassay for Detection of Protein on Polymers
Comparison of OMP18 (two IgG-binding B domains of SPA fused to OmpA) and native *Staphylococcus aureus* Protein A (five IgG-binding domains).
Detection of FLAG-tagged OMP proteins on various polymers
Detection of human HIV p24 antigen fused to OMP scaffold with specific antibody and comparison to native antigen
2. Cell Culture
Comparison of cell attachment to OMP0 scaffold protein and various constructions containing ECM protein motifs or growth factors displayed on the OMP scaffold.
Binding of IgG to Native Protein a or Protein a Domains Anchored with Peta-Barreled Scaffold For any scaffold to be effective as an anchor for a second independent protein, it must improve the function of that protein when adsorbed to a surface. To examine this for the beta-barreled scaffold, we performed experiments using one our range of IgG-binding proteins OMP18, which has a tandem repeat of the IgG-binding B-domain of *Staphylococcus aureus* Protein A fused to the N-terminus of the OMP9 scaffold. OMP9 is shown in FIG. 1, and is a gold binding beta barrelled protein comprising all extracellular loops, cysteine residue for gold binding, circularly permutated N and C termini and a shorted N terminus, which in OMP18 is fused to the tandem repeat of the IgG-binding B-domain of *Staphylococcus aureus* Protein A. This latter domain binds to the Fc region of antibody leaving the antigen-binding regions exposed.

Figure 4:
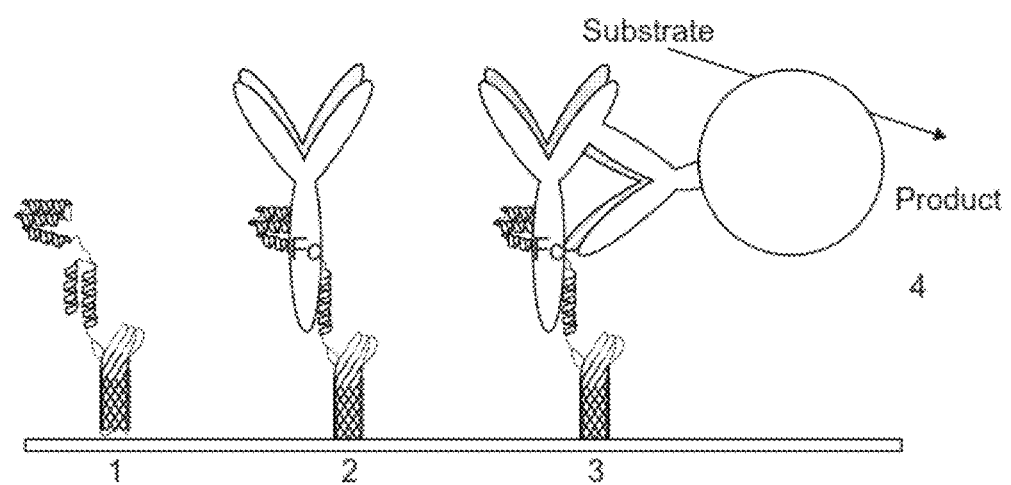
FIG. 4 is a schematic diagram of IgG-binding functional assay for OMP18 and Native Protein A. The OMP18 structure is shown in the figure. In step 1, the protein is attached to the plastic surface; in step 2 IgG is bound to any functional IgG-binding domains; in step 3 and anti-IgG antibody conjugated to alkaline phosphatase that cannot bind to the Protein A domains is bound to any IgG already on the surface; and in step 4 a colorimetric enzymatic reaction is carried out to discern surfaces that have immobilized IgG.

OMP18 can capture IgG antibodies on a gold biosensor surface with greater efficiency than adsorbed or amine coupled protein A (unpublished data). In order to test whether this would be the case for Protein A domains tethered to plastic via the OMP scaffold we compared immobilisation of OMP18 vs Protein A on polystyrene surfaces in the type of immunoassay described in FIG. 4. In this scenario, we envisage that correctly oriented proteins would bind larger amount of antibody than incorrectly oriented or denatured proteins, thereby yielding an improved signal from the immune-detection.

Protein Adsorption of OMP18 and Protein a to Plastic Well Plates

One hydrophobic 24-well plate (Corning) and one 'hydrophilic' plate (Corning) were used. OMP18 (Lot 15910BE16511LH) was in PBS (phosphate buffered saline)+0.25% OG (n-octylglucoside) at 70 µg/mL (2 µM) and native *Staphylococcus aureus* Protein A (Sigma Cat. No. P7387; Lot 055K09261) in PBS+0.25% OG at 84 µg/mL (2 µM).

300 µL of protein solution was applied to wells on both plates. Blank wells (no protein) were prepared with just PBS+0.25% OG. The plates were incubated overnight on rocking platform (rocker) at room temperature (RT). Wells were coated in triplicate with each protein.

Immunoassay to Compare OMP18 with Native Protein a on Plastic

The wells were washed once with Tris-buffered saline+ 0.05% (v/v) Tween 20 (herein referred to as TBS-T). Note, all washes and incubations were with 300 µL of solution unless stated otherwise. Mouse IgG (Sigma Cat No. 15381, Lot. 025K7580) at 2 µg/mL in Tris-buffered saline+0.05% (v/v) Tween 20+3% (w/v) BSA (herein referred to as TBS-TB) was added to two wells of each type and TBS-T was added to a no antibody control well and incubated for 1 h at RT on rocker. Mouse IgG solution and TBS-T solution were removed and wells washed three times with TBS-T. Rabbit anti-mouse IgG-AP conjugate (Sigma Cat. No. A3688, Lot. 103K9157) diluted 1/5000 in TBS-T was added to all the wells. The wells were maintained for 1 h at room temperature on a rocker. Conjugate was removed and the wells washed in 3×TBS-T. 200 µL of (PNPP) substrate was added to each well and incubated 30 min room temperature in dark. The reaction was stopped by the addition of 50 µL of 3M NaOH solution in deionised water. The contents of the well were mixed with 0.75 mL of deionised water and absorbance at 405 nm was measured in a Shimadzu 1240 spectrophotometer.

Figure 5:
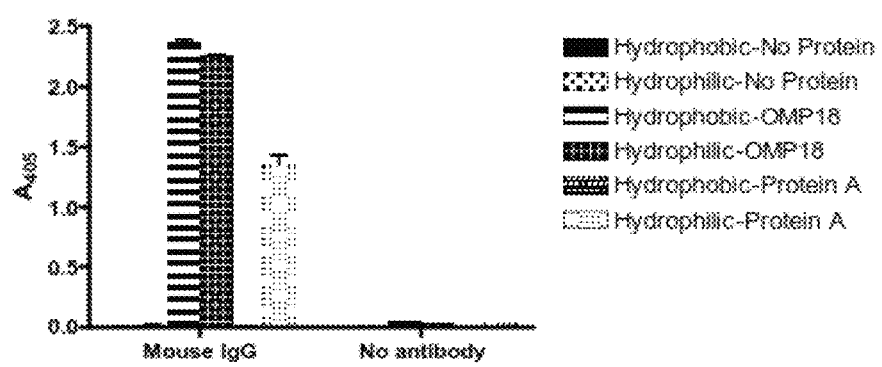
FIG. 5 shows the results of immunoassay to test for presence of functional protein on surfaces. These data clearly demonstrate that immobilization of Protein A IgG-binding domains fused to an OMP beta barrel scaffold anchor retains much greater function on plastic surfaces. The scale of the advantage was unexpected and this is especially marked on the hydrophobic surface compared to the hydrophilic surface. Even on the hydrophilic surface the OMP18 protein shows much greater functionality than native protein A.

The raw data is in Table 1 and plotted in FIG. 5 as a bar graph.

TABLE 1

$A_{405}$ readings from each well.

| | No Protein Hydrophilic | No Protein Hydrophobic | OMP18 Hydrophilic | OMP18 Hydrophobic | Protein A Hydrophilic | Protein A Hydrophobic |
|---|---|---|---|---|---|---|
| mIgG Well1 | 0.018 | 0.001 | 2.237 | 2.390 | 1.258 | 0.014 |
| mIgG Well 2 | 0.019 | 0.005 | 2.233 | 2.332 | 1.433 | 0.010 |
| No IgG Conjugate only | 0.023 | 0.005 | 0.027 | 0.056 | 0.025 | 0.003 |

Use of Flag-Tagged OMP Scaffolds on PLA

Figure 6:
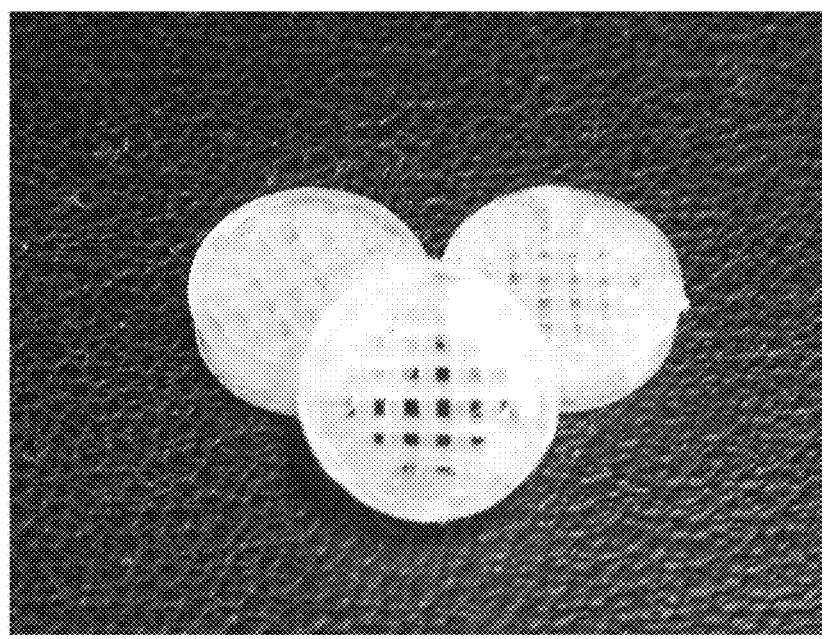
FIG. 6 shows poly lactic acid polymer 3D printed into open lattice 3D discs. The discs were treated with OMP0 (umodified OmpA) and OMP5 (OMP0 engineered to display the FLAG epitope). After protein treatment all the surfaces could be tested with an alkaline phosphatase conjugated anti-FLAG antibody to quantify protein attachment.

As a hydrophobic polymer we thought polylactic acid (PLA) would be a good candidate as material to which we could attach OMP proteins. In order to assess this we obtained some 3D printed PLA discs from Prof. K Dalgarno (Newcastle University). The structure of the discs is shown in FIG. 6.

Protein Adsorption onto PLA Discs

A hydrophobic 48 well plate (Nunc) was used to hold the discs during treatment. OMP0 (Modified OmpA protein comprising a cysteine residue at position 10 to enable gold binding; (see FIG. 13 for the sequence of OmpO (SEQ ID NO: 2 and 12).) (Lot.91012BE12313) and OMP5 (Lot.8910BE18213) were diluted to 32 µM in PBS containing diluted detergent as before. 600 µL were added to each PLA disc, control discs were treated with the same solution lacking protein. The 48 well plate was sealed with parafilm and stored at 4° C. for 16 hours. Each PLA disc was washed twice with sterilized 500 µL deionized water (Lot.251013YD) to remove excess unattached protein. OMP5 is the OmpA with a FLAG epitope in extracellular loop 1. The FLAG epitope is DYKDDDDK (SEQ ID NO: 19).

Antibody Detection of OMP5

A 1:1000 dilution of M2 anti-FLAG alkaline phosphatase conjugated antibody (Sigma Cat No. A9469; Lot. 091M6287) was prepared in TBS-T. Treated PLA discs were transferred to a new 48 well plate (Nunc) and 500 µL diluted antibody was added to each PLA disc. After 30 minutes at room temperature the antibody solution was removed and each disc was incubated twice for 5 minutes in 500 µL TBS-T. 500 µL 1 Step PNPP reagent (Sigma Cat No. Lot.N114473612) was added to each PLA disc after 5 minutes at room temperature the reaction was stopped by the addition of 500 µL 1M NaOH (Lot.). 200 µL solution was removed from each well containing a PLA disc and transferred to a 96 well plate. The absorbance of the wells was measured at 405 nm using a Thermo Scientific Multiskan FC microplate reader.

Figure 7:
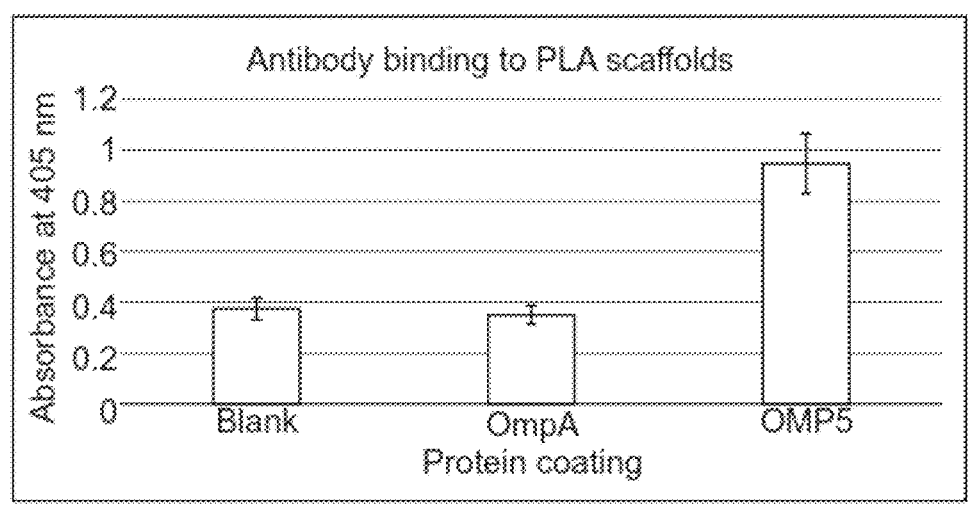
FIG. 7 shows the detection of FLAG epitope with alkaline phosphatase conjugated antibody and PNPP. Error bars represent standard deviation. Note that OmpA here refers to OMP0. Similar levels of non-specific binding were seen on the no protein and OMP0 treated surfaces with significantly more antibody binding to the OMP 5 treated surfaces.
Figure 8:
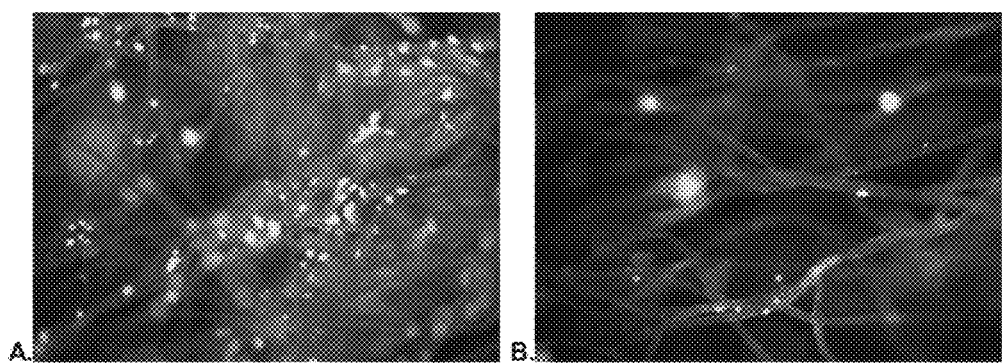
FIG. 8 shows DAPI stained PC12 cells grown on; A. OMP36 treated polymer fibres, B. Protein-free fibres. Both images captured using 10× objective lens.

The raw data is in Table 2 and plotted in FIG. 7 as a bar graph.

TABLE 2

Absorbance at 405 nm for each well.

| Blank | OmpA | OMP 5 |
|---|---|---|
| 0.412 | 0.312 | 0.88 |
| 0.335 | 0.361 | 1.086 |
| 0.369 | 0.374 | 0.877 |

Use of OMP Scaffolds to Display ECM Motifs on Polyester Fibres and Polystyrene Plates It has previously shown that OMP's modified OmpA proteins assembled as an oriented monolayer on gold[7] and that the addition of integrin binding motifs to the β-barrel could improve the attachment of cells to gold surfaces[9]. In the experiments detailed here it was examined whether binding of these proteins to polyester fibres improved the attachment of cells.

Use of OMP Proteins with Discs Made from Electrospun Polyester Fibres

Discs made from electrospun polypropylene fibres with a polyethylene core were sourced from Applied Cell Biotechnologies Inc. and were coated with OMP36 using dialysis to remove the detergent from the protein solution. OMP36 contains the YIGSR motif from laminin (SEQ ID NO: 27). Once treated with protein the fibre discs were seeded with cells and the number of cells attached was assessed by microscopy.

Protein Treating Polymer Fibres.

Electrospun polymer samples were placed in Spectra/Por rc dispodialyser (15000 Dalton molecular weight cut off; Lot.3205922) with 5 mL OMP36 (Lot.22605BE23407) at 10 µg/mL in ROG-8 buffer, duplicate samples were treated with protein-free ROG-8. The dialysis bags were placed in a 1 liter beaker containing 800 mL dialysis buffer (50 mM Tris, 0.1 mM EDTA), a magnetic stirrer was used to gently stir the solution. The dialysis buffer was removed and replaced with fresh buffer at 2 hours, 30 hours, 38 hours and 4 days. After 5 days the polymer samples were removed from the dialysis tubing and were washed deionized water.

Testing Electrospun Polymer Fibres with Cells

Polymer discs were soaked in 70% ethanol for 10 minutes to sterilize them prior to addition of the cells; this was followed by a quick wash in PBS (Lot.15307SP) to remove any residual ethanol. PC12 neuronal cells (passage 27, ~90% confluent) were harvested with trypsin/EDTA and suspended in RPMI1640 media (containing 10% Foetal calf serum) at $1 \times 10^6$ cells per mL.

3 ml of cells were added to duplicate OMP36 treated and protein-free ROG-8 treated polymer discs. The cells were incubated overnight at 37° C., 5% $CO_2$ in a humidified incubator. After 16 hours the discs were soaked in PBS containing 4% w/v paraformaldehyde (BDH; Lot.K32259648) at room temperature for 10 minutes followed by 30 minutes in PBS containing 1 µg/mL DAPI (Lot.50307SP). Cells were visualized using a fluorescent microscope.

The DAPI staining clearly shows the nuclei of many cells on each fibrous material, but there are many more cells on the OMP36 treated fibres.

Adsorbed OMP Scaffold on Polystyrene Plates with Cells

Above it was shown that the β-barreled molecules were still able to improve cell attachment even when they were adsorbed onto polyester fibres. It was then examined whether a similar effect could be achieved on polystyrene tissue culture multi-plates just by drying the proteins onto the plates.

Protein Treatment of Polystyrene Plates.

6 and 12 well tissue culture modified (hydrophilic) Nunclon Δ plates (Nunc) were incubated with OMP36 in PBS with 0.25% OG as before at 4° C. for 16 hours. 6 well plates contained 500 μL protein per well the 24 well plates contained 300 μL protein per well. After incubation each well was washed twice with deionized water then sprayed with 70% ethanol to sterilize. The plates were left in a cell culture hood for 10 minutes to allow most of the ethanol to evaporate then each well was washed with sterile PBS.

Testing Protein Treated Plates with 3T3 Murine Fibroblasts

3T3 fibroblasts (passage 147-70% confluent) were harvested using trypsin/EDTA and resuspended at $5 \times 10^4$ cells per ml Dulbecco's modified Eagle's medium (containing 10% foetal calf serum). 3 untreated wells and 3 protein treated wells in a 6 well plate were each seeded with 3 mL cells. 4 untreated wells and 4 protein treated wells in a 24 well plate were each seeded with 750 μL cells. Plates were incubated overnight at 37° C., 5% $CO_2$ in a humidified cell culture incubator. After 16 hours incubation the media was discarded from each plate and PBS containing 4% w/v paraformaldehyde (BDH; Lot.K32259648) at room temperature for 30 minutes followed by 10 minutes in PBS containing 1 μg/mL DAPI (Lot.50307SP). Cells were visualized using a fluorescent microscope and the number of cells in free random fields of vision per well were counted.

Figure 9:
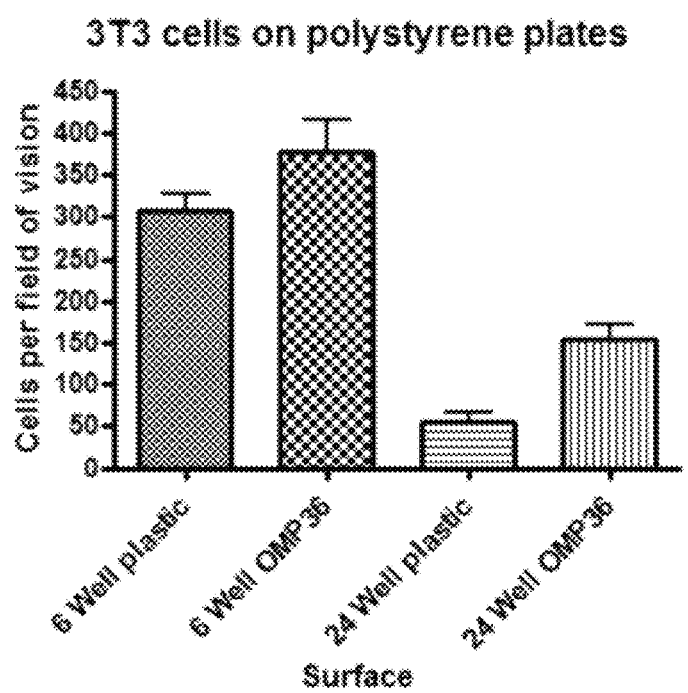
FIG. 9 shows the attachment and growth of 3T3 fibroblasts on OMP36 treated plates.

Data are plotted in the bar chart shown in FIG. 9. Treating polystyrene plates with OMP36 improves the attachment of cells to the polystyrene.

Use of OMP Scaffolds for the Display of Growth Factors for Cell Culture

The first cell culture experiments targeted enhancing the attachment of cells to surfaces, as the protein technology was developed to allow the insertion of larger proteins and peptides into OMP scaffolds we widened our interest to include much larger targets such as growth factors. The first two growth factors selected as targets for engineering were Fibroblast Growth Factor 1 (FGF1, acidic FGF) and Fibroblast Growth Factor 2 (FGF2, basic FGF). The work documented here covers experiments attaching FGF1 and FGF2 to polystyrene plates and testing the effects with mouse 3T3 fibroblasts.

Protein Treating Polystyrene Plate

500 μL 2 μM protein solutions were prepared in Dulbecco's phosphate buffered saline (D-PBS sourced from Sigma, Lot.090512SP) containing 0.25% n-octylglucoside; OMP0 (Lot.230511), OMP90 (FGF1; Lot.170809BE201009) and OMP128 (FGF2; Lot120111 BE170111). 100 μL of each protein solution were added to 4 wells of a 96 well polystyrene plate, this was followed with 100 μL D-PBS per well. The 96 well plate was wrapped in parafilm and stored overnight at 4-8° C. After 16 hours the protein solutions were removed and each well was washed with 100 μL 1% Triton-X-100 in deionised water followed by two 100 μL deionised water washes. The 96 well plate was air dried then sealed in plastic and stored at 4-8° C.

Testing FGF Treated Plates with 3T3 Fibroblasts

Murine 3T3 fibroblasts (passage 157, ~90% confluent) were harvested with trypsin/EDTA and resuspended in Dulbecco's Modified Eagle's Media (DMEM; containing 10% foetal calf serum) at $1 \times 10^4$ cells per mL. The 12 protein-coated wells and 4 untreated wells were each seeded with 200 μL cell suspension. An additional 4 untreated wells were seeded with 200 μL cell suspension containing 12.5 ng/mL soluble FGF2 (R&D Systems). Plates seeded with cells were incubated at 37° C., 5% $CO_2$ in a humidified incubator for 18 hours.

Media containing unattached cells was discarded, 100 μl D-PBS containing 4% w/v paraformaldehyde (BDH; Lot.K32259648) was added to each well, after 30 minutes at room temperature the D-PBS was replaced with 100 μL Crystal Violet solution (Pro-Lab Diagnostics; Lot.K12560) after a further 30 minute incubation the staining solution was discarded and each well was washed 3 times with 100 μL deionised water. The wells seeded with cells were examined using an inverted microscope, 1 random field of vision was selected per well and all the visible cells were counted.

Figure 10:
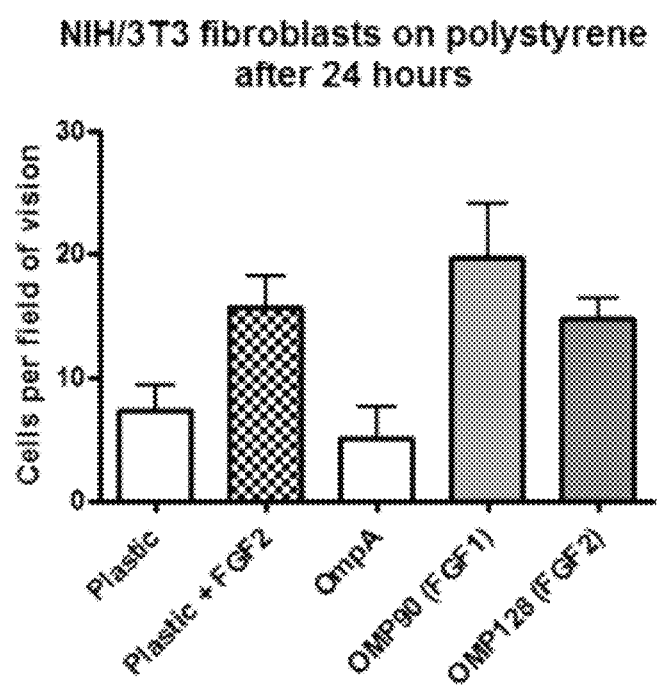
FIG. 10 shows a comparison of OMP FGFs coated on polystyrene to soluble FGF2 in the media.

Data are shown below in FIG. 10. Both OMP90 (FGF1) and OMP128 (FGF2) replicate the mitogenic effect observed when culturing the fibroblasts in the presence of 12.5 ng/mL soluble FGF2. Treating the polystyrene wells with OMP0 (OmpA scaffold) has no effect on the number of cells observed after 24 hours. The mitogenic effects of OMP90 and 128 are similar when the proteins are self-assembled as an oriented protein monolayer on a gold coated glass coverslip.

Engineered Variants of the Beta-Barrel Protein Scaffold

Our original 'Biosensor' patent covers the use of all β-barrel proteins for use as scaffolds for self assembly on gold (Leckband, D. and Langer, R. (1991) An approach for the stable immobilization of proteins. *Biotechnol Bioeng* 37: 227-237). The work described here has been carried out with derivatives of the *E. coli* OmpA protein. We have engineered the original scaffold in novel ways to improve the function on plastic as shown in FIG. 1.

Construction of Expression Clones

In each case the novel sequence of amino acids was back-translated to DNA sequence and codon optimized for expression in *E. coli*. The DNA fragments were synthesized as cassettes or whole genes by an external contactor Integrated DNA Technologies (IDT) under confidence and without any knowledge of the purpose or function of the novel genes. More detail about each base scaffold type is provided below (2.5.3. onwards). The molecular construction of expression clones for the novel modifications of the β-barrel proteins was carried out using standard molecular biology techniques that are described in detail elsewhere (Sambrook, J. and Russell, D. W. (2001) Molecular cloning. A Laboratory Manual. CSHL Press). Correct constructs were identified initially by restriction analysis and validated by DNA sequencing carried out by external contractor Beckman Coulter Genomics under confidence and without any knowledge of the purpose or function of the sequence. The novel β-barrel proteins were used as scaffolds for the fusion of other proteins and peptides of interest for immobilization on plastics as described in the sections below.

OMP170-Type Scaffolds Fused to HIV P24 Antigen

In order to exemplify the significant advantages of the technology we created variants of the OMP170-type β-barrel proteins fused to the HIV p24 protein and demonstrated markedly improved recognition by antibodies. The experiments are recorded in Book 55. OMP170 and OMP171 are two scaffold proteins with truncated loops and truncated C-terminus. They also have the cysteine left intact so that the proteins can be used on both gold and plastic. OMP170 has, in addition, an alpha helical spacer at the N-terminus that separates the fusion site from the β-barrel—this separates the domains and allows more efficient refolding. The alpha helical spacer is a mutated form of the *Staphylococcus aureus* Protein A B domain that does not bind to IgG. The construction is based upon the mutated version of the D domain that was reported by Kim et al Kim, H. K. (2010) Nontoxigenic Protein A vaccine for methicillin-resistant *Staphylococcus aureus* infections in mice. *J Exp Medicine* 207: 1863-1870. An alignment of OMP171 with OMP59, which is OMP9 with an alpha-helical spacer, is shown in FIG. 11.

Construction and Purification of Fusion Proteins

Figure 12:
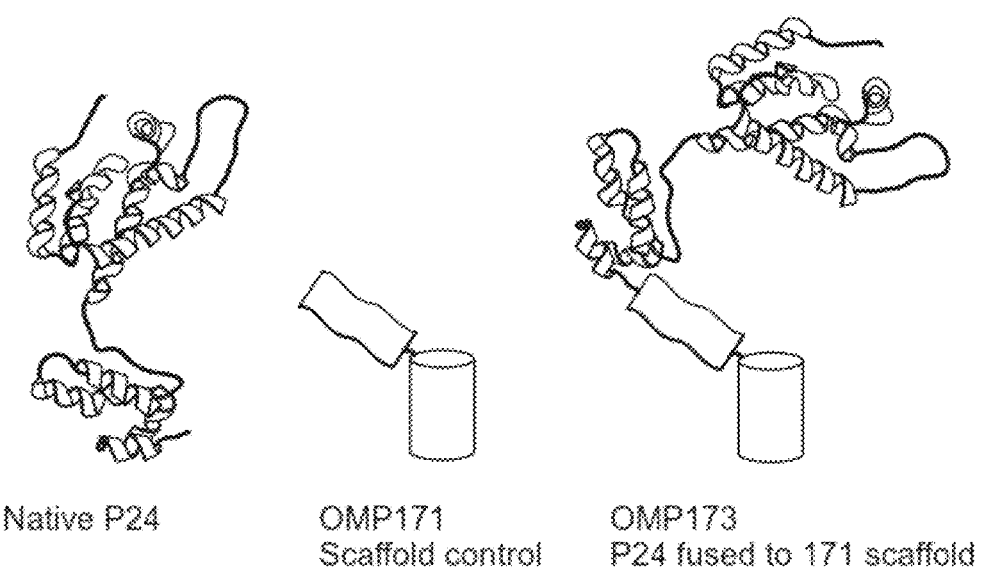
FIG. 12 is a schematic figure showing the structures of the proteins tested in this experiment.

Novel recombinant fusion proteins with human HIV P24 protein consensus sequence derived from major subtypes (C, B, A, D, F, G, H, J, K, CRF01_AG and CRF03_AB) was fused to the OMP171 scaffold protein (FIG. 12). The coding sequence for the P24 consensus for fusion to the OMP scaffold was generated by backtranslating the amino acid sequence and codon optimization for expression in *E. coli*. This was ligated with the scaffold coding sequences using standard molecular biology techniques (Sambrook, supra) The native P24 was recombinant HIV P24 antigen purchased from Capricorn Inc (Cat No. HIV-007-B0646, Lot. HIV130759). OMP171 and 173 were purified and refolded from inclusion bodies as described below (see General Methods below).

Immobilisation on Plastic Plates

Native P24 was diluted to 4 μg/mL in PBS buffer. OMP171 and 173 were diluted to 2 μM in PBS containing 0.25% (w/v) OG. 200 μL of diluted proteins were added to wells of 96-well untreated polystyrene plates (Corning #3370) and also to Polysorp plates (Nunc #475094). The proteins were allowed to bind overnight at 4° C. and then washed three times with 200 μL of autoclaved deionised water (SDVV) and used immediately.

Detection with Anti-P24 Antibodies

Two types of monoclonal anti-P24 antibodies were purchased from Capricorn:

1. Anti-HIV1-P24 monoclonal antibody from mouse (Cat No. HIV-018-48294, Lot. HIV122936); 2. Anti-HIV1/2 P24 monoclonal antibody from mouse (Cat No. HIV-018-48304, Lot. HIV111641).

1. The wells were blocked with TBS-TB. 30 min room temperature.

2. The two antibodies were each diluted to final concentrations of 0.5, 1, 10, 50, 100, 500 and 1000 ng/mL in TBS-TB. 200 μL of each concentration were added to three wells of each type of antigen surface. Zero control was carried out on each surface by the addition of TBS-TB alone. 30 min room temperature.

3. The wells were washed thrice with 200 μL of TBS-T.

4. 200 μL of 1/10000 dilution of secondary antibody, goat anti-mouse IgG alkaline phosphatase conjugate (Sigma Cat. No. A3688, Lot. 103K9157) in TBS-TB were added to each well. 30 min room temperature.

5. The wells were washed thrice with 200 μL of TBS-T.

6. 100 μL of p-nitrophenyl phosphate liquid substrate (Sigma) were added to each well. 15 min at room temperature.

7. Reaction stopped by addition of 50 μL of 3M NaOH to each well.

8. $A_{405}$ measured using a plate reader.

The data plots are shown in FIG. 13. The native P24 antigen that was directly adsorbed to the surfaces was not recognized at all by either antibody on polystyrene plates. On the Polysorp plates, the native P24 showed signal with both antibodies but that with Anti-HIV1-P24 monoclonal was quite poor compared with Anti-HIV1/2 P24. The P24 protein presented as a fusion with β-barrel scaffold gave excellent results on both types of plates with both antibodies. The results were much better than expected compared to the native P24 and there was no non-specific binding to the scaffold by itself (OMP171). These data indicate that the P24 bound to the surface via the β-barrel scaffold anchor is highly functional for antibody recognition compared to native P24, most likely owing to presentation of the correct structure in an active, accessible orientation. The beneficial effect is much greater than we expected or thought possible. Thus the β-barrel scaffold technology fulfils the critical requirements of retention of function of the fusion partner when immobilized on the surface and improves significantly on current state-of-the art techniques.

Modified β-Barrel Scaffold for the Display of Small Peptide Motifs

The display of small peptide motifs of 3-50 amino acids presents a different challenge compared to larger proteins. They may not be elevated enough from the surface and might remain hidden and inaccessible among the bulk protein. This is a disadvantage since one of the main applications for small motif display is in cell culture where the motif needs to be exposed enough to interact with components of the cell envelope. To this end we have designed a scaffold backbone that allows the insertion of small motifs on an elongated loop with hydrophilic amino acids and a semi-rigid PT linker (OMP154-type). The PT linker is a naturally occurring amino acid sequence (Poon, D. K. Y. et ai. (2006) Direct Demonstration of the Flexibility of the Glycosylated Proline-Threonine Linker in the Cellulomonas fimi Xylanase Cex through NMR Spectroscopic Analysis, *J Biol Chem* 282: 2091-2011)

Construction and Purification of Fusion Proteins

The OMP0 scaffold protein was modified to remove three of the four extracellular loops, the basic modified scaffold was named OMP154. The differences between OMP0 and OMP154 shown in the alignment of FIG. 14.

The gene encoding OMP154 was synthesized at IDT and cloned and verified using standard molecular biology procedures (Sambrook, supra) and purified using our standard methods (see General Methods below below).

Once the OMP154 backbone scaffold protein was completed, various insertions were made into it as shown in Table 3.

TABLE 3

List of new proteins with motifs displayed in the long loop of OMP154

| Protein Name | Insertion details |
|---|---|
| OMP153 | 154 with RGDS in (SEQ ID NO: 25) long loop |
| OMP162 | 154 with IKVAV (SEQ ID NO: 26) from laminin α1 in long loop |
| OMP163 | 154 with YIGSR (SEQ ID NO: 27) from laminin β1 in long loop |
| OMP164 | 154 with 2xPHSRN (SEQ ID NO: 28) in long loop |
| OMP165 | 154 with Collagen IV- MNYYSNS (SEQ ID NO: 29) in long loop |
| OMP174 | 154 with two FHRRIKA (SEQ ID NO: 30) motifs from in collagen tandem in long loop |
| OMP175 | 154 with IPKASSVPTELSAISMLYLDENEKVVLK (SEQ ID NO: 31) from human BMP2 protein in long loop |
| OMP176 | 154 with PQVTRGDVFTMP (SEQ ID NO: 32) from human vitronectin in long loop |
| OMP177 | 154 with KKQRFRHRNRKGYSRQ (SEQ ID NO: 33) from human vitronectin in long loop |

TABLE 3-continued List of new proteins with motifs displayed in the long loop of OMP154

| Protein Name | Insertion details |
|---|---|
| OMP178 | 154 with VDTYDGRGDSVVYGLRSKSKKFRR (SEQ ID NO: 34) from human osteopontin in long loop |
| OMP179 | 154 with VFDNFVLK (SEQ ID NO: 35) motif from human Tenascin-C in long loop |
| OMP185 | 154 with Collagen I GTPGPQGIAGQRVV (SEQ ID NO: 36) motif in long loop |
| OMP186 | 154 with Hiv TAT SYGRKKRRQRRRAHQ (SEQ ID NO: 37) motif in long loop |
| OMP187 | 154 with VQLRNGFPYFSY (SEQ ID NO: 38) from laminin α2 in long loop |
| OMP188 | 154 with GLLFYMARINHA (SEQ ID NO: 39) from laminin α2 in long loop |
| OMP189 | 154 with IKVSV (SEQ ID NO: 340) from laminin α2 in long loop |

These proteins were created either by gene synthesis of the complete coding sequence or by insertion of small double stranded oligonucleotide cassettes encoding the motif of interest into the cloning site in the middle of the loop in pOMP154 expression plasmid using standard methods (Sambrook, supra). The proteins were expressed and purified as described in section entitled General Methods below.

Immobilisation of Small Peptide Motifs on Polystyrene

Protein at 1 µM was prepared in PBS containing dilute detergent solution as before. This was added to each well of a well plate as before. After 16 hours each well was washed twice with sterilized 200 µL deionized water to remove excess unattached protein.

Culture of MG63 Cells on Small Peptide Motif Treated Plates

The protein treated 96 well plate was sprayed with 70% ethanol and left in a cell culture for 10 minutes for the ethanol to evaporate. Each well was then washed with D-PBS to remove any unevaporated ethanol. MG63 osteosarcoma cells (passage 5) were grown until ~80% confluent before they were harvested with trypsin/EDTA. Cells were resuspended in DMEM (containing 10% foetal calf serum) at $1 \times 10^4$ cells per mL. 100 µL cell suspension was added to each well of the 96 well plate, the plate was then incubated for 16 hours at 37° C., 5% $CO_2$ in a humidified cell culture incubator.

Quantification of Cells Cultured on Small Peptide Motif Treated Plate.

A PNPP assay was used to provide semi-quantitative assessment of the number of attached cells in each well using the intracellular acid phosphatases to create a colour change in the PNPP reagent. PNPP reagent was prepared by dissolving 1 mg per ml PNPP (Sigma Lot.SLBC5466V) in PNPP reagent buffer (0.1M Sodium acetate pH5 +0.1% Triton X-100; Lot.220113SP). The cell media was removed from all the wells, 100 µL PNPP reagent was added to each well, the 96 well plate was wrapped in aluminium foil and incubated at 37° C. for 2 hours. The reaction was stopped by the addition of 10 µL 1M NaOH (Lot.021111DS) to each well. After gentle shaking 85 µL was transferred from each well to a new 96 well plate and the absorbance at 405 nM was measured using a Thermo Fisher Multiskan FC plate reader.

The results are in line with what we would predict with a wide range of effects from the different proteins, OMP154 improves cell attachment compared to the blank well by reducing the hydrophobicity of the surface and thus making it easier for the cells to attach. A similar level of improvement is seen with a large percentage of the tested proteins. MG63 cells show enhanced cell attachment, compared to OMP154, when grown on the surfaces OMP153, 177 and 178. OMP153 displays the RGDS motif found in fibronectin, vitronectin, osteopontin, etc and is a very powerful integrin binding motif that interacts with many different cell types. OMP177 and 178 both display vitronectin motifs, an ECM component found in mineralised bone. The results clearly show that the OMP154 based proteins display their engineered motifs in such a way that they are accessible for cells to interact with. With several of the tested proteins significantly enhancing the attachment of the osteosarcoma cell line MG63.

OMP140-Type Scaffolds Fused to Growth Factors

In order to exemplify the significant advantages of the technology for the presentation of immobilized growth factors on tissue culture plates, we created variants of the OMP140-type β-barrel proteins fused to various growth factor as listed in Table 4. ORL140 is a scaffold protein with truncated extracellular loops and truncated C-terminus. It has the his tag at the C-terminus which ensures that only full length expressed proteins carry the his tag and can be purified by metal affinity chromatography. This allows the fusion of large proteins such as growth factors and alleviates concerns about premature translational stops that can occur when overexpressing large proteins. It also has the cysteine residue removed. Most growth factors have numerous internal disulphide bridges that are essential for the maintenance of structure and function; cysteine present in the scaffold could interfere with the formation of these specific disulphide bridges and the cysteine-free variant of the scaffold alleviates this problem.

Note that apart from the C-terminal His-tag, the lack of cysteine residue, and the lack of the C-terminal NQ residues, OMP140 is identical to OMP171 (see FIG. 9)

Construction and Purification of Fusion Proteins

The OMP140 coding sequence was synthesized by IDT and cloned into the expression vectors using standard methods (samboork, supra). A series of novel fusion proteins with OMP140 were created by ligating synthetic cassettes (designed at OMP and codon optimised for E. coli) coding for growth factors into the pOMP140 such that they were at the N-terminus of the fusion proteins. A list of constructs created to date is shown in Table 4.

TABLE 4

Fusions of growth factors to OMP140

| Protein Name | Insertion details |
|---|---|
| pOMP167 | Human epidermal growth factor in OMP140 |
| pOMP180 | Human Leukaemia Inhibitory Factor (LIF). Amino acids 23 to 30 of P15018 in UniProt (SPLPITPV SEQ ID NO: 41). Isoform 1. fused to N-terminus of OMP140 |

TABLE 4-continued

Fusions of growth factors to OMP140

| Protein Name | Insertion details |
|---|---|
| pOMP181 | Human fibroblast growth factor 4 (FGF-4). Amino acids 31-206 of P08620 in UniProt (APTAPNGTLE AELERRWESL VALSLARLPV AAQPKEAAVQ SGAGDYLLGI KRLRRLYCNV GIGFHLQALP DGRIGGAHAD TRDSLLELSP VERGVVSIFG VASRFFVAMS SKGKLYGSPF FTDECTFKEI LLPNNYNAYE SYKYPGMFIA LSKNGKTKKG NRVSPTMKVT HFLPRL SEQ ID NO: 42). Isoform 1. fused to N-terminus of OMP140 |
| pOMP182 | Human Interleukin-4 (IL-4). Amino acids 25-153 of P05112 HKCDIT LQEIIKTLNS LTEQKTLCTE LTVTDIFAAS KNTTEKETFC RAATVLRQFY SHHEKDTRCL GATAQQFHRH KQURFLKRL DRNLWGLAGL NSCPVKEANQ STLENFLERL KTIMREKYSK CSS (SEQ ID NO: 43) Isoform 1. fused to N-terminus of OMP140 |
| pOMP183 | Human stem cell factor (SCF). Amino acids 26-190 of P21583 (also known as 'Soluble Kit ligand' fused to N-terminus of OMP140 EGICR NRVTNNVKDV TKLVANLPKD YMITLKYVPG MDVLPSHCWI SEMWQLSDS LTDLLDKFSN ISEGLSNYSI IDKLVNIVDD LVECVKENSS KDLKKSFKSP EPRLFTPEEF FRIFNRSIDA FKDFVVASET SDCWSSTLS PEKDSRVSVT KPFMLPPVAA (SEQ ID NO: 44) |
| pOMP184 | Human Sonic Hedge Hog (Shh). Amino acids 24-197 of Q15465 fused to N-terminus of OMP140 (CGPGRGF GKRRHPKKLT PLAYKQFIPN VAEKTLGASG RYEGKISRNS ERFKELTPNY NPDIIFKDEE NTGADRLMTQ RCKDKLNALA ISVMNQWPGV KLRVTEGWDE DGHHSEESLH YEGRAVDITT SDRDRSKYGM LARLAVEAGF DWVYYESKAH IHCSVKAENS VAAKSGG (SEQ ID NO: 45) |
| pOMP190 | Human granular macrophage colony stimulating factor (GM-CSF). Amino acids 18-144 of P04141 fused to N-terminus of OMP140 APA RSPSPSTQPW EHVNAIQEAR RLLNLSRDTA AEMNETVEVI SEMFDLQEPT CLQTRLELYK QGLRGSLTKL KGPLTMMASH YKQHCPPTPE TSCATQIITF ESFKENLKDF LLVIPFDCWE PVQE (SEQ ID NO: 46) |
| pOMP191 | Human interleukin 3 (IL-3). Amino acids 20-152 of P08700 fused to N-terminus of OMP140 (A PMTQTTPLKT SWVNCSNMID EIITHLKQPP LPLLDFNNLN GEDQDILMEN NLRRPNLEAF NRAVKSLQNA SAIESILKNL LPCLPLATAA PTRHPIHIKD GDWNEFRRKL TFYLKTLENA QAQQTTLSLA IF (SEQ ID NO:47) |
| pOMP192 | Human Thrombopoeitin (TPO). Amino acids 23-195 of P40225 fused to N-terminus of OMP140 PAPPACDL RVLSKLLRDS HVLHSRLSQC PEVHPLPTPV LLPAVDFSLG EWKTQMEETK AQDILGAVTL LLEGVMAARG QLGPTCLSSL LGQLSGQVRL LLGALQSLLG TQLPPQGRTT AHKDPNAIFL SFQHLLRGKV RFLMLVGGST LCVRRAPPTT AVPSRTSLVL TLNEL (SEQ ID NO. 48) |

The proteins were expressed and purified as described in Section 3.1 but the refolding conditions for them varied: The standard refolding buffer was supplemented with 1 mM DTT and 0.4 M arginine.

General Methods
Protein Purification and Refolding

OMP proteins were expressed as inclusion bodies in *E. coli* BL21 strain by IPTG induction in 1 liter of LB selective medium. The cells were lysed in BugBuster solution (Novagen) and inclusion bodies enriched using the wash protocols in the Instruction Manual for BugBuster.

Inclusion bodies were solubilised in HTBB buffer (20 mM NaPO$_4$, 0.5 M NaCl, 20 mM Imidazole, 8 M Urea pH7.4, filtered and degassed). The solubilised preparations were purified by immobilized metal affinity chromatography on HisTrap HP columns (GE Healthcare) on an AKTAPrime system with fraction collector using a pre-programmed binding-wash-elution method—the elution was a step elution in HTBB+250 mM Imidazole. The peak fractions from the elution were collected and purity determined by SDS PAGE. Fractions deemed to be >95% homogenous for the protein of interest were pooled and concentrated using a Vivaspin centrifugal concentrator to volume of <1 mL. The purified protein was refolded by dilution (by a factor of at least 1 in 10) into refolding buffer (50 mM Ethanolamine, 0.1 mM EDTA, 1% OG, 1 mM DTT).

The extent of refolding was estimated by bandshift on SDS PAGE and further verification carried out where necessary by circular dichroism spectroscopy and functional assays (not shown here).

SDS PAGE

The NuPAGE SDS PAGE gels, buffers and stains from Invitrogen were used according to manufacturer's instruction.

Effect of Detergent on Binding of OMP18

In order to test the effect of detergent we looked at some commonly used detergents in biology for their suitability in allowing OMPprotein to bind to polystyrene surfaces.

| Detergent | MW | Critical Micelle Concentration (CMC) |
|---|---|---|
| n-octyl glucoside (OG) | 292 | 20-25 mM |
| n-dodecylmaltoside (DM) | 511 | 0.15 mM |
| Nonaethyleneglycolmonododecylether (Thesit, Polidocanol) | 583 | 0.1 mM |

In order to gain a realistic comparison of detergents we used the CMC as the factor to determine concentration for example OG at 22.5 mM was defined as 1xCMC or DM at 0.3 mM was defined as 2xCMC etc.

In the first experiment all three detergents were used at various concentrations around the CMC to immobilize OMP18 for 6 or 24 h and carried out the immunodetection as above.

OMP18 protein at 1 µM concentration was prepared in PBS containing 2×CMC of detergent. This was added to wells of a 96-well plate in a series of dilutions to give 2×, 1×, 0.5× and 0.25×CMC for each detergent.

One set of wells was washed and processed after 6 hours and a second set was incubated for 24 hours. Following washing a drying, the immunoassay was carried out as described above but with a single mouse IgG concentration at 1 µg/mL.

Figure 22:
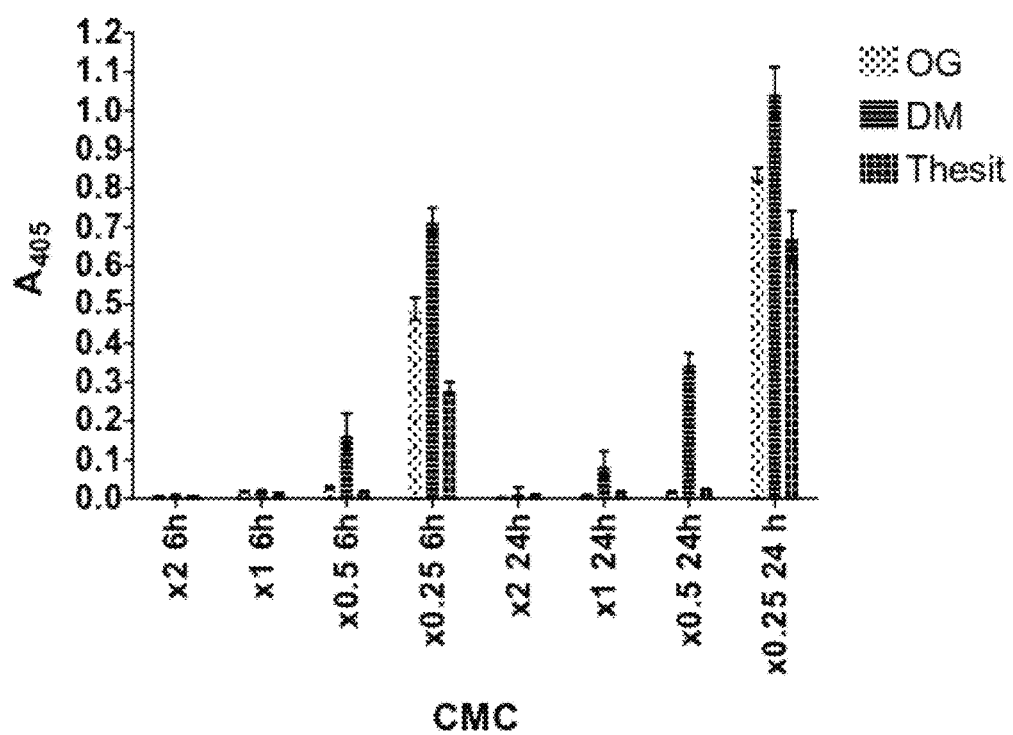
FIG. 22 shows the immobilisation of protein at different detergent concentrations. The OMP18 protein (at a final 0.1 μM) was diluted in the detergent concentration shown in 96 well plates. One set of wells was washed and dried after 6 h whereas adsorption was allowed to proceed for 24 h in the second set of wells. After washing the surfaces were probed with mouse IgG and detected with anti-mouse AP conjugate and PNPP substrate colorimetric reaction. The best result was obtained with OMP18 in DM at 0.125×CMC adsorbed for 24 h.

The data is shown graphically in FIG. 22.

At high detergent concentration at CMC or above there is little binding of protein to the surface as indicated by the low signal from the immunoassay. In all cases precipitation was not observed at the lowest detergent concentration.

In each case the 6-24 h incubation with Orla protein gave the optimum result.

Effect of OMP18 Concentration

This experiment aimed to determine the effect of OMP18 concentration on surface performance. It may be useful to limit the amount of protein on the surface for certain applications and the ability to control the surface density would be desirable.

OMP18 was diluted at different concentrations in detergents at 0.125×CMC in PBS buffer in wells of a 96 well untreated polystyrene plate. Each well had 200 µL of solution and the plate was incubated at 4° C. overnight. After washing and drying the immunodetection was carried out as above with mouse IgG at 1 µg/mL.

Figure 23:
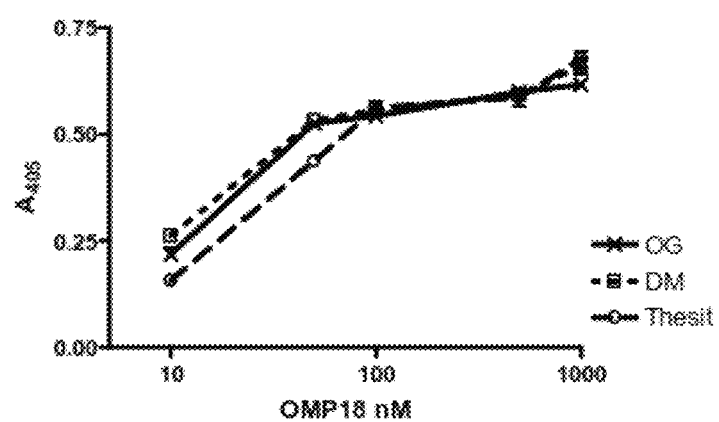
FIG. 23 shows the degree of saturation of the protein on the substrate. Effect of OMP18 concentration. Omp18 was diluted to different final concentrations in detergent at 0.125×CMC and adsorbed for 24 h. Mouse IgG binding assay was carried out as described herein. The results demonstrate that the surface was almost saturated at 100 nM (0.1 μM) protein in all the detergents and this was chosen as the standard concentration for adsorption.
Figure 24:
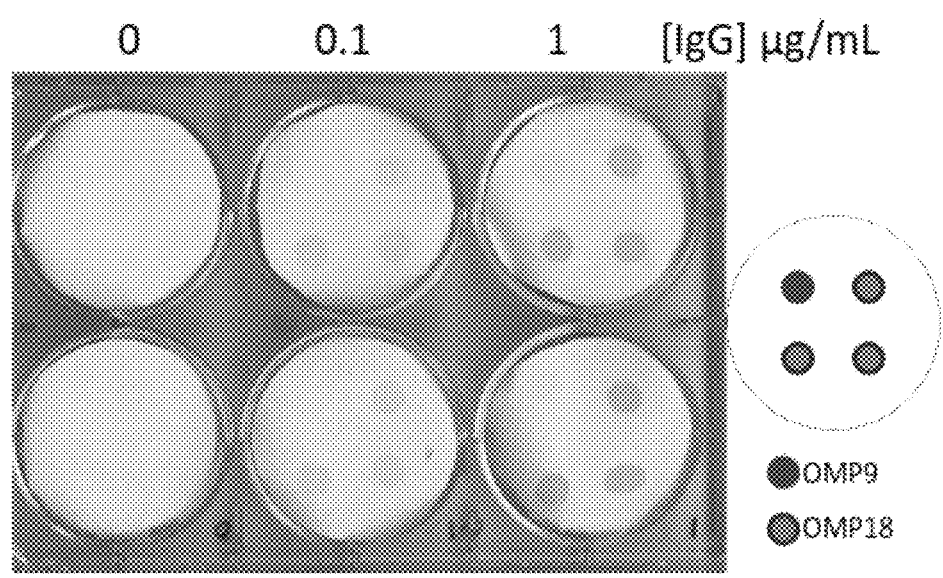
FIG. 24 is a scan of OMP9 and OMP18 spotting experiment. White paper plugs were placed in each well to obtain a clear scan of the bottom of the well.

The data are shown graphically in FIG. 23.

The data show that the surfaces are close to saturation with the addition of protein at 100 nM and that it is possible to control the coverage by varying the protein concentration (and the detergent concentration as shown above).

Pattern Spotting on Surfaces

It would be useful to create patterns of protein on surfaces for numerous applications such as arraying, cell culture, drug discovery, and so on. The method described herein should be amenable to printing and patterning.

10 µL spots of OMP9 (control protein) and OMP18 (IgG-binding domains on OMP9 scaffold) were pipetted onto the bottom of 6 well polystyrene plates and adsorbed overnight on a humidity chamber at RT (the spots did not dry overnight under these conditions).

The proteins were at a final concentration of 5 µM in detergent at 0.4×CMC in each spot.

The wells were washed 2×2 mL TBS-T and once with water and dried.

Blocked with 2 mL TBS-T+3% BSA for 1 h.

Then 1 mL of mouse IgG at 0, 0.1 or 1 µg/mL in TBS-T+3% BSA was added to each well and incubated for 15 min.

After 3×2 mL washes with TBS-T, 1 mL of anti-mouse IgG-AP conjugate 1/10000 dilution was added and incubated at RT for 15 min.

The wells were washed 3×2 mL TBS-T and once with water.

BCIP/NBT substrate was added (0.5 mL) and incubated for 15 min at RT.

Reaction was stopped by washing 3×2 mL water and the wells were dried.

Figure 25:
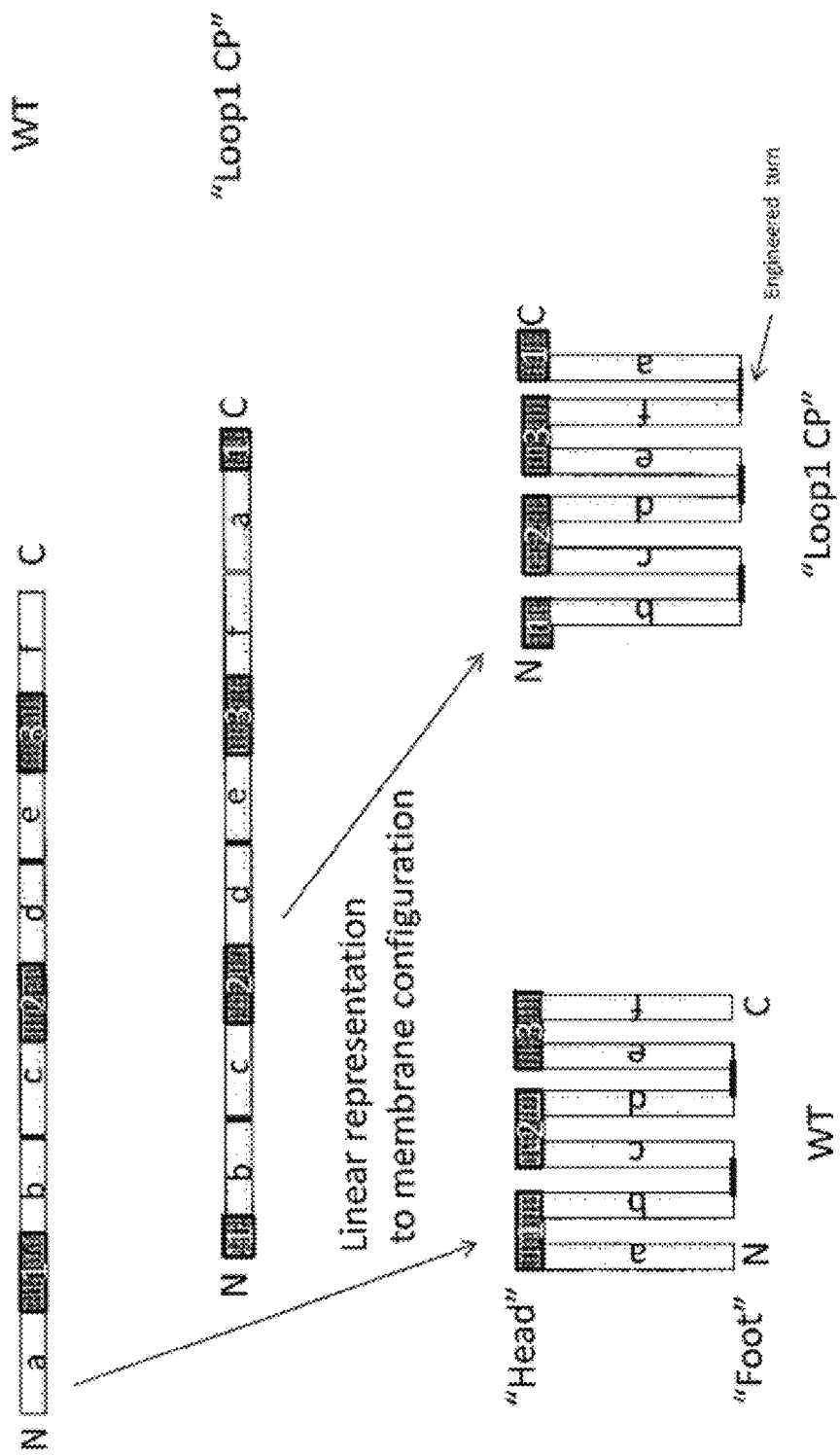
FIG. 25 shows a hypothetical 6 stranded barrel protein. Circular permutation results in repositioning of the N- and C-termini and the beta strand.

A scan of the plate is shown in FIG. 25. The dark shadows indicate areas where protein was bound. These correspond to where the spots were placed.

In this case, the 10 µL of solution spread out into spots with an average diameter of 5.5 mm. This spot size would be good for cell culture applications. It should be possible to create smaller spots by using lower volume of protein at higher concentration. Note that there is normally some cross reactivity of polyclonal antibodies with OMP9.

These data suggest that the method for immobilizing OMP proteins on a surface should be amenable to more precise and sophisticated patterning and lithographic techniques.

Functionalisation of Polystyrene Beads with Omp Proteins

We have demonstrated improved function of OMP proteins on planar plastic surfaces and it was desirable to test if these advantages and improvements in function could be reproduced on particles and beads that are important in many applications such as bioprocessing. In order to exemplify this we coated polystyrene beads with OMP85 protein (Protein G domains fused to the Omp scaffold) or Staphylococcal protein A in its native form and attempted to purify IgG from human serum using the coated beads as the capture agent.

Polybeads of 1 µm diameter were obtained from Polysciences Inc. A suspension of 0.5 g of polybeads was made in 20 mL of PBS+0.01% SDS to give a preparation containing 2.5% solids i.e. $4.55 \times 10^{10}$ particles/mL. The binding of Protein A or OMP85 to the polybeads was carried out in 2 mL final volumes of PBS containing 1 mL of 2.5% polybeads, 0.5 mg of protein and dodecylmaltoside (DM) at a concentration of 0.125×CMC. An additional 'untreated' sample was prepared by mixing 1 mL of polybeads and 1 mL of PBS. All were left overnight at 4° C. after mixing thoroughly. The polybeads were centrifuged and washed 3× by resuspension in 1 mL of TBS-T and centrifugation. Then each pellet was resuspended in 0.5 mL of TBST and 0.5 mL of human serum were added and incubated for 10 min at RT. The polybeads were centrifuged and the pellets washed 4×1 mL TBS-T. Supernatants were saved for analysis on SDS PAGE. Bound IgG was eluted by resuspension of the washed pellets in 1 mL 50 mM Na-acetate pH2.5 followed by immediate centrifugation and neutralisation of supernatant with 50 µL of 3 M NaOH.

Figure 26:
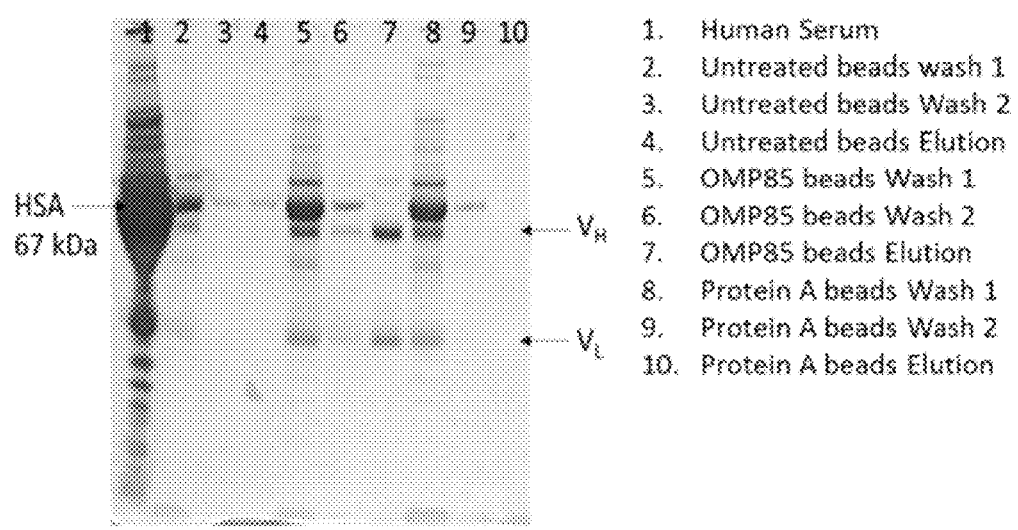
FIG. 26 shows SDS PAGE analysis of samples from polybead experiment. 5 μL of human serum loaded in Lane 1, all other lanes 20 μL out of a 1 mL sample loaded. HSA is human serum albumin. $V_H$ is the heavy chain of IgG at ~50 kDa and $V_L$ is the light chain at ~25 kDa. The samples were in SDS loading dye with 1 mM DTT and heated for 5 min at 95° C.

Samples were analysed on SDS PAGE as shown in FIG. 26. SDS PAGE analysis of samples from polybead experiment. 5 µL of human serum loaded in Lane 1, all other lanes 20 µL out of a 1 mL sample loaded. HSA is human serum albumin. $V_H$ is the heavy chain of IgG at ~50 kDa and $V_L$ is the light chain at ~25 kDa. The samples were in SDS loading dye with 1 mM DTT and heated for 5 min at 95° C. There is no IgG in the elution from untreated beads whereas OMP85 treated beads contained purified IgG in the elution. Protein A treated beads also had purified IgG but in such small quantities that they are not visible in the gel scan shown above. This clearly demonstrated that OMP85 can bind to polybeads and is highly functional for IgG binding.

Durability of the Protein Coated Surfaces to Washing with Various Agents

Figure 27:
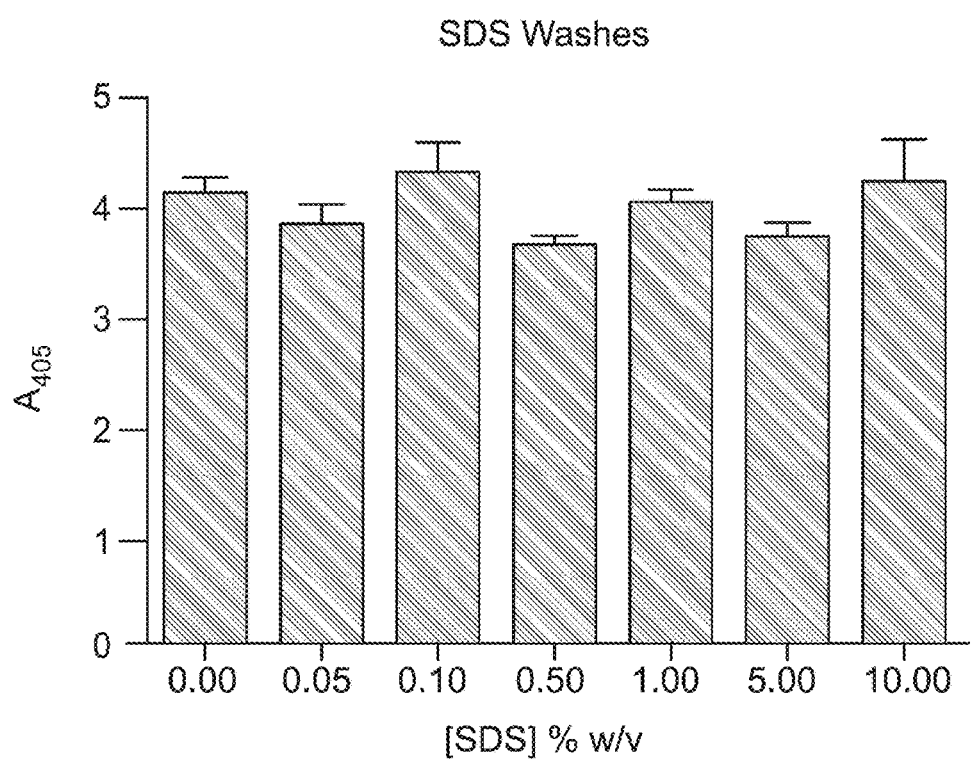
FIG. 27 shows the 0% SDS wells were washed with SDW. All washes carried out in triplicate and data shown is the average of three wells. There is a very high reading of greater than 3 $A_{405}$ units because the reaction with the PNPP substrate solution was allowed to carry on for 15 min.

In order to examine the durability of surfaces coated with the modified Omp proteins we tested the resilience of the coated surfaces to commonly used washing and cleaning agents. Well plates were coated with omp protein using the standard protocol and then washed with the cleaning agent followed by immunodetection as described before. In the preliminary experiment wells coated with OMP203 were washed with different concentrations of SDS for 5 min and detection with anti-FLAG monoclonal antibody conjugated to alkaline phosphatase was carried out. The results are shown in FIG. 27.

The 0% SDS wells were washed with SDW. All washes carried out in triplicate and data shown is the average of three wells. There is a very high reading of greater than 3 $A_{405}$ units because the reaction with the PNPP substrate solution was allowed to carry on for 15 min. Conclusion: SDS did not remove significant quantities of proteins indicating that once the proteins are attached to the plastic surface, they are not displaced by strong detergent.

Figure 28:
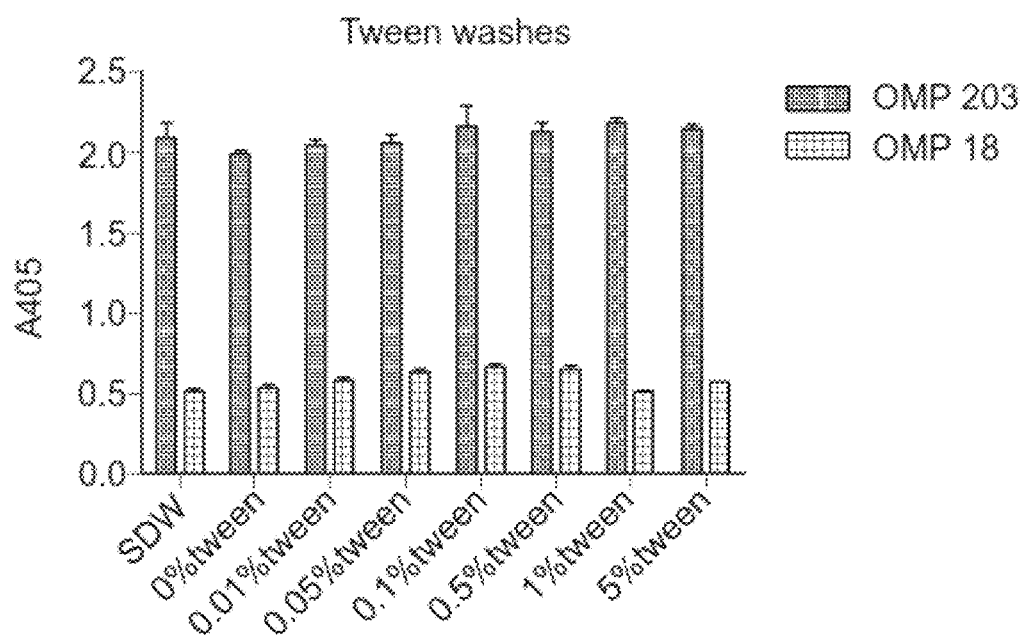
FIG. 28 shows the detection of OMP203 and OMP18 after washing with Tween™. Tween 20 was used.
Figure 29:
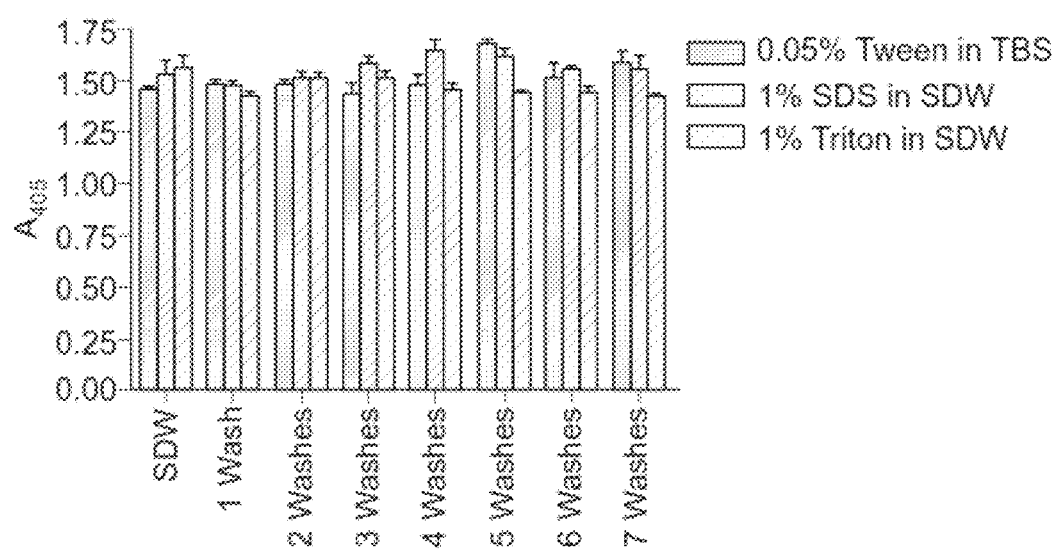
FIG. 29 shows the effect of washing frequency on immunoassay signal. Tween™ 20 was used. The incubation with PNPP was carried out for 5 min at room temperature.

A similar experiment was carried out on wells coated with OMP203 and OMP18 but this time different concentrations of Tween 20 were used. The data are shown in FIG. 28. Again the proteins proved resilient against washing with Tween 20. Since most standard ELISA protocols require multiple detergent washes, the effect of 1-7 cycles of washing was tested. OMP203 coated wells were washed with varying numbers of washes of detergent-containing solutions (Book 59 p44, p55). One set of three wells was washed with water (SDW) whilst other wells were washed up to 7 times with detergent. The data are shown in the FIG. 29.

A variety of other wash conditions was also tested. Plates were coated with either OMP18 or OMP203. This time the wells were incubated for 15 min at RT with the test wash solution before washing with water and completing the detection assay as above. Note that the OMP18 assay required the binding of mouse IgG followed by detection with anti-mouse AP conjugate. The results are shown in FIG. 30. Data from immunoassay after washing with various agents as shown under the X-axis. DMSO is dimethylsulphoxide; Arg—arginine; OG—octylglucoside; EDTA is ethylene diamine tetra acetic acid; Hellmanex™ II was used. Note that untreated wells were washed only with water. Each data point is the average of readings from 3 wells. None of the wash conditions tested could remove significant quantity of the protein from the surface.

Figure 31:
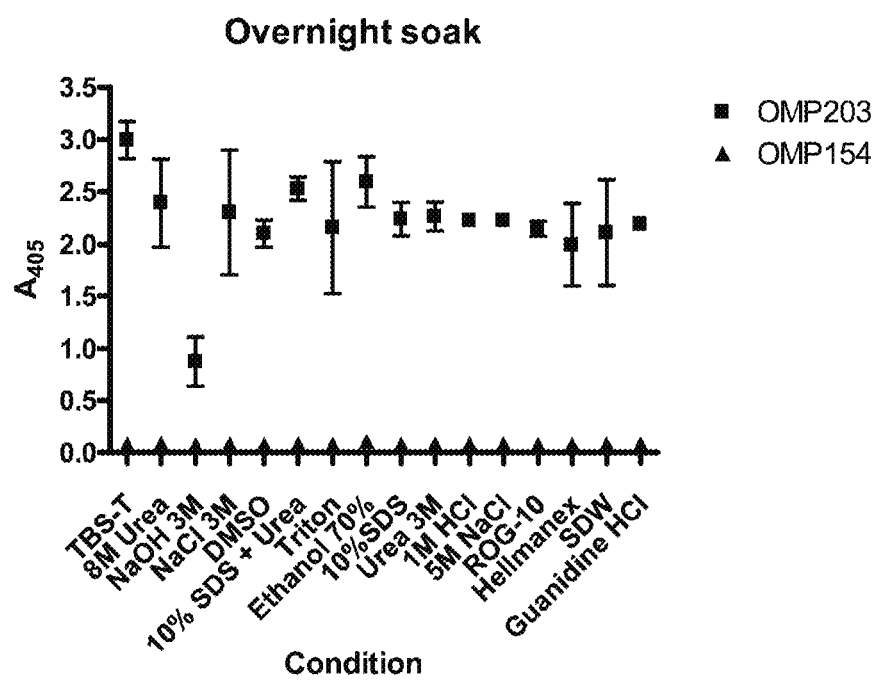
FIG. 31 shows the absorbance readings from detection of OMP203.

This data demonstrates the resilience of omp proteins bound to polystyrene in the face of washing with harsh agents such as HellmanexII®, strong acids, strong bases, chaotrophs such as urea and arginine and common detergents and solvents. The binding of the OMP proteins to polystyrene is very robust and hard to displace. In order to test the effects of longer-term exposure to washing agents, plates coated with OMP203 were incubated overnight with washing agents and analysed by immunoassay with anti-FLAG-AP conjugate. The results are shown in the FIG. 31.

The readings were again very high and above the saturation limit for the plate reader. However, compared to previous data there is a greater degree of variation between wells and the 3M NaOH soak has a markedly reduced signal indicating that 3M NaOH soak has removed or destroyed surface bound protein. Nevertheless, the surface bound OMP203 protein demonstrated an extraordinary resilience in overnight soak in all the other agents including harsh wash buffers such as neat HellmanexII, 6M GuHCl, 8M urea, 1% TritonX100.

Enhanced Attachment of Cells to Orla Protein Coated Polystyrene

OMP proteins displaying various extra-cellular matrix (ECM) derived motifs (see table overleaf) were coated in triplicate wells of a Sarstedt hydrophobic 96 well plate using our standard protocol. The plates were sprayed with 70% ethanol and placed in a cell culture cabinet, after 10 minutes the remaining ethanol was discarded and each well was washed with 200 μL Dulbecco's Phosphate buffered saline. MG63 human osteosarcoma cells were harvested from a 75 cm² cell culture flask using trypsin and seeded onto the protein coated wells, 200 μL cell suspension containing $1\times10^4$ cells per mL was added to each well. The cells were incubated overnight in a humidified cell culture incubator at 37° C.

TABLE 6

Details of the proteins tested with MG63 cells, all the proteins are based on the OMP154 protein with insertions of different sizes in the same elongated loop.

| Protein | Motif | No. of Amino acids | Source of motif |
|---------|-------|--------------------|-----------------| 
| OMP154 | Control protein | 0 | N/A |
| OMP153 | RGDS (SEQ ID NO: 25) | 4 | Fibronectin |
| OMP162 | IKVAV (SEQ ID NO: 26) | 5 | Laminin α1 |
| OMP164 | PHSRN (SEQ ID NO: 28) | 5 | Fibronectin |
| OMP203 | Variable (CS3) domain | 110 | Fibronectin |

After 16 hours incubation the number of attached cells in each well was assessed using an acid phosphatase assay. In this assay the cells are disrupted with an acidic buffer containing detergent this exposes the acid phosphatase within the cells, the enzyme converts colourless para-nitrophenylphosphate (Pnpp) to the yellow compound para-nitrophenol. More cells in a well will cause an increase in the conversion of Pnpp to para-nitrophenol which can be easily be detected by measuring the absorbance of light at 405 nm.

The media was removed from each well and 100 μL 0.1M sodium acetate pH5 containing 0.1% Triton X-100 and 1 mg/mL Pnpp was added to each well. The plate was wrapped in aluminium foil and incubated at 37° C. for 2 hours. The reaction was terminated by the addition 10 μL 1M NaOH to each well. 85 μL solution from each well was transferred to a new 96 well plate and the absorbance at 405 nm was measured using a plate reader (Book 58 pp 10-25).

Figure 32:
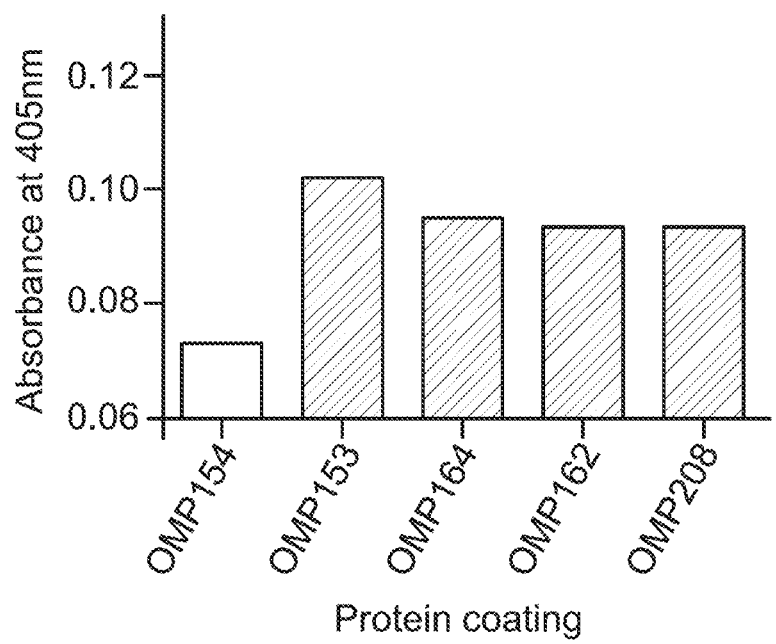
FIG. 32 shows results of culture of MG63 cells on polystyrene coated with OMP proteins displaying various ECM motifs.

FIG. 32 shows the results of culture of MG63 cells on polystyrene coated with Orla proteins displaying various ECM motifs.

Conclusions; OMP proteins displaying ECM motifs of different sizes and from different ECM proteins are able to increase the number of attached MG63 cells compared to wells coated with the control OMP154 protein.

Protein Functionalisation of 3D Polystyrene

Figure 33:
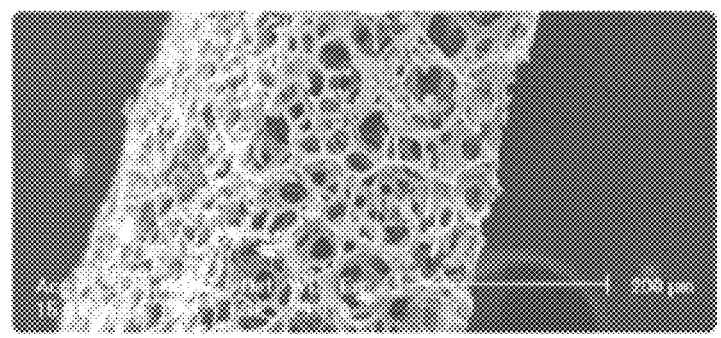
FIG. 33 is an electron micrograph of the porous 3D structure of Alvetex.

The standard polystyrene coating protocol used for polystyrene plates can be adapted to protein coat other polystyrene materials such as the 3D cell culture material Alvetex, trademark of Reinnervate Ltd. (see FIG. 33)

Protein concentration used was raised from 1.6 μM to 15 μM to accommodate the increased surface area of the Alvetex (Book 52 pp 137-141). Three samples of Alvetex were treated with control ompA protein, three were treated with IgG binding protein OMP85. The treated samples were washed twice with 2 mL Tris Buffered Saline containing 0.05% Tween 20 (TBS-T). Alkaline phosphatase conjugated anti-mouse IgG was diluted 1:10,000 in TBS-T, 500 μL of diluted antibody was added to each Alvetex sample and incubated at room temperature for 1 hour. Each sample was washed twice with 500 μL TBS-T before adding 600 μL Para-nitrophenylphosphate (Pnpp) reagent. After 10 minutes the 1 mL Pnpp reagent was removed from each well and the absorbance at 405 nm was measured with a spectrophotometer.

Figure 34:
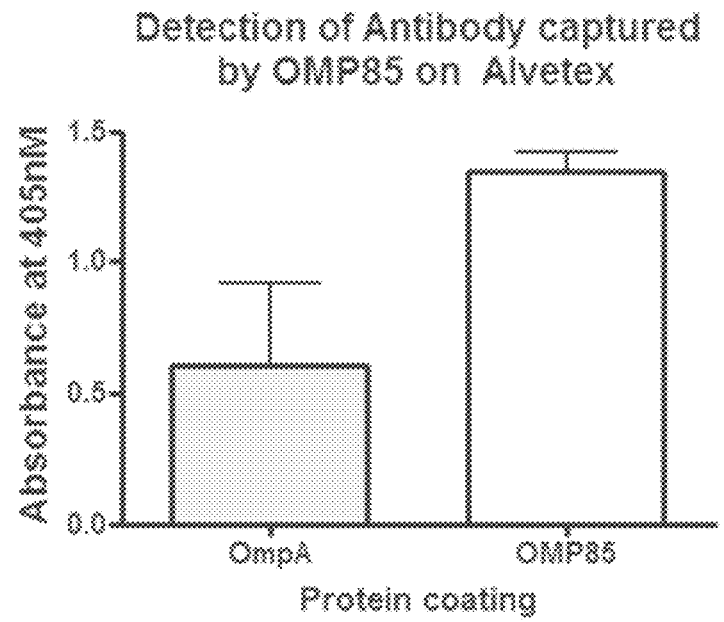
FIG. 34 shows results of detection of alkaline phosphatase conjugated IgG on 3D polystyrene treated with OMP proteins.

FIG. 34: Detection of alkaline phosphatase conjugated IgG on 3D polystyrene treated with OMP proteins.

Conclusion: Treating 3D polystyrene with OMP85 increases the binding of IgG compared to surfaces coated with the control ompA protein.

OMP proteins can be used to functionalise many different formats of polystyrene; 2D plates and flasks, beads and 3D structures.

Protein Attachment to Poly (Lactic Acid)

Most of the work to date has examined the use ompA proteins on various formats of polystyrene. The same method for protein attachment can be used to protein coat other materials such as poly lactic acid (PLA). In this example OMP5, ompA displaying the FLAG epitope, was immobilize on 3D printed PLA 3 mm×8 mm scaffolds using the same dilution method used for polystyrene (Book 58 pp 28-53).

FIG. 6 shows the cross hatch structure of the 3D printed 2 mm×8 mm PLA discs.

Eighteen PLA discs were treated with OMP5, ompA modified to display the FLAG epitope, this can easily be detected using an anti-FLAG antibody. A 32 µM solution of OMP5 was prepared, 37.5 µL protein and 562.5 µL phosphate buffered saline was added to each PLA disc. The discs were incubated overnight at 4-8° C., the following day they were washed three times with 500 µL sterile deionized water. The discs were split into six groups of three, each group was soaked in a 1% solution of Triton X-100 at 37° C. for a different number of days.

No treatment with Triton X-100
1 day in 1% Triton X-100
2 days in 1% Triton X-100
3 days in 1% Triton X-100
4 days in 1% Triton X-100
7 days in 1% Triton X-100

At each time point the 1% Triton X-100 solution was removed and replaced in all samples to prevent the reattachment of any protein removed from the samples.

At the end timepoint all discs were washed with 500 µL TBS-T then incubated in 500 µL containing 1 µL per mL M2 alkaline phosphatase conjugated anti-FLAG IgG for 30 minutes at room temperature. Each disk was washed three times with 500 µL TBS-T then transferred to a new 48 well plate. 500 µL Pnpp reagent was added to each disk, after 10 minutes at room temperature the reaction was terminated by the addition of 500 µL 1M NaOH.

200 µL Pnpp reagent was removed from each disc and placed into a 96 well plate, the absorbance at 405 nm of all the samples was measured using a plate reader.

Figure 35:
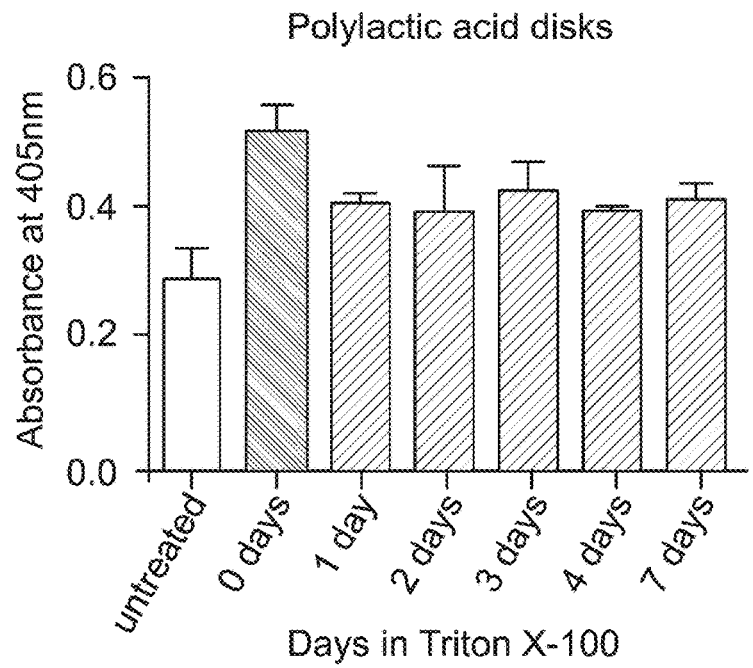
FIG. 35 shows antibody detection of the OMP proteins on PLA after several days immersion 1% triton X-100.

FIG. 35 shows antibody detection of the OMP proteins on PLA after several days immersion 1% triton X-100.

Conclusion: Treating PLA with OMP5 increases the binding of M2 anti-FLAG antibody to the PLA.

Soaking OMP5 treated PLA in 1% triton X-100 for 1 day decreases the binding of M2 anti-FLAG antibody to the PLA. Soaking the PLA in 1% triton X-100 for any longer does not further reduce the antibody binding.

Pre-Dilution of Protein

The method for binding of the omp scaffold to plastic surfaces relies upon the dilution of detergent. The standard protocols require dilution in situ i.e. the diluent is added to the surface first and then the protein solution is added to the diluent. This two-step process is difficult to achieve with precision for some techniques such as microdroplet or nanodroplet patterning. In this case it would be desirable to pre-dilute ex situ and apply to surface as a single droplet. We know that denatured omp protein cannot be directly diluted into detergent-free buffers because they precipitate and drop out of solution.

However, the effect of dilution of the refolded protein stored in detergent is not known. A series of experiments to test the effect of pre-dilution and short term storage were carried out.

a) Dynamic Light Scattering

A solution of 0.1 mg/mL of protein omp208 was prepared in PBS with 2×CMC (0.3 mM) of DM (dodecylmaltoside). The average particle size of the protein in this solution was determined to be 7.9 nm (±0.9 nm) by dynamic light scattering measurement on a Malvern Zetasizer-nano instrument.

Then a 20× dilution of 2 mg/mL solution of omp208 was made into a cuvette containing PBS and the average particle size was monitored over the course of 1 h. The experiment was carried out twice and three readings were taken at each time point. The data are shown in FIG. 36.

Figure 36:
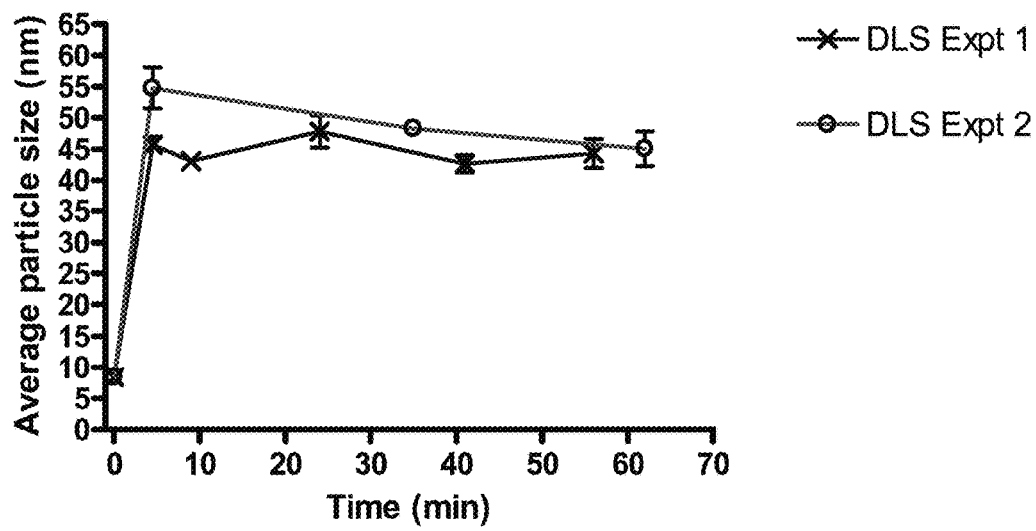
FIG. 36 shows data from the dynamic light scattering experiments. The plot shows the change in average particle size over the course of 1 hour.

FIG. 36 shows data from the dynamic light scattering experiments. The plot shows the change in average particle size over the course of 1 hour.

The data shows that after dilution the particle size increase from ~8 nm to 45-55 nm but thereafter was stable at this level for 1 h. These data indicate that there is some aggregation immediately after dilution but the aggregates are at a steady state of 45-55 nm for at least 1 h.

b) Immunoassay after Pre-Dilution

Figure 37:
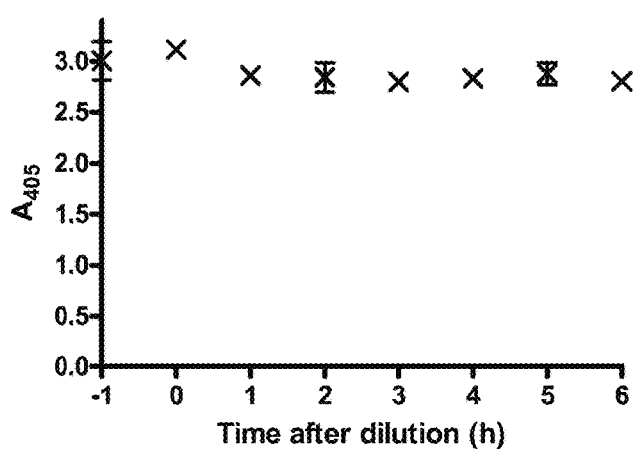
FIG. 37 shows the result of immunoassay of OMP203 detection after pre-dilution.

We tested whether pre-dilution affects the physisorption of the omp protein to plastic surface. A dilution of omp203 was made: 2 µM omp203, 0.1×CMC of DM in PBS. Immediately after dilution 200 µL of this were added to 3 wells of a 96-well untreated polystyrene plate (Time 0). Then at hourly intervals for up to 6 h, 200 µL samples were withdrawn from the pre-diluted solution and added to wells on the same plate, each time in triplicate. At 6 h a control set of wells was also prepared where the protein was diluted directly into the well as per standard protocol (this was plotted as the −1 sample in the graph of FIG. 38). FIG. 37 shows the result of immunoassay of omp203 detection after pre-dilution. The data shows that the ability of the protein to bind to plastics after pre-dilution remains unimpaired for at least 6 h.

TABLE 7

| Protein Name | Insertion details |
|---|---|
| OMP0 | OMP0 is the original gold-binding modified version of OmpA comprising truncated N- and C-termini, a 6xHis tag for affinity purification and a cysteine at residue 10, at the 'foot' of the protein for covalent bonding to gold. FIG. 13 |
| OMP5 | OMPA comprising a FLAG epitope (DYKDDDDK) in extracellular loop 1. |
| OMP9 | Modified version of OMP0. Shown in FIG. 1; comprises all extracellular loops, cysteine residue at residue 10 for gold binding; circularly permutated N and C termini and shortened N terminus |

TABLE 7-continued

| Protein Name | Insertion details |
| --- | --- |
| OMP13 | OMP9 with different endpoint N- and C-termini i.e. they are circularly permuted at different end points (FIG. 16). |
| OMP14 | OMP9 with different endpoint N- and C-termini i.e. they are circularly permuted at different end points (FIG. 17). |
| OMP18 | Tandem repeat of two IgG binding B domains of SPA fused to N terminus of OMP9 |
| OMP36 | OMP0 comprising the YIGSR motif from laminin in extracellular loop 1. |
| OMP59 | OMP59 is OMP9 with an alpha-helical spacer, is shown in FIG. 11 |
| OMP90 | OMP90 comprises FGF1 in an OMP59 scaffold |
| OMP128 | OMP128 comprises FGF 2 in an OMP59 scaffold |
| OMP140 | OMP9 with loops eliminated; His tag moved to C terminus. |
| OMP153 | 154 with RGDS in long loop |
| Omp154 | Modified version of OMP0. 3 truncated extracellular loops; loop 1 modified with a PT linker and lengthened with hydrophilic amino acids (See FIG. 14) |
| OMP162 | 154 with IKVAV from laminin α1 in long loop |
| OMP163 | 154 with YIGSR from laminin β1 in long loop |
| OMP164 | 154 with 2xPHSRN in long loop |
| OMP165 | 154 with Collagen IV- MNYYSNS in long loop |
| pOMP167 | Human epidermal growth factor in OMP140 |
| OMP170 | OMP171 lacking the alpha helical spacer is referred to herein as OMP170. |
| OMP171 | OMP9 with all extracellular loops truncated; the N terminus modified to include an alpha helical spacer sequence (mutated form of the *S. aureus* Protein A B domain which does not bind to IgG (the sequence of which is disclosed in Kim et al. (2010) Journal of experimental medicine Vol. 207 p 1863-1870) |
| OMP173 | A modified version of OMP171 wherein a protein (HIV antigen p24) is fused to the spacer. |
| OMP174 | 154 with two FHRRIKA motifs from collagen in tandem in long loop (SEQ ID NO: 30) |
| OMP175 | 154 with IPKASSVPTELSAISMLYLDENEKVVLK from human BMP2 protein in long loop (SEQ ID NO: 31) |
| OMP176 | 154 with PQVTRGDVFTMP from human vitronectin in long loop (SEQ ID NO: 32) |
| OMP177 | 154 with KKQRFRHRNRKGYSRQ from human vitronectin in long loop (SEQ ID NO: 33) |
| OMP178 | 154 with VDTYDGRGDSVVYGLRSKSKKFRR from human osteopontin in long loop (SEQ ID NO: 34) |
| OMP179 | 154 with VFDNFVLK motif from human Tenascin-C in long loop (SEQ ID NO: 35) |
| pOMP180 | Human Leukaemia Inhibitory Factor (LIF). Amino acids 23 to 20 of P15081 in UniProt. Isoform 1. fused to N-terminus of OMP140 |
| pOMP181 | Human fibroblast growth factor 4 (FGF-4). Amino acids 31-206 of P08620 in UniProt. Isoform 1. fused to N-terminus of OMP140 |
| pOMP182 | Human Interleukin-4 (IL-4). Amino acids 25-153 of P05112, Isoform 1. fused to N-terminus of OMP140 |
| pOMP183 | Human stem cell factor (SCF). Amino acids 26-190 of P21583 (also known as 'Soluble Kit ligand' fused to N-terminus of OMP140 |
| pOMP184 | Human Sonic Hedge Hog (Shh). Amino acids 24-197 of Q15465 fused to N-terminus of OMP140 |
| OMP185 | 154 with Collagen I GTPGPQGIAGQRVV motif in long loop (SEQ ID NO: 36) |
| OMP186 | 154 with Hiv TAT SYGRKKRRQRRRAHQ motif in long loop (SEQ ID NO: 37) |
| OMP187 | 154 with VQLRNGFPYFSY from laminin α2 in long loop (SEQ ID NO: 38) |
| OMP188 | 154 with GLLFYMARINHA from laminin α2 in long loop (SEQ ID NO: 39) |
| OMP189 | 154 with IKVSV from laminin α2 in long loop |
| pOMP190 | Human granular macrophage colony stimulating factor (GM-CSF). Amino acids 18-144 of P04141 fused to N-terminus of OMP140 |
| pOMP191 | Human interleukin 3 (IL-3). Amino acids 20-152 of P08700 fused to N-terminus of OMP140 |
| pOMP192 | Human Thrombopoeitin (TPO). Amino acids 23-195 of P40225 fused to N-terminus of OMP140 |
| OMP203 | Variable (CS3) domain |

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for immobilising a membrane spanning protein onto a polymeric substrate, the method comprising:
   i) providing a sample of a membrane spanning protein in a detergent;
   ii) providing a polymeric substrate;
   iii) incubating the protein sample of step i) with the polymeric substrate of step ii); and
   iv) during or after step iii), reducing the detergent concentration in the mixture of the protein sample and the polymeric substrate to 1× Critical Micelle Concentration (CMC) of the detergent or below;
   wherein the protein becomes immobilised upon the substrate by physisorption.

2. The method according to claim 1, wherein the detergent concentration is reduced to 0.05×CMC to 1×CMC.

3. The method according to claim 1, wherein the membrane spanning protein anchors, or is modified to anchor, a heterologous protein and/or peptide for display, wherein the anchored peptide and/or protein is spatially removed from the surface of the polymeric substrate.

4. The method according to claim 3, wherein the membrane spanning protein comprises a spacer to create a spatial distance between the membrane spanning protein and the peptide and/or protein for display.

5. The method according to claim 4, wherein the spacer is hydrophilic, rigid or semi rigid.

6. The method according to claim 5, wherein the spacer comprises an alpha helix, or a PT linker, or a glycine-serine spacer linker.

7. The method according to claim 4, wherein the spacer is heterologous to the membrane spanning protein and/or to the peptide and/or protein.

8. The method according to claim 1, wherein the membrane spanning protein:
   i) comprises a heterologous peptide and/or protein in a loop at a head of the protein or in a long loop between membrane spanning strands;
   ii) comprises a heterologous peptide and/or protein at an N and/or C terminus at a head of the protein;
   iii) comprises a heterologous peptide and/or protein at an engineered N and/or C terminus at the head of the protein; and/or
   iv) comprises a heterologous peptide and/or protein at an engineered N and/or C terminus at the head of the protein or in one or more loops provided at a head of the protein; and/or
   v) the N and/or C terminus of the membrane spanning protein are modified by circular permutation.

9. The method according to claim 8, wherein the membrane spanning protein is further engineered to:
   i) remove large internal or external domains which are not integral to the membrane;
   ii) truncate one or more loops; and/or
   iii) elongate one or more loops, for example with hydrophilic spacers to allow the insertion and display of proteins on the loops.

10. The method according to claim 1, wherein the membrane spanning protein is engineered for an N and/or C terminus to be provided i) in place of a loop; ii) adjacent to a loop; or iii) from within a loop.

11. The method according to claim 10, wherein the membrane spanning protein is an Outer Membrane Protein A, and the loop is loop 1, 3 or 4.

12. The method according to claim 10, wherein the membrane spanning protein is engineered for an N and C terminus to be provided in the same loop.

13. The method according to claim 1, wherein the membrane spanning protein is an integral membrane protein.

14. The method according to claim 13, wherein the membrane spanning protein is an Outer Membrane Protein (OMP) of Gram-negative bacteria.

15. The method according to claim 14, wherein the membrane spanning protein is OmpA.

16. The method according to claim 13, wherein the membrane spanning protein is selected from the group consisting of:
  i) OmpA modified to comprise 3 truncated extracellular loops, wherein Loop 1 is retained and comprises a PT linker;
  ii) OMP154 or a variant selected from the group consisting of OMP153, OMP162, OMP163, OMP164, OMP165, OMP174, OMP175, OMP176, OMP177, OMP178, OMP179, OMP185, OMP186, OMP187, OMP188, and OMP189;
  iii) a membrane spanning protein comprising a FLAG epitope (DYKDDDDK; SEQ ID NO: 19) in extracellular loop 1; or
  iv) a membrane spanning protein comprising a YIGSR motif from laminin (SEQ ID NO: 27) in extracellular loop 1.

17. The method according to claim 16, wherein Loop 1 further comprises hydrophilic amino acids.

18. The method according to claim 13, wherein the membrane spanning protein is OmpA modified to comprise i) all extracellular loops truncated; ii) the N and C termini positioned on the extracellular end (head) of the protein; or iii) a cysteine residue to enable binding of the protein to a gold surface.

19. The method according to claim 18, wherein the membrane spanning protein is OmpA modified to further comprise an alpha helical spacer at a terminus.

20. The method according to claim 13, wherein the membrane spanning protein is OmpA modified to comprise i) all extracellular loops truncated; ii) the N and C termini positioned on the extracellular end (head) of the protein; iii) the N terminus modified to include an alpha helical spacer sequence; iv) a His tag provided on the C terminus; or v) free of cysteine residues.

21. The method according to claim 13, wherein the membrane spanning protein is OmpA modified to comprise i) the N and C termini positioned on the extracellular end (head) of the protein; or ii) the N terminus truncated and fused to the IgG binding domain of Protein A of Staphylococcus aureus.

22. The method according to claim 13, wherein the membrane spanning protein is OMP140, a variant selected from the group consisting of pOMP167, pOMP180, pOMP181, pOMP182, pOMP183, pOMP184, pOMP190, pOMP191, and pOMP192, OMP90 comprising FGF1, or OMP128 comprising FGF2.

23. The method according to claim 13, wherein the membrane spanning protein is OMP18.

24. The method according to claim 1, wherein the membrane spanning protein is OmpA depicted in SEQ ID NO: 1 or the amino acid sequence encoded by SEQ ID NO: 2.

25. The method according to claim 1, wherein the substrate is selected from the group consisting of a mesh, fibres, beads, knitted or woven fabric, micro-well plates, array, and tissue culture flasks.

26. The method according to claim 1, wherein the membrane spanning protein is OmpA modified to further comprise a heterologous protein or peptide fused to the spacer.

27. The method according to claim 1, wherein the membrane spanning protein is OmpA modified to further comprise an alpha helical spacer at the N terminus.

28. The method according to claim 1, wherein the membrane spanning protein is eukaryotic, animal, mammalian, or prokaryotic.

29. The method according to claim 1, wherein the substrate is selected from the group consisting of plastic, silk and other proteinaceous fibres, and graphene, and wherein when the substrate is plastic it is selected from polyvinyl, polyethylene (PE), polyacrylate (acrylic), polystyrene (PS), silicone, polyester, polyurethane, polypropylene (PP), polyamide (nylon), Acrylonitrile butadiene styrene (ABS), Polyethylene/Acrylonitrile Butadiene Styrene (PE/ABS), bakelite, rubber, latex, polycarbonate (PC), Polycarbonate/Acrylonitrile Butadiene Styrene (PC/ABS) and polyvinyl chloride.

* * * * *

SEQUENCE LISTING

```
<160> NUMBER OF SEQ ID NOS: 48

<210> SEQ ID NO 1
<211> LENGTH: 594
<212> TYPE: DNA
<213> ORGANISM: Artificial Sequence
<220> FEATURE:
<223> OTHER INFORMATION: OMP0 "wild-type" modified by removal of signal
      and C-terminal domain and addition of N-terminal his tag and
      cysteine at position 10.

<400> SEQUENCE: 1
atgcatcacc atcaccatca ctcgagctgt gctccgaaag ataacacctg gtacactggt      60
gctaaactgg gctggtccca gtaccatgac actggtttca tcaacaacaa tggcccgacc     120
catgaaaacc aactgggcgc tggtgctttt ggtggttacc aggttaaccc gtatgttggc     180
tttgaaatgg gttacgactg gttaggtcgt atgccgtaca aaggcagcgt tgaaaacggt     240
gcatacaaag ctcagggcgt tcaactgacc gctaaactgg gttacccaat cactgacgac     300
ctggacatct acactcgtct gggtggcatg gtatggcgtg cagacactaa atccaacgtt     360
tatggtaaaa accacgacac cggcgtttct ccggtcttcg ctggcggtgt tgagtacgcg     420
atcactcctg aaatcgctac ccgtctggaa taccagtgga ccaacaacat cggtgacgca     480
cacaccatcg gcactcgtcc ggacaacggc atgctgagcc tgggtgtttc ctaccgtttc     540
ggtcagggcg aagcagctcc agtagttgct ccggctccag ctccggcacc gtaa           594

<210> SEQ ID NO 2
<211> LENGTH: 197
<212> TYPE: PRT
<213> ORGANISM: Artificial Sequence
<220> FEATURE:
<223> OTHER INFORMATION: OMP0 "wild-type" modified by removal of signal
      and C-terminal domain and addition of N-terminal his tag and
      cysteine at position 10.

<400> SEQUENCE: 2

Met His His His His His His Ser Ser Cys Ala Pro Lys Asp Asn Thr
1               5                   10                  15

Trp Tyr Thr Gly Ala Lys Leu Gly Trp Ser Gln Tyr His Asp Thr Gly
            20                  25                  30

Phe Ile Asn Asn Asn Gly Pro Thr His Glu Asn Gln Leu Gly Ala Gly
        35                  40                  45

Ala Phe Gly Gly Tyr Gln Val Asn Pro Tyr Val Gly Phe Glu Met Gly
    50                  55                  60

Tyr Asp Trp Leu Gly Arg Met Pro Tyr Lys Gly Ser Val Glu Asn Gly
65                  70                  75                  80

Ala Tyr Lys Ala Gln Gly Val Gln Leu Thr Ala Lys Leu Gly Tyr Pro
                85                  90                  95

Ile Thr Asp Asp Leu Asp Ile Tyr Thr Arg Leu Gly Gly Met Val Trp
            100                 105                 110
```

```
Arg Ala Asp Thr Lys Ser Asn Val Tyr Gly Lys Asn His Asp Thr Gly
        115                 120                 125

Val Ser Pro Val Phe Ala Gly Gly Val Glu Tyr Ala Ile Thr Pro Glu
    130                 135                 140

Ile Ala Thr Arg Leu Glu Tyr Gln Trp Thr Asn Asn Ile Gly Asp Ala
145                 150                 155                 160

His Thr Ile Gly Thr Arg Pro Asp Asn Gly Met Leu Ser Leu Gly Val
                165                 170                 175

Ser Tyr Arg Phe Gly Gln Gly Glu Ala Ala Pro Val Val Ala Pro Ala
            180                 185                 190

Pro Ala Pro Ala Pro
        195

<210> SEQ ID NO 3
<211> LENGTH: 558
<212> TYPE: DNA
<213> ORGANISM: Artificial Sequence
<220> FEATURE:
<223> OTHER INFORMATION: OMP9 Loop 1 circular permutation

<400> SEQUENCE: 3
atgcatcacc atcaccatca ctcgagtgaa aaccaactgg gcgctggtgc ttttggtggt     60
taccaggtta acccgtatgt tggctttgaa atgggttacg actggttagg tcgtatgccg    120
tacaaaggca gcgttgaaaa cggtgcatac aaagctcagg gcgttcaact gaccgctaaa    180
ctgggttacc caatcactga cgacctggac atctacactc gtttgggtgg catggtatgg    240
cgtgcagaca ctaaatccaa cgtttatggt aaaaaccacg acaccggcgt ttctccggtc    300
ttcgctggcg gtgttgagta cgcgatcact cctgaaatcg ctacccgtct ggaataccag    360
tggaccaaca acatcggtga cgcacacacc atcggcactc gtccggacaa cggcatgctg    420
agcctgggtg tttcctaccg tttcggtccg tgtacaggtg ataccctggta cactggtgct    480 aaactgggct ggtcccagta ccatgacact ggtttcatca caacaatgg cccaacccat    540 acgcgtgagg aattttga                                                 558

<210> SEQ ID NO 4
<211> LENGTH: 185
<212> TYPE: PRT
<213> ORGANISM: Artificial Sequence
<220> FEATURE:
<223> OTHER INFORMATION: OMP9 Loop 1 circular permutation

<400> SEQUENCE: 4

Met His His His His His Ser Ser Glu Asn Gln Leu Gly Ala Gly
1               5                   10                  15

Ala Phe Gly Gly Tyr Gln Val Asn Pro Tyr Val Gly Phe Glu Met Gly
            20                  25                  30

Tyr Asp Trp Leu Gly Arg Met Pro Tyr Lys Gly Ser Val Glu Asn Gly
        35                  40                  45

Ala Tyr Lys Ala Gln Gly Val Gln Leu Thr Ala Lys Leu Gly Tyr Pro
    50                  55                  60

Ile Thr Asp Asp Leu Asp Ile Tyr Thr Arg Leu Gly Gly Met Val Trp
65                  70                  75                  80

Arg Ala Asp Thr Lys Ser Asn Val Tyr Gly Lys Asn His Asp Thr Gly
                85                  90                  95

Val Ser Pro Val Phe Ala Gly Gly Val Glu Tyr Ala Ile Thr Pro Glu
            100                 105                 110
```

Ile Ala Thr Arg Leu Glu Tyr Gln Trp Thr Asn Asn Ile Gly Asp Ala
            115                 120                 125

His Thr Ile Gly Thr Arg Pro Asp Asn Gly Met Leu Ser Leu Gly Val
        130                 135                 140

Ser Tyr Arg Phe Gly Pro Cys Thr Gly Asp Thr Trp Tyr Thr Gly Ala
145                 150                 155                 160

Lys Leu Gly Trp Ser Gln Tyr His Asp Thr Gly Phe Ile Asn Asn
                165                 170                 175

Gly Pro Thr His Thr Arg Glu Glu Phe
            180                 185

<210> SEQ ID NO 5
<211> LENGTH: 555
<212> TYPE: DNA
<213> ORGANISM: Artificial Sequence
<220> FEATURE:
<223> OTHER INFORMATION: OMP13 Loop 3 circular permutation

<400> SEQUENCE: 5
atgcatcacc atcaccatca ctcgagttct ccggtcttcg ctggcggtgt tgagtacgcg      60
atcactcctg aaatcgctac ccgtctggaa taccagtgga ccaacaacat cggtgacgca     120
cacaccatcg gcactcgtcc ggacaacggc atgctgagcc tgggtgtttc ctaccgtttc     180
ggtccgtgta caggtgatac ctggtacact ggtgctaaac tgggctggtc ccagtaccat     240
gacactggtt tcatcaacaa caatggcccg acccatgaaa accaactggg cgctggtgct     300
tttggtggtt accaggttaa cccgtatgtt ggctttgaaa tgggttacga ctggttaggt     360
cgtatgccgt acaaaggcag cgttgaaaac ggtgcataca agctcagggg cgttcaactg     420
accgctaaac tggttacccc aatcactgac gacctggaca tctacactcg tctgggtggc     480
atggtatggc gtgcagacac taaatccaac gtttatggta aaaccacga caccggcacg     540
cgtgaggaat tttga                                                      555

<210> SEQ ID NO 6
<211> LENGTH: 184
<212> TYPE: PRT
<213> ORGANISM: Artificial Sequence
<220> FEATURE:
<223> OTHER INFORMATION: OMP13 Loop 3 circular permutation

<400> SEQUENCE: 6

Met His His His His His His Ser Ser Pro Val Phe Ala Gly Gly
1               5                   10                  15

Val Glu Tyr Ala Ile Thr Pro Glu Ile Ala Thr Arg Leu Glu Tyr Gln
                20                  25                  30

Trp Thr Asn Asn Ile Gly Asp Ala His Thr Ile Gly Thr Arg Pro Asp
            35                  40                  45

Asn Gly Met Leu Ser Leu Gly Val Ser Tyr Arg Phe Gly Pro Cys Thr
        50                  55                  60

Gly Asp Thr Trp Tyr Thr Gly Ala Lys Leu Gly Trp Ser Gln Tyr His
65                  70                  75                  80

Asp Thr Gly Phe Ile Asn Asn Asn Gly Pro Thr His Glu Asn Gln Leu
                85                  90                  95

Gly Ala Gly Ala Phe Gly Gly Tyr Gln Val Asn Pro Tyr Val Gly Phe
            100                 105                 110

Glu Met Gly Tyr Asp Trp Leu Gly Arg Met Pro Tyr Lys Gly Ser Val
        115                 120                 125

Glu Asn Gly Ala Tyr Lys Ala Gln Gly Val Gln Leu Thr Ala Lys Leu
    130                 135                 140

Gly Tyr Pro Ile Thr Asp Asp Leu Asp Ile Tyr Thr Arg Leu Gly Gly
145                 150                 155                 160

Met Val Trp Arg Ala Asp Thr Lys Ser Asn Val Tyr Gly Lys Asn His
                165                 170                 175

Asp Thr Gly Thr Arg Glu Glu Phe
            180

<210> SEQ ID NO 7
<211> LENGTH: 555
<212> TYPE: DNA
<213> ORGANISM: Artificial Sequence
<220> FEATURE:
<223> OTHER INFORMATION: OMP14 Loop 4 circular permutation

<400> SEQUENCE: 7

```
atgcatcacc atcaccatca ctcgagcggc atgctgagcc tgggtgtttc ctaccgtttc      60
ggtccgtgta caggtgatac ctggtacact ggtgctaaac tgggctggtc ccagtaccat     120
gacactggtt tcatcaacaa caatggcccg acccatgaaa accaactggg cgctggtgct     180
tttggtggtt accaggttaa cccgtatgtt ggctttgaaa tgggttacga ctggttaggt     240
cgtatgccgt acaaaggcag cgttgaaaac ggtgcataca agctcagggc cgttcaactg     300
accgctaaac tgggttaccc aatcactgac gacctggaca tctacactcg tctgggtggc     360
atggtatggc gtgcagacac taaatccaac gtttatggta aaaaccacga caccggcgtt     420
tctccggtct cgctggcgg tgttgagtac gcgatcactc ctgaaatcgc tacccgtctg     480
gaataccagt ggaccaacaa catcggtgac gcacacacca tcggcactcg tccggacacg     540
cgtgaggaat tttga                                                      555
```

<210> SEQ ID NO 8
<211> LENGTH: 184
<212> TYPE: PRT
<213> ORGANISM: Artificial Sequence
<220> FEATURE:
<223> OTHER INFORMATION: OMP 14 Loop 4 circular permutation

<400> SEQUENCE: 8

Met His His His His His Ser Ser Gly Met Leu Ser Leu Gly Val
1               5                   10                  15

Ser Tyr Arg Phe Gly Pro Cys Thr Gly Asp Thr Trp Tyr Thr Gly Ala
                20                  25                  30

Lys Leu Gly Trp Ser Gln Tyr His Asp Thr Gly Phe Ile Asn Asn Asn
            35                  40                  45

Gly Pro Thr His Glu Asn Gln Leu Gly Ala Gly Ala Phe Gly Gly Tyr
        50                  55                  60

Gln Val Asn Pro Tyr Val Gly Phe Glu Met Gly Tyr Asp Trp Leu Gly
65                  70                  75                  80

Arg Met Pro Tyr Lys Gly Ser Val Glu Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
    130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Thr Arg Glu Glu Phe
            180

<210> SEQ ID NO 9
<211> LENGTH: 612
<212> TYPE: DNA
<213> ORGANISM: Artificial Sequence
<220> FEATURE:
<223> OTHER INFORMATION: OMP140short loops, alpha helical spacer, c-
      terminal his tag, no cysteine

<400> SEQUENCE: 9
atgtcctcga gcgtagacaa caaattcaac aaagaaaaaa aaaacgcatt ctatgagatc      60
ttacatttac ctaacttaaa cgaagaacaa cgaaacgcct tcatccaaag tttaaaagcg     120
gccccaagcc aaagcgctaa ccttttagca gaagctaaaa agctaaatga tgctcaggcg     180
ccgaaagtag acgcgaattc gagcgaaaac caactgggcg ctggtgcttt tggtggttac     240
caggttaacc cgtatgttgg cttttgaaatg ggttacgact ggttaggtcg tatgccgtac     300
aaagctcagg gcgttcaact gaccgctaaa ctgggttacc caatcactga cgacctggac     360
atctacactc gtttgggtgg catggtatgg cgtgcagaca ctggcgtttc tccggtcttc     420
gctggcggtg ttgagtacgc gatcactcct gaaatcgcta cccgtctgga ataccagtgg     480
accaacaaca tcggtgacaa cggcatgctg agcctgggtg tttcctaccg tttcggtccg     540
atcacaggtg atacctggta cactggtgct aaactgggct ggtcccagta ccatcaccat     600
caccatcact ga                                                         612

<210> SEQ ID NO 10
<211> LENGTH: 203
<212> TYPE: PRT
<213> ORGANISM: Artificial Sequence
<220> FEATURE:
<223> OTHER INFORMATION: OMP140short loops, alpha helical spacer, c-
      terminal his tag, no cysteine

<400> SEQUENCE: 10

Met Ser Ser Ser Val Asp Asn Lys Phe Asn Lys Glu Lys Lys Asn Ala
1               5                   10                  15

Phe Tyr Glu Ile Leu His Leu Pro Asn Leu Asn Glu Glu Gln Arg Asn
            20                  25                  30

Ala Phe Ile Gln Ser Leu Lys Ala Ala Pro Ser Gln Ser Ala Asn Leu
        35                  40                  45

Leu Ala Glu Ala Lys Lys Leu Asn Asp Ala Gln Ala Pro Lys Val Asp
    50                  55                  60

Ala Asn Ser Ser Glu Asn Gln Leu Gly Ala Gly Ala Phe Gly Gly Tyr
65                  70                  75                  80

Gln Val Asn Pro Tyr Val Gly Phe Glu Met Gly Tyr Asp Trp Leu Gly
                85                  90                  95

Arg Met Pro Tyr Lys Ala Gln Gly Val Gln Leu Thr Ala Lys Leu Gly
            100                 105                 110

Tyr Pro Ile Thr Asp Asp Leu Asp Ile Tyr Thr Arg Leu Gly Gly Met
        115                 120                 125

Val Trp Arg Ala Asp Thr Gly Val Ser Pro Val Phe Ala Gly Gly Val

```
                130              135                 140
Glu Tyr Ala Ile Thr Pro Glu Ile Ala Thr Arg Leu Glu Tyr Gln Trp
145                 150                 155                 160

Thr Asn Asn Ile Gly Asp Asn Gly Met Leu Ser Leu Gly Val Ser Tyr
                165                 170                 175

Arg Phe Gly Pro Ile Thr Gly Asp Thr Trp Tyr Thr Gly Ala Lys Leu
            180                 185                 190

Gly Trp Ser Gln Tyr His His His His His His
        195                 200
```

<210> SEQ ID NO 11
<211> LENGTH: 600
<212> TYPE: DNA
<213> ORGANISM: Artificial Sequence
<220> FEATURE:
<223> OTHER INFORMATION: OMP154 OMP0 with short loops and truncated C-
      term, but loop 1 elongated

<400> SEQUENCE: 11

```
atgcatcacc atcaccatca ctcgagcggt gctccgaaag ataacacctg gtacactggt      60
gctaaactgg ctggtcccag gtaccatgac actggtttca tcaacaacac ccctacccca     120
acgccgacgc ctactccgca acagtcgacc aaccaacccg gacgaatca acagccgacg      180 ccgacgccaa ccccaacccc aaatggcccg acccatgaaa accaactggg cgctggtgct     240
tttggtggtt accaggttaa cccgtatgtt ggctttgaaa tgggttacga ctggttaggt     300
cgtatgccgt acaaagctca gggcgttcaa ctgaccgcta aactgggtta cccaatcact     360
gacgacctgg acatctacac tcgtctgggt ggcatggtat ggcgtgcaga cactggcgtt     420
tctccggtct cgctggcgg tgttgagtac gcgatcactc tgaaaatcgc tacccgtctg     480
gaataccagt ggaccaacaa catcaacggc atgctgagcc tgggtgtttc ctaccgtttc     540
ggtcagtaaa cgcgtgagga attttgaaga tccggctgct aacaaagccc gaaaggaagc    600
```

<210> SEQ ID NO 12
<211> LENGTH: 182
<212> TYPE: PRT
<213> ORGANISM: Artificial Sequence
<220> FEATURE:
<223> OTHER INFORMATION: OMP154 OMP0 with short loops and truncated C-
      term, but loop 1 elongated.

<400> SEQUENCE: 12

```
Met His His His His His His Ser Ser Gly Ala Pro Lys Asp Asn Thr
1               5                   10                  15

Trp Tyr Thr Gly Ala Lys Leu Gly Trp Ser Gln Tyr His Asp Thr Gly
            20                  25                  30

Phe Ile Asn Asn Thr Pro Thr Pro Thr Pro Thr Pro Thr Pro Gln Gln
        35                  40                  45

Ser Thr Asn Gln Pro Gly Thr Asn Gln Gln Pro Thr Pro Thr Pro Thr
    50                  55                  60

Pro Thr Pro Asn Gly Pro Thr His Glu Asn Gln Leu Gly Ala Gly Ala
65                  70                  75                  80

Phe Gly Gly Tyr Gln Val Asn Pro Tyr Val Gly Phe Glu Met Gly Tyr
                85                  90                  95

Asp Trp Leu Gly Arg Met Pro Tyr Lys Ala Gln Gly Val Gln Leu Thr
            100                 105                 110

Ala Lys Leu Gly Tyr Pro Ile Thr Asp Asp Leu Asp Ile Tyr Thr Arg
        115                 120                 125
```

Leu Gly Gly Met Val Trp Arg Ala Asp Thr Gly Val Ser Pro Val Phe
            130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Asn Gly Met Leu Ser Leu Gly Val
                165                 170                 175

Ser Tyr Arg Phe Gly Gln
            180

<210> SEQ ID NO 13
<211> LENGTH: 426
<212> TYPE: DNA
<213> ORGANISM: Artificial Sequence
<220> FEATURE:
<223> OTHER INFORMATION: OMP170 short loops, n-terminal his tag,
      cysteine at aa 122

<400> SEQUENCE: 13
atgcatcacc atcaccatca ctcgagtgaa aaccaactgg gcgctggtgc ttttggtggt      60
taccaggtta acccgtatgt tggctttgaa atgggttacg actggttagg tcgtatgccg     120
tacaaagctc agggcgttca actgaccgct aaactgggtt acccaatcac tgacgacctg     180
gacatctaca ctcgtttggg tggcatggta tggcgtgcag acactggcgt ttctccggtc     240
ttcgctggcg gtgttgagta cgcgatcact cctgaaatcg ctacccgtct ggaataccag     300
tggaccaaca acatcggtga caacggcatg ctgagcctgg gtgtttccta ccgtttcggt     360
ccgtgtacag gtgataccctg gtacactggt gctaaactgg gctggtccca gtacaaccag     420
tgataa                                                                426

<210> SEQ ID NO 14
<211> LENGTH: 140
<212> TYPE: PRT
<213> ORGANISM: Artificial Sequence
<220> FEATURE:
<223> OTHER INFORMATION: OMP170 short loops, n-terminal his tag,
      cysteine at aa 122

<400> SEQUENCE: 14

Met His His His His His Ser Ser Glu Asn Gln Leu Gly Ala Gly
1               5                   10                  15

Ala Phe Gly Gly Tyr Gln Val Asn Pro Tyr Val Gly Phe Glu Met Gly
            20                  25                  30

Tyr Asp Trp Leu Gly Arg Met Pro Tyr Lys Ala Gln Gly Val Gln Leu
        35                  40                  45

Thr Ala Lys Leu Gly Tyr Pro Ile Thr Asp Asp Leu Asp Ile Tyr Thr
50                  55                  60

Arg Leu Gly Gly Met Val Trp Arg Ala Asp Thr Gly Val Ser Pro Val
65                  70                  75                  80

Phe Ala Gly Gly Val Glu Tyr Ala Ile Thr Pro Glu Ile Ala Thr Arg
            85                  90                  95

Leu Glu Tyr Gln Trp Thr Asn Asn Ile Gly Asp Asn Gly Met Leu Ser
        100                 105                 110

Leu Gly Val Ser Tyr Arg Phe Gly Pro Cys Thr Gly Asp Thr Trp Tyr
            115                 120                 125

Thr Gly Ala Lys Leu Gly Trp Ser Gln Tyr Asn Gln
        130                 135                 140

<210> SEQ ID NO 15
<211> LENGTH: 627
<212> TYPE: DNA
<213> ORGANISM: Artificial Sequence
<220> FEATURE:
<223> OTHER INFORMATION: OMP171, as 170 but with alpha helical spacer after his tag.

<400> SEQUENCE: 15

```
atgcatcacc atcaccatca ctcgagcgta gacaacaaat caacaaaga aaaaaaaac      60
gcattctatg agatcttaca tttacctaac ttaaacgaag aacaacgaaa cgccttcatc   120
caaagtttaa aagcggcccc aagccaaagc gctaaccttt tagcagaagc taaaaagcta   180
aatgatgctc aggcgccgaa agtagacgcg aattcgagca cgtcgagtga aaaccaactg   240
ggcgctggtg cttttggtgg ttaccaggtt aacccgtatg ttggctttga atgggttac    300
gactggttag gtcgtatgcc gtacaaagct cagggcgttc aactgaccgc taaactgggt   360
tacccaatca ctgacgacct ggacatctac actcgtttgg gtggcatggt atggcgtgca   420
gacactggcg tttctccggt cttcgctggc ggtgttgagt acgcgatcac tcctgaaatc   480
gctacccgtc tggaatacca gtggaccaac aacatcggtg acaacggcat gctgagcctg   540
ggtgtttcct accgtttcgg tccgtgtaca ggtgatacct ggtacactgg tgctaaactg   600
ggctggtccc agtacaacca gtgataa                                       627
```

<210> SEQ ID NO 16
<211> LENGTH: 207
<212> TYPE: PRT
<213> ORGANISM: Artificial Sequence
<220> FEATURE:
<223> OTHER INFORMATION: OMP171, as 170 but with alpha helical spacer after his tag

<400> SEQUENCE: 16

```
Met His His His His His Ser Ser Val Asp Asn Lys Phe Asn Lys
1               5                   10                  15

Glu Lys Lys Asn Ala Phe Tyr Glu Ile Leu His Leu Pro Asn Leu Asn
            20                  25                  30

Glu Glu Gln Arg Asn Ala Phe Ile Gln Ser Leu Lys Ala Ala Pro Ser
        35                  40                  45

Gln Ser Ala Asn Leu Leu Ala Glu Ala Lys Lys Leu Asn Asp Ala Gln
    50                  55                  60

Ala Pro Lys Val Asp Ala Asn Ser Ser Thr Ser Ser Glu Asn Gln Leu
65                  70                  75                  80

Gly Ala Gly Ala Phe Gly Gly Tyr Gln Val Asn Pro Tyr Val Gly Phe
                85                  90                  95

Glu Met Gly Tyr Asp Trp Leu Gly Arg Met Pro Tyr Lys Ala Gln Gly
            100                 105                 110

Val Gln Leu Thr Ala Lys Leu Gly Tyr Pro Ile Thr Asp Asp Leu Asp
        115                 120                 125

Ile Tyr Thr Arg Leu Gly Gly Met Val Trp Arg Ala Asp Thr Gly Val
    130                 135                 140

Ser Pro Val Phe Ala Gly Gly Val Glu Tyr Ala Ile Thr Pro Glu Ile
145                 150                 155                 160

Ala Thr Arg Leu Glu Tyr Gln Trp Thr Asn Asn Ile Gly Asp Asn Gly
                165                 170                 175

Met Leu Ser Leu Gly Val Ser Tyr Arg Phe Gly Pro Cys Thr Gly Asp
            180                 185                 190
```

```
Thr Trp Tyr Thr Gly Ala Lys Leu Gly Trp Ser Gln Tyr Asn Gln
        195                 200                 205
```

<210> SEQ ID NO 17
<211> LENGTH: 252
<212> TYPE: PRT
<213> ORGANISM: Artificial Sequence
<220> FEATURE:
<223> OTHER INFORMATION: OMP59

<400> SEQUENCE: 17

```
Met His His His His His Ser Ser Val Asp Asn Lys Phe Asn Lys
  1               5                  10                  15

Glu Gln Gln Asn Ala Phe Tyr Glu Ile Leu His Leu Pro Asn Leu Asn
                 20                  25                  30

Glu Glu Gln Arg Asn Ala Phe Ile Gln Ser Leu Lys Asp Asp Pro Ser
             35                  40                  45

Gln Ser Ala Asn Leu Leu Ala Glu Ala Lys Lys Leu Asn Asp Ala Gln
     50                  55                  60

Ala Pro Lys Val Asp Ala Asn Ser Ser Thr Ser Ser Glu Asn Gln Leu
 65                  70                  75                  80

Gly Ala Gly Ala Phe Gly Gly Tyr Gln Val Asn Pro Tyr Val Gly Phe
                 85                  90                  95

Glu Met Gly Tyr Asp Trp Leu Gly Arg Met Pro Tyr Lys Gly Ser Val
            100                 105                 110

Glu Asn Gly Ala Tyr Lys Ala Gln Gly Val Gln Leu Thr Ala Lys Leu
        115                 120                 125

Gly Tyr Pro Ile Thr Asp Asp Leu Asp Ile Tyr Thr Arg Leu Gly Gly
    130                 135                 140

Met Val Trp Arg Ala Asp Thr Lys Ser Asn Val Tyr Gly Lys Asn His
145                 150                 155                 160

Asp Thr Gly Val Ser Pro Val Phe Ala Gly Gly Val Glu Tyr Ala Ile
                165                 170                 175

Thr Pro Glu Ile Ala Thr Arg Leu Glu Tyr Gln Trp Thr Asn Asn Ile
            180                 185                 190

Gly Asp Ala His Thr Ile Gly Thr Arg Pro Asn Gly Met Leu Ser
        195                 200                 205

Leu Gly Val Ser Tyr Arg Phe Gly Pro Cys Thr Gly Asp Thr Trp Tyr
    210                 215                 220

Thr Gly Ala Lys Leu Gly Trp Ser Gln Tyr His Asp Thr Gly Phe Ile
225                 230                 235                 240

Asn Asn Asn Gly Pro Thr His Thr Arg Glu Glu Phe
                245                 250
```

<210> SEQ ID NO 18
<211> LENGTH: 205
<212> TYPE: PRT
<213> ORGANISM: Artificial Sequence
<220> FEATURE:
<223> OTHER INFORMATION: OMP171

<400> SEQUENCE: 18

```
Met His His His His His Ser Ser Val Asp Asn Lys Phe Asn Lys
  1               5                  10                  15

Glu Lys Lys Asn Ala Phe Tyr Glu Ile Leu His Leu Pro Asn Leu Asn
                 20                  25                  30

Glu Glu Gln Arg Asn Ala Phe Ile Gln Ser Leu Lys Ala Ala Pro Ser
             35                  40                  45
```

```
Gln Ser Ala Asn Leu Leu Ala Glu Ala Lys Lys Leu Asn Asp Ala Gln
        50                  55                  60

Ala Pro Lys Val Asp Ala Asn Ser Ser Thr Glu Asn Gln Leu Gly Ala
 65                  70                  75                  80

Gly Ala Phe Gly Gly Tyr Gln Val Asn Pro Tyr Val Gly Phe Glu Met
                 85                  90                  95

Gly Tyr Asp Trp Leu Gly Arg Met Pro Tyr Lys Ala Gln Gly Val Gln
                100                 105                 110

Leu Thr Ala Lys Leu Gly Tyr Pro Ile Thr Asp Asp Leu Asp Ile Tyr
            115                 120                 125

Thr Arg Leu Gly Gly Met Val Trp Arg Ala Asp Thr Gly Val Ser Pro
        130                 135                 140

Val Phe Ala Gly Gly Val Glu Tyr Ala Ile Thr Pro Glu Ile Ala Thr
145                 150                 155                 160

Arg Leu Glu Tyr Gln Trp Thr Asn Asn Ile Gly Asp Asn Gly Met Leu
                165                 170                 175

Ser Leu Gly Val Ser Tyr Arg Phe Gly Pro Cys Thr Gly Asp Thr Trp
            180                 185                 190

Tyr Thr Gly Ala Lys Leu Gly Trp Ser Gln Tyr Asn Gln
        195                 200                 205

<210> SEQ ID NO 19
<211> LENGTH: 8
<212> TYPE: PRT
<213> ORGANISM: Artificial Sequence
<220> FEATURE:
<223> OTHER INFORMATION: FLAG sequence

<400> SEQUENCE: 19

Asp Tyr Lys Asp Asp Asp Asp Lys
1               5

<210> SEQ ID NO 20
<211> LENGTH: 4
<212> TYPE: PRT
<213> ORGANISM: Artificial Sequence
<220> FEATURE:
<223> OTHER INFORMATION: Short linker

<400> SEQUENCE: 20

Gly Gly Ser Gly
1

<210> SEQ ID NO 21
<211> LENGTH: 8
<212> TYPE: PRT
<213> ORGANISM: Artificial Sequence
<220> FEATURE:
<223> OTHER INFORMATION: Middle Linker

<400> SEQUENCE: 21

Gly Gly Ser Gly Gly Gly Ser Gly
1               5

<210> SEQ ID NO 22
<211> LENGTH: 12
<212> TYPE: PRT
<213> ORGANISM: Artificial Sequence
<220> FEATURE:
<223> OTHER INFORMATION: Long Linker

<400> SEQUENCE: 22
```

Gly Gly Ser Gly Gly Gly Ser Gly Gly Gly Ser Gly
1               5                   10

<210> SEQ ID NO 23
<211> LENGTH: 15
<212> TYPE: PRT
<213> ORGANISM: Artificial Sequence
<220> FEATURE:
<223> OTHER INFORMATION: (Gly4Ser)3 Flexible Peptide Linker

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: Medium 6AA Fusion Protein Linker

<400> SEQUENCE: 24

Gly Gly Ser Gly Gly Ser
1               5

<210> SEQ ID NO 25
<211> LENGTH: 4
<212> TYPE: PRT
<213> ORGANISM: Artificial Sequence
<220> FEATURE:
<223> OTHER INFORMATION: Insert in OMP153

<400> SEQUENCE: 25

Arg Gly Asp Ser
1

<210> SEQ ID NO 26
<211> LENGTH: 5
<212> TYPE: PRT
<213> ORGANISM: Unknown
<220> FEATURE:
<223> OTHER INFORMATION: laminin a1 insert in OMP162

<400> SEQUENCE: 26

Ile Lys Val Ala Val
1               5

<210> SEQ ID NO 27
<211> LENGTH: 5
<212> TYPE: PRT
<213> ORGANISM: Unknown
<220> FEATURE:
<223> OTHER INFORMATION: laminin b1 insert in OMP163

<400> SEQUENCE: 27

Tyr Ile Gly Ser Arg
1               5

<210> SEQ ID NO 28
<211> LENGTH: 10
<212> TYPE: PRT
<213> ORGANISM: Artificial Sequence
<220> FEATURE:
<223> OTHER INFORMATION: Insert in OMP164

<400> SEQUENCE: 28

```
Pro His Ser Arg Asn Pro His Ser Arg Asn
1               5                   10
```

<210> SEQ ID NO 29
<211> LENGTH: 7
<212> TYPE: PRT
<213> ORGANISM: Unknown
<220> FEATURE:
<223> OTHER INFORMATION: Collagen IV insert in OMP165

<400> SEQUENCE: 29

```
Met Asn Tyr Tyr Ser Asn Ser
1               5
```

<210> SEQ ID NO 30
<211> LENGTH: 7
<212> TYPE: PRT
<213> ORGANISM: Unknown
<220> FEATURE:
<223> OTHER INFORMATION: collagen insert in OMP174

<400> SEQUENCE: 30

```
Phe His Arg Arg Ile Lys Ala
1               5
```

<210> SEQ ID NO 31
<211> LENGTH: 28
<212> TYPE: PRT
<213> ORGANISM: Homo sapiens

<400> SEQUENCE: 31

```
Ile Pro Lys Ala Ser Ser Val Pro Thr Glu Leu Ser Ala Ile Ser Met
1               5                   10                  15

Leu Tyr Leu Asp Glu Asn Glu Lys Val Val Leu Lys
            20                  25
```

<210> SEQ ID NO 32
<211> LENGTH: 12
<212> TYPE: PRT
<213> ORGANISM: Homo sapiens

<400> SEQUENCE: 32

```
Pro Gln Val Thr Arg Gly Asp Val Phe Thr Met Pro
1               5                   10
```

<210> SEQ ID NO 33
<211> LENGTH: 16
<212> TYPE: PRT
<213> ORGANISM: Homo sapiens

<400> SEQUENCE: 33

```
Lys Lys Gln Arg Phe Arg His Arg Asn Arg Lys Gly Tyr Ser Arg Gln
1               5                   10                  15
```

<210> SEQ ID NO 34
<211> LENGTH: 24
<212> TYPE: PRT
<213> ORGANISM: Homo sapiens

<400> SEQUENCE: 34

```
Val Asp Thr Tyr Asp Gly Arg Gly Asp Ser Val Val Tyr Gly Leu Arg
1               5                   10                  15

Ser Lys Ser Lys Lys Phe Arg Arg
            20
```

<210> SEQ ID NO 35
<211> LENGTH: 8
<212> TYPE: PRT
<213> ORGANISM: Homo sapiens

<400> SEQUENCE: 35

Val Phe Asp Asn Phe Val Leu Lys
1               5

<210> SEQ ID NO 36
<211> LENGTH: 14
<212> TYPE: PRT
<213> ORGANISM: Unknown
<220> FEATURE:
<223> OTHER INFORMATION: collagen insert in OMP185

<400> SEQUENCE: 36

Gly Thr Pro Gly Pro Gln Gly Ile Ala Gly Gln Arg Val Val
1               5                   10

<210> SEQ ID NO 37
<211> LENGTH: 15
<212> TYPE: PRT
<213> ORGANISM: Unknown
<220> FEATURE:
<223> OTHER INFORMATION: Hiv TAT insert in OMP186

<400> SEQUENCE: 37

Ser Tyr Gly Arg Lys Lys Arg Arg Gln Arg Arg Arg Ala His Gln
1               5                   10                  15

<210> SEQ ID NO 38
<211> LENGTH: 12
<212> TYPE: PRT
<213> ORGANISM: Unknown
<220> FEATURE:
<223> OTHER INFORMATION: lamimin a2 insert in OMP187

<400> SEQUENCE: 38

Val Gln Leu Arg Asn Gly Phe Pro Tyr Phe Ser Tyr
1               5                   10

<210> SEQ ID NO 39
<211> LENGTH: 12
<212> TYPE: PRT
<213> ORGANISM: Unknown
<220> FEATURE:
<223> OTHER INFORMATION: laminin a2 insert in OMP188

<400> SEQUENCE: 39

Gly Leu Leu Phe Tyr Met Ala Arg Ile Asn His Ala
1               5                   10

<210> SEQ ID NO 40
<211> LENGTH: 5
<212> TYPE: PRT
<213> ORGANISM: Unknown
<220> FEATURE:
<223> OTHER INFORMATION: laminin a2 insert in OMP189

<400> SEQUENCE: 40

Ile Lys Val Ser Val
1               5

<210> SEQ ID NO 41
<211> LENGTH: 8

```
<212> TYPE: PRT
<213> ORGANISM: Homo sapiens

<400> SEQUENCE: 41

Ser Pro Leu Pro Ile Thr Pro Val
1               5

<210> SEQ ID NO 42
<211> LENGTH: 176
<212> TYPE: PRT
<213> ORGANISM: Homo sapiens

<400> SEQUENCE: 42

Ala Pro Thr Ala Pro Asn Gly Thr Leu Glu Ala Glu Leu Glu Arg Arg
1               5                   10                  15

Trp Glu Ser Leu Val Ala Leu Ser Leu Ala Arg Leu Pro Val Ala Ala
                20                  25                  30

Gln Pro Lys Glu Ala Ala Val Gln Ser Gly Ala Gly Asp Tyr Leu Leu
            35                  40                  45

Gly Ile Lys Arg Leu Arg Arg Leu Tyr Cys Asn Val Gly Ile Gly Phe
    50                  55                  60

His Leu Gln Ala Leu Pro Asp Gly Arg Ile Gly Gly Ala His Ala Asp
65                  70                  75                  80

Thr Arg Asp Ser Leu Leu Glu Leu Ser Pro Val Glu Arg Gly Val Val
                85                  90                  95

Ser Ile Phe Gly Val Ala Ser Arg Phe Phe Val Ala Met Ser Ser Lys
            100                 105                 110

Gly Lys Leu Tyr Gly Ser Pro Phe Phe Thr Asp Glu Cys Thr Phe Lys
        115                 120                 125

Glu Ile Leu Leu Pro Asn Asn Tyr Asn Ala Tyr Glu Ser Tyr Lys Tyr
    130                 135                 140

Pro Gly Met Phe Ile Ala Leu Ser Lys Asn Gly Lys Thr Lys Lys Gly
145                 150                 155                 160

Asn Arg Val Ser Pro Thr Met Lys Val Thr His Phe Leu Pro Arg Leu
                165                 170                 175

<210> SEQ ID NO 43
<211> LENGTH: 129
<212> TYPE: PRT
<213> ORGANISM: Homo sapiens

<400> SEQUENCE: 43

His Lys Cys Asp Ile Thr Leu Gln Glu Ile Lys Thr Leu Asn Ser
1               5                   10                  15

Leu Thr Glu Gln Lys Thr Leu Cys Thr Glu Leu Thr Val Thr Asp Ile
                20                  25                  30

Phe Ala Ala Ser Lys Asn Thr Thr Glu Lys Glu Thr Phe Cys Arg Ala
            35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
```

Ser

<210> SEQ ID NO 44
<211> LENGTH: 165
<212> TYPE: PRT
<213> ORGANISM: Homo sapiens

<400> SEQUENCE: 44

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Gly Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala
                165

<210> SEQ ID NO 45
<211> LENGTH: 174
<212> TYPE: PRT
<213> ORGANISM: Homo sapiens

<400> SEQUENCE: 45

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Ser Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

```
Ala Gly Phe Asp Trp Val Tyr Tyr Glu Ser Lys Ala His Ile His Cys
145                 150                 155                 160

Ser Val Lys Ala Glu Asn Ser Val Ala Lys Ser Gly Gly
                165                 170
```

<210> SEQ ID NO 46
<211> LENGTH: 127
<212> TYPE: PRT
<213> ORGANISM: Homo sapiens

<400> SEQUENCE: 46

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 47
<211> LENGTH: 133
<212> TYPE: PRT
<213> ORGANISM: Homo sapiens

<400> SEQUENCE: 47

```
Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
        130
```

<210> SEQ ID NO 48
<211> LENGTH: 173
<212> TYPE: PRT
<213> ORGANISM: Homo sapiens

```
<400> SEQUENCE: 48

Pro Ala Pro Pro Ala Cys Asp Leu Arg Val Leu Ser Lys Leu Leu Arg
1               5                   10                  15

Asp Ser His Val Leu His Ser Arg Leu Ser Gln Cys Pro Glu Val His
            20                  25                  30

Pro Leu Pro Thr Pro Val Leu Leu Pro Ala Val Asp Phe Ser Leu Gly
            35                  40                  45

Glu Trp Lys Thr Gln Met Glu Glu Thr Lys Ala Gln Asp Ile Leu Gly
    50                  55                  60

Ala Val Thr Leu Leu Leu Glu Gly Val Met Ala Ala Arg Gly Gln Leu
65              70                  75                  80

Gly Pro Thr Cys Leu Ser Ser Leu Leu Gly Gln Leu Ser Gly Gln Val
            85                  90                  95

Arg Leu Leu Leu Gly Ala Leu Gln Ser Leu Leu Gly Thr Gln Leu Pro
            100                 105                 110

Pro Gln Gly Arg Thr Thr Ala His Lys Asp Pro Asn Ala Ile Phe Leu
        115                 120                 125

Ser Phe Gln His Leu Leu Arg Gly Lys Val Arg Phe Leu Met Leu Val
        130                 135                 140

Gly Gly Ser Thr Leu Cys Val Arg Arg Ala Pro Pro Thr Thr Ala Val
145                 150                 155                 160

Pro Ser Arg Thr Ser Leu Val Leu Thr Leu Asn Glu Leu
                165                 170
```